(12) United States Patent
Burk et al.

(10) Patent No.: US 11,525,149 B2
(45) Date of Patent: Dec. 13, 2022

(54) MICROORGANISMS AND METHODS FOR THE BIOSYNTHESIS OF FUMARATE, MALATE, AND ACRYLATE

(71) Applicant: Genomatica, Inc., San Diego, CA (US)

(72) Inventors: Mark J. Burk, San Diego, CA (US); Anthony P. Burgard, Bellefonte, PA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 15/600,479

(22) Filed: May 19, 2017

(65) Prior Publication Data

US 2018/0363012 A1   Dec. 20, 2018

Related U.S. Application Data

(63) Continuation of application No. 14/716,767, filed on May 19, 2015, now Pat. No. 9,689,006, which is a continuation of application No. 13/372,332, filed on Feb. 13, 2012, now Pat. No. 9,062,330, which is a continuation of application No. 12/486,724, filed on Jun. 17, 2009, now Pat. No. 8,129,154.

(60) Provisional application No. 61/088,628, filed on Aug. 13, 2008, provisional application No. 61/077,127, filed on Jun. 30, 2008, provisional application No. 61/073,348, filed on Jun. 17, 2008.

(51) Int. Cl.
| | |
|---|---|
| *C12P 7/46* | (2006.01) |
| *C12N 15/00* | (2006.01) |
| *C12N 9/00* | (2006.01) |
| *C12P 7/04* | (2006.01) |
| *C12P 7/40* | (2006.01) |
| *C12N 9/88* | (2006.01) |

(52) U.S. Cl.
CPC .............. *C12P 7/46* (2013.01); *C12N 9/88* (2013.01); *C12P 7/40* (2013.01)

(58) Field of Classification Search
CPC .. C12P 7/46; C12N 9/00; C12N 15/00; C12N 1/22; C07H 21/04
See application file for complete search history.

(56) References Cited

U.S. PATENT DOCUMENTS

| | | | |
|---|---|---|---|
| 5,079,143 A | 1/1992 | Klein et al. | |
| 6,133,014 A | 10/2000 | Mukouyama et al. | |
| 6,485,947 B1 | 11/2002 | Rajgarhia et al. | |
| 7,127,379 B2 | 10/2006 | Palsson et al. | |
| 7,799,545 B2 | 9/2010 | Burgard et al. | |
| 7,803,589 B2 | 9/2010 | Burk et al. | |
| 7,858,350 B2 | 12/2010 | Burk et al. | |
| 7,947,483 B2 | 5/2011 | Burgard et al. | |
| 7,977,084 B2 | 7/2011 | Sun et al. | |
| 8,026,386 B2 | 9/2011 | Burk et al. | |
| 8,048,661 B2 | 11/2011 | Burgard et al. | |
| 8,062,871 B2 | 11/2011 | Burgard et al. | |
| 8,067,214 B2 | 11/2011 | Burk et al. | |
| 8,088,607 B2 | 1/2012 | Burgard et al. | |
| 8,129,154 B2 | 3/2012 | Burk et al. | |
| 8,129,155 B2 | 3/2012 | Trawick et al. | |
| 8,129,156 B2 | 3/2012 | Burk et al. | |
| 8,129,169 B2 | 3/2012 | Van Dien et al. | |
| 8,178,327 B2 | 5/2012 | Burk et al. | |
| 8,241,877 B2 | 8/2012 | Burgard et al. | |
| 8,268,607 B2 | 9/2012 | Burgard | |
| 2002/0012939 A1 | 1/2002 | Palsson | |
| 2002/0168654 A1 | 11/2002 | Maranas et al. | |
| 2003/0059792 A1 | 3/2003 | Palsson et al. | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2006/0040368 A1* | 2/2006 | San .......................... | C12P 7/46 |
| | | | 435/144 |
| 2006/0110810 A1 | 5/2006 | Rajgarhia et al. | |
| 2006/0281156 A1 | 12/2006 | Aoyama et al. | |
| 2007/0037265 A1 | 2/2007 | Zhou et al. | |

(Continued)

FOREIGN PATENT DOCUMENTS

| | | |
|---|---|---|
| EP | 2017344 | 1/2009 |
| WO | WO 2002/042418 A2 | 5/2002 |

(Continued)

OTHER PUBLICATIONS

Altamirano et al., "Decoupling cell growth and product formation in Chinese hamster ovary cells throguh metabolic control," *Biotechnol. Bioeng.* 76(4):351-360 (2001).
Ausubel et al., *Current Protocols in Molecular Biology*, John Wiley and Sons, Baltimore, MD (1999).
Barthelmebs et al., "Exression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.*, 67:1063-1069 (2001).
Barthelmebs et al., "Inducible metabolism of phenolic acids in Pedicoccus pentosaecus is encoded by an autoregulated operon which involves a new class of negative transcriptional regulator," *J. Bacteriol.*, 182:6724-6731 (2000).
Bergquist et al., "Degenerate oligonucleotide gene shuffling," *Meth. Mol. Biol.*, 352:191-204 (2007).

(Continued)

*Primary Examiner* — Maryam Monshipouri
(74) *Attorney, Agent, or Firm* — Greenberg Traurig

(57) ABSTRACT

A non-naturally occurring eukaryotic or prokaryotic organism includes one or more gene disruptions occurring in genes encoding enzymes imparting increased fumarate, malate or acrylate production in the organism when the gene disruption reduces an activity of the enzyme. The one or more gene disruptions confers increased production of acrylate onto the organism. Organisms that produce acrylate have an acrylate pathway that at least one exogenous nucleic acid encoding an acrylate pathway enzyme expressed in a sufficient amount to produce acrylate, the acrylate pathway comprising a decarboxylase. Methods of producing fumarate, malate or acrylate include culturing these organisms.

12 Claims, 21 Drawing Sheets

(56) References Cited

U.S. PATENT DOCUMENTS

| | | |
|---|---|---|
| 2007/0042476 A1 | 2/2007 | Lee et al. |
| 2007/0111294 A1 | 5/2007 | Burgard et al. |
| 2008/0199926 A1 | 8/2008 | Burgard et al. |
| 2009/0047719 A1 | 2/2009 | Burgard et al. |
| 2010/0021978 A1 | 1/2010 | Burk et al. |
| 2010/0184173 A1 | 7/2010 | Burk et al. |
| 2010/0317069 A1 | 12/2010 | Burk et al. |
| 2010/0323418 A1 | 12/2010 | Burgard |
| 2010/0330635 A1 | 12/2010 | Burgard et al. |
| 2011/0003344 A1 | 1/2011 | Burk et al. |
| 2011/0003355 A1 | 1/2011 | Clark et al. |
| 2011/0008858 A1 | 1/2011 | Osterhout et al. |
| 2011/0014668 A1 | 1/2011 | Osterhout et al. |
| 2011/0097767 A1 | 4/2011 | Pharkya |
| 2011/0129899 A1 | 6/2011 | Haselbeck et al. |
| 2011/0195461 A1 | 8/2011 | Burk et al. |
| 2011/0201068 A1 | 8/2011 | Pharkya et al. |
| 2011/0201071 A1 | 8/2011 | Burgard et al. |
| 2011/0207185 A1 | 8/2011 | Osterhout |
| 2011/0207189 A1 | 8/2011 | Osterhout |
| 2011/0212507 A1 | 9/2011 | Burgard et al. |
| 2011/0217742 A1 | 9/2011 | Sun et al. |
| 2011/0223637 A1 | 9/2011 | Burk et al. |
| 2011/0229946 A1 | 9/2011 | Haselbeck et al. |
| 2011/0269204 A1 | 11/2011 | Burk et al. |
| 2011/0300597 A1 | 12/2011 | Burk et al. |
| 2011/0312049 A1 | 12/2011 | Osterhout et al. |
| 2012/0021478 A1 | 1/2012 | Osterhout et al. |
| 2012/0040426 A1 | 2/2012 | Sun et al. |
| 2012/0094345 A1 | 4/2012 | Burk et al. |
| 2012/0115194 A1 | 5/2012 | Burgard et al. |
| 2012/0122171 A1 | 5/2012 | Burk et al. |
| 2012/0156740 A1 | 6/2012 | Pharkya et al. |
| 2012/0208249 A1 | 8/2012 | Trawick et al. |
| 2012/0225463 A1 | 9/2012 | Van Dien et al. |
| 2012/0225466 A1 | 9/2012 | Burk et al. |
| 2012/0237990 A1 | 9/2012 | Burk et al. |
| 2012/0264179 A1 | 10/2012 | Burgard et al. |

FOREIGN PATENT DOCUMENTS

| | | |
|---|---|---|
| WO | WO 2002/042471 A2 | 5/2002 |
| WO | WO 2002/055995 A2 | 7/2002 |
| WO | WO 2003/106998 A1 | 12/2003 |
| WO | WO 2004/092344 A2 | 10/2004 |
| WO | WO 2006/020663 A2 | 2/2006 |
| WO | WO 2007/030830 A2 | 3/2007 |
| WO | WO 2008/013996 A2 | 1/2008 |
| WO | WO 2009/014437 A1 | 1/2009 |

OTHER PUBLICATIONS

Bergquist et al., "Degenerate oligonucleotide gene shuffling (DOGS) and random drift mutagenesis (RNDM): Two complementary techniques for enzyme evolution," *Biomol. Eng.*, 22:63-72 (2005).

Blombach et al., "Corynebacterium glutamicum tailored for high-yield L-valine production," *Appl. Microbiol. Biotechnol.*, 79(3):471-479 (2008).

Bonnarme et al., "Itaconate biosynthesis in Aspergillus terreus," *J. Bacteriol.*, 177(12):3573-3578 (1995).

Brooke et al., "GAMS: A User's Guide. GAMS Development Corporation" (1998).

Burgard et al., "Probing the performance limits of the *Escherichia coli* metabolic network subject to gene additions or deletions," *Biotechnol. Bioeng.*, 74:364-375 (2001).

Burgard et al., "Minimal Reaction Sets for *Escherichia coli* Metabolism under Different Growth Requirements and Uptake Environments," *Biotechnol. Prog.*, 17:791-797 (2001).

Burgard et al., "Optknock: a bilevel programming framework for identifying gene knockout strategies for microbial strain optimization," *Biotechnol. Bioeng.*, 84(6):647-657 (2003).

Carta et al., "Production of fumaric acid by fermentation of enzymatic hydrolysates derived from Cassava bagasse," *Biores. Tech.*, 68:23-28 (1999).

Clausen et al., "PAD1 encodes phenylarcrylic acid decarboxylase which confers resistance to cinnamic acid in *Saccharomyces cerevisiae*," *Gene*, 142:107-112 (1994).

Coco et al., "DNA shuffling method for generating highly recombined genes and evolved enzymes," *Nat. Biotechnol.*, 19:354-359 (2001).

Datsenko et al., "One-step inactivation of chromosomal genes in *Escherichia coli* K-12 using PCR products," *Proc. Natl. Acad. Sci. U.S.A.*, 97:6640-6645 (2000).

Donnelly et al., "A novel fermentation pathway in an *Escherichia coli* mutant producing succinic acid, acetic acid, and ethanol," *App. Biochem. Biotech.*, 70-72:187-198 (1998).

Drake, "Acetogenesis, acetogenic bacteria, and the acetyl-CoA "Wood/Ljungdahl" pathway: past and current perspectives," *Acetogenesis*, H. L. Drake, (ed.), Chapman & Hall, New York, p. 3-60 (1994).

Duarte et al., "Reconstruction and validation of *Saccharomyces cerevisiae* iND750, a fully compartmentalized genome-scale metabolic model," *Genome Res.*, 14(7):1298-1309 (2004).

Durner et al., "Accumulation of Poly[(R)-3-Hydroxyalkanoates] Pseudomonas oleovorans during Growth with Octanoate in continuous culture at Different Dilution Rates," *Appl. Environ. Microbiol.*, 66(8):3408-3414 (2000).

Dwiarti et al., "Purification and characterization of cis-aconitic acid decarboxylase from Aspergillus terreus TN484-M1," *J. Biosci Bioeng.*, 94(1):29-33 (2002).

Edwards et al., "Systems properties of the Haemophilus influenzae Rd metabolic genotype," *J. Biol. Chem.*, 274(25):17410-17416 (1999).

Edwards et al., "The *Escherichia coli* MG1655 in silico Metabolic Genotype: Its Definition, Characteristics, and Capabilities," *Proc. Natl. Acad. Sci. U.S.A.*, 97(10):5528-5533 (2000).

Edwards et al., "In Silico Predictions of *Escherichia coli* metabolic capabilities are Consistent with Experimental Data," *Nat. Biotechnol.*, 19(2):125-130 (2001).

Fell et al., "Fat Synthesis in Adipose Tissue. An Examination of Stoichiometric Constraints," *Biochem. J.*, 238(3):781-786 (1986).

Fong et al., "Metabolic gene-deletion strains of *Escherichia coli* evolve to computationally predicted growth phenotypes," *Nat. Genet.*, 36(10):1056-1058 (2004).

Fong et al., "Description and Interpretation of Adaptive Evolution of *Escherichia coli* K-12 MG1655 by Using a Genome-Scale in Silico Metabolic Model," *J. Bacteriol.*, 185(21):6400-6408 (2003).

Frost, "Redefining chemical manufacture. Replacing petroleum with plant-derived feedstocks," *Ind. Biotechnol.*, 1(1):23-24 (2005).

Fujii et al., "Error-prone rolling circle amplification: the simplest random mutagenesis protocol," *Nat. Protoc.*, 1:2493-2497 (2006).

Fujii et al., "One-step random mutagenesis by error-prone rolling circle amplification," *Nucleic Acids Res.*, 32:e145 (2004).

Gibbs et al., "Degenerate oligonucleotide gene shuffling (DOGS): a method for enhancing the frequency of recombination with family shuffling," *Gene*, 271:13-20 (2001).

Gueldener et al., "A second set of loxP marker cassettes for Cre-mediated multiple gene knockouts in budding yeast," *Nucleic Acids Res.*, 30(6):e23 (2002).

Guerra et al., "Role of transmembrane segment M8 in the biogenesis and function of yeast plasma-membrane H+-ATPase," *Biochim. Biophys. Acta.*, 1768:2383-2392 (2007).

Haarasilta et al., "On the activity and regulation of anaplerotic and gluconeogenetic enzymes during the growth process of baker's yeast. The biphasic growth," *Eur. J. Biochem.*, 52:1-7 (1975).

Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.*, 58(1):217-218 (1994).

Hatakeyama et al., "Gene Cloning and Characterization of Maleate cis-trans Isomerase from Alcaligenes faecalis," *Biochem. Biophys. Res. Comm.*, 239:74-79 (1997).

Hayes et al., "Combining computational and experimental screening for rapid optimization of protein properties," *Proc. Natl. Acad. Sci. U.S.A.*, 99(25):15926-15931 (2002).

Hibbert et al., "Directed evolution of biocatalytic processes," *Biomol. Eng.*, 22:11-19 (2005).

(56) References Cited

OTHER PUBLICATIONS

Hoffmeister et al., "Mitochondrial trans-2-enoyl-CoA reductase of wax ester fermentation from Euglena gracilis defines a new family of enzymes involved in lipid synthesis," *J. Biol. Chem.*, 280(6):4329-4338 (2005).
Hong et al., "The genome sequence of the capnophilic rumen bacterium Mannheimia succiniciproducens," *Nat. Biotechnol.*, 22(10):1275-1281 (2004).
Huang et al., "Purification and characterization of a ferulic acid decarboxylase from Pseudomonas fluorescens," *J. Bacteriol.*, 176:5912-5918 (1994).
Hughes et al., "Evidence for isofunctional enzymes in the degradation of phenol, m- and p-toluate, and p-cresol via catechol meta-cleavage pathways in Alcaligenes eutrophus," *J. Bacteriol.*, 158(1):79-83 (1984).
Huisman et al., "Enzyme evolution for chemical process applications," In R.N. Patel (ed.), *Biocatalysis in the pharmaceutical and biotechnology industries*, CRC Press, p. 717-742 (2007).
Ibarra et al., "*Escherichia coli* K-12 undergoes adaptive evolution to achieve in silico predicted optimal growth," *Nature*, 420(6912):186-189 (2002).
Iwakura et al., "Studies on regulatory functions of malic enzymes. VI. Purification and molecular properties of NADP-linked malic enzyme from *Escherichia coli* W," *J. Biochem.*, 85:1355-1365 (1979).
Jantama et al., "Combining metabolic engineering and metabolic evolution to develop nonrecombinant strains of *Escherichia coli* C that produce succinate and malate," *Biotechnol. Bioeng.*, 99(5):1140-1153 (2008).
Kato et al., "3-Methylaspartate ammonia-lyase as a marker enzyme of the mesaconate pathway for (S)-glutamate fermentation in Enterobacteriaceae," *Arch. Microbiol.*, 168(6):457-463 (1997).
Kenealy et al., "Biochemical Aspects of Fumaric Acid Accumulation by Rhizopus arrhizus," *Appl. Environ. Microbiol.*, 52:128-133 (1986).
Kim et al, "Effect of Overexpression of Actinobacillus succinogenes Phosphoenolpyruvate Carboxykinase on Succinate Production in *Escherichia coli*," *Appl. Env. Microbiol.*, 70(2) 1238-1241 (2004).
Kretz et al., "Gene site saturation mutagenesis: a comprehensive mutagenesis approach," *Methods Enzymol.*, 388:3-11 (2004).
Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.*, 16(9):1448-1452 (2006).
Laivenieks et al., "Cloning sequencing, and overexpression of the Anaerobiospirillum succiniciproducens phosphoenolpyruvate carboxykinase (pckA) gene," *Appl. Environ. Microbiol.*, 63:2273-2280 (1997).
Lee et al., "A new approach to directed gene evolution by recombined extension on truncated templates (RETT)," *J. Molec. Catalysis*, 26:119-129 (2003).
Lee et al., "Cloning and Characterization of Mannheimia succiniciproducens MBEL55E Phosphoenolpyruvate Carboxykinase (pckA) Gene," *Biotechnol. Bioprocess Eng.*, 7:95-99 (2002).
Lee et al., "Fermentative production of chemicals that can be used for polymer synthesis," *Macromol. Biosci.*, 4:157-164 (2004).
Lee et al., "Genome-based metabolic engineering of Mannheimia succiniciproducens for succinic acid productiion," *Appl. Environ. Microbiol.*, 72(3):1939-1948 (2006).
Lian et al., "Stereochemical and Isotopic Labeling Studies of 4-Oxalocrotonate Decarboxylase and Vinylpyruvate hydratase: Analysis and Mechanistic Implications," *J. Am. Chem Soc.*, 116:10403-10411 (1994).
Lin et al., "Fed-batch culture of a metabolically engineered *Escherichia coli* strain designed for high-level succinate production and yield under aerobic conditions," *Biotechnol. Bioeng.*, 90:775-779 (2005).
Low et al., "Mimicking somatic hypermutation: Affinity maturation of antibodies displayed on baceriophage using a bacterial mutator strain," *J. Mol. Biol.*, 260(3):359-368 (1996).

Lutz et al., "Creating multiple-crossover DNA libraries independent of sequence identity," *Proc. Natl. Acad. Sci. U.S.A.*, 98:11248-11253 (2001).
Lutz et al., "Rapid generation of incremental truncation libraries for protein engiering using α-phosphothioate nucleotides," *Nucleic Acids Res.*, 29:E16 (2001).
Mahadevan et al., "The effects of alternate optimal solutions in constraint-based genome-scale metabolic models," *Metab. Eng.*, 5(4):264-276 (2003).
Majewski et al., "Simple Constrained-Optimization View of Acete Overflow in *E. Coli*," *Biotechnol. Bioeng.*, 35(7):732-738 (1990).
Moon et al., "Metabolic engineering of *Escherichia coli* for the production of malic acid," *Biochem. Eng. J.*, 40(2):312-320 (2008).
Moresi et al., "Fumaric acid production from hydrolysates of starch-based substrates," *J. Chem. Technol. Biotechnol.*, 54(3):283-290 (1992).
Morsomme et al., "Single point mutations in various domains of a plant plasma membrane H+-ATPase expressed in *Saccharomyces cerevisiae* increase H+-pumping and permit yeast growth at low pH," *Embo. J.*, 15(20):5513-5526 (1996).
Muller et al., "Nucleotide exchange and excisiion technology (NExT) DNA shuffling; a robust method for DNA fragmentation and directed evolution," *Nucleic Acids Res.*, 33:e117 (2005).
Neidhardt et al., "*Escherichia coli* and *Salmonella*," *Cellular and Molecular Biology*, 2nd ed. 1996, Washington, D.C.: ASM Press. 2 v. (xx, 2822, lxxvi ).
Ness et al., "Synthetic shuffling expands functional protein diversity by allowing amino acids to recombine independently," *Nat. Biotechnol.*, 20:1251-1255 (2002).
Okino et al., "An effeicient succinic acid production process in a metabolically engineered Corynebacterium glutamicum strain," *Appl. Microbiol. Biotechnol.*, 81(3):459-464 (2008).
Ostermeier et al., "A Combinatorial approach to hybrid enzymes independent of DNA homology," *Nat. Biotechnol.*, 17:1205-1209 (1999).
Ostermeier et al., "Combinatorial protein engineering by incremental truncation," *Proc. Natl. Acad. Sci. U.S.A.*, 96:3562-3567 (1999).
Otten et al., "Directed evolution: selecting today's biocatalysts," *Biomol. Eng.*, 22:1-9 (2005).
Pharkya et al., "Exploring the overproduction of amino acids using the bilevel optimization framework OptKnock," *Biotechnol. Bioeng.*, 84(7):887-899 (2003).
Price et al., "Genome-scale models of microbial cells: evaluating the consequences of constraints," *Nat. Rev. Microbiol.*, 2(11):886-897 (2004).
Pritchard et al., "A general model of error-prone PCR," *J. Theor. Biol.*, 234:497-509 (2005).
Qi et al., "Functional expression of prokaryotic and eukaryotic genes in *Escherichia coli* for conversion of glucose to p-hydroxystyrene," *Metab. Eng.*, 9:268-276 (2007).
Rajpal et al., "A general method for greatly improving the affinity of antibodies by using combinatorial libraries," *Proc. Natl. Acad. Sci. U.S.A.*, 102:8466-8471 (2005).
Reetz et al., "Iterative saturation mutagenesis (ISM) for rapid directed evolution of functional enzymes," *Nat. Protoc.*, 2:891-903 (2007).
Reetz et al., "Directed Evolution of an Enantioselective Enzyme through Combinatorial Multiple-Cassette Mutagenesis," *Angew. Chem. Int. Ed. Engl.*, 40:3589-3591 (2001).
Reetz et al., "Iterative saturation mutagenesis on the basis of B factors as a strategy for incresing protein thermostability," *Angew. Chem. Int. Ed.*, 45:7745-7751 (2006).
Reidhaar-Olson et al., "Combinatorial cassette mutagenesis as a probe of the informational content of protein sequences," *Science*, 241:53-57 (1988).
Reidhaar-Olson et al., "Random mutagenesis of protein sequences using oligonucleotide cassettes," *Methods Enzymol.*, 208:564-586 (1991).
Rhodes et al., "Production of fumaric acid by *Rhizopus arrhuzus*," *Appl. Microbiol.*, 7:74-80 (1959).
Rhodes et al., "Production of Fumaric Acid in 20-Liter Fermentors," *Appl. Microbiol.*, 10(1)9-15 (1962).

(56) References Cited

OTHER PUBLICATIONS

Rodriguez et al., "Characterization of the p-Coumaric Acid Decarboxylase from Lactobacillus plantarium CECT 748T," *J. Agric. Food Chem.*, 56:3068-3072 (2008).
Saltzgaber-Muller et al., "Nuclear genes coding the yeast mitochondrial adenosine triphosphatase complex. Isolation of ATP2 coding the F1-ATPase β subunit," *J. Bio. Chem.*, 258(19):11465-11470 (1983).
Sambrook et al., *Molecular Cloning: A Laboratory Manual, Third Ed.*, Cold Spring Harbor Laboratory, New York (2001).
Sariaslani, "Development of a Combined biological and Chemical Process for Production of Industrial aromatics from Renewable Resources," *Annu. Rev. Microbiol.*, 61:51-69 (2007).
Sass et al., "Folding of fumarase during mitochondrial import determines its dual targeting in yeast," *J. Biol. Chem.*, 278(46):45109-45116 (2003).
Schilling et al., "Combining Pathway Analysis with Flux Balance Analysis for the Comprehensive Study of Metabolic Systems," *Biotechnol. Bioeng.*, 71(4):286-306 (2000-2001).
Schilling et al., "Theory for the Systematic Definition of Metabolic Pathways and Their Use in Interpreting Metabolic Function from a Pathway-Oriented Perspective," *J. Theor. Biol.*, 203(3):229-248 (2000).
Schilling et al., "Toward Metabolic Phenomics: Analysis of Genomic Data Using Flux Balances," *Biotechnol. Prog.*, 15(3):288-295 (1999).
Selifonova et al., "Rapid evolution of novel traits in microorganisms," *Appl. Environ. Microbiol.*, 67:3645-3649 (2001).
Sen et al., "Developments in directed evolution for improving enzyme functins," *Appl. Biochem. Biotechnol.*, 143:212-223 (2007).
Shao et al., "Random-priming in vitro recombination: an effective tool for directed evolution," *Nucleic Acids Res.*, 26:681-683 (1998).
Shibata et al., "Purification, characterization, and immunological properties of fumarase from *Euglena gracilis* var. *bacillaris*," *J. Bacteriol.*, 164(2):762-768 (1985).
Shingler et al., "Nucleotide sequence and functional analysis of the complete phenol/3,4-dimethylphenol catabolic pathway of *Pseudomonas* sp. strain CF600," *J. Bacteriol.*, 174(3):711-724 (1992).
Sieber et al., "Libraries of hybrid proteins from distantly related sequences," *Nat. Biotechnol.*, 19:456-460 (2001).
Stanley et al., "Expression and stereochemical and isotope effect studies of active 4-oxalocrotonate decarboxylase," *Biochemistry*, 39:718-726 (2000).
Stemmer, "DNA shuffling by random fragmentation and reassembly: in vitro recombination for molecular evolution," *Proc. Natl. Acad. Sci. U.S.A.*, 91:10747-10751 (1994).
Stemmer, "Rapid evolution of a protein in vitro by DNA shuffling," *Nature*, 370:389-391 (1994).
Stols et al., "Production of succinic acid through overexpression of NAD(+)-dependent malic enzyme in an *Escherichia coli* mutant," *Appl. Environ. Microbiol.*, 63(7):2695-2701 (1997).
Stols et al., "Expression of Ascaris suum malic enzyme in a mutant *Escherichia coli* allows production of succinic acid from glucose," *Appl. Biochem. Biotechnol.*, 63-65: 153-158 (1997).
Straathof et al., "Feasibility of acrylic acid production by fermentation," *Appl. Microbiol. Biotechnol.*, 67:727-734 (2005).
Takeo, "Existence and Properties of Two Malic Enzymes in *Escherichia coli* Especially of NAD-linked Enzyme," *J. Biochem.*, 66:379-387 (1969).
Tsao et al., "Production of multifunctional organic acids from renewable resources," *Adv. Biochem. Eng. Biotechnol.*, 65:243-280 (1999).
Tzagoloff et al., "PET genes of *Saccharomyces cerevisiae*," *Microbiol. Rev.*, 54(3):211-225 (1990).
Uchiyama et al., "Identification of the 4-Hydroxycinnamate Decarboxylase (PAD) Gene of *Klebsiella oxytoca*," *Biosci. Biotechnol. Biochem.*, 72: 116-123 (2008).
Vanrolleghem et al., "Validation of a Metabolic Network for *Saccharomyces cerevisiae* Using Mixed Substrate Studies," *Biotechnol. Prog.*, 12(4):434-448 (1996).
Varma et al., "Metabolic Flux Balancing: Basic Concepts, Scientific and Practical Use," *Biotechnology*, 12:994-998 (1994).
Vemuri et al., "Effects of growth mode and pyruvate carboxylase on succinic acid production by metabolically engineered strains of *Escherichia coli*," *Appl. Environ. Microbiol.*, 68(4):1715-1727 (2002).
Vemuri et al. "Succinate production in dual-phase *Escherichia coli* fermentations depends on the time of transition from aerobic to anaerobic conditions," *J. Ind. Microbiol. Biotechnol.*, 28:325-332 (2002).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27:e18 (1999).
Wach et al., PCR-based gene targeting in *Saccharomyces cerevisiae*, in Yeast Gene Analysis, M.F. Tuite, Editor. 1998 Academic Press, San Diego.
Willke et al., "Biotechnological production of itaconic acid," *Appl. Microbiol. Biotechnol.*, 56(3-4):289-295 (2001).
Wong et al., "Sequence saturation mutagenesis (SeSaM): a novel method for directed evolution," *Nucleic Acids Res.*, 32:e26 (2004).
Wong et al., "Sequence saturation mutagenesis with tunable mutation frequencies," *Anal. Biochem.*, 341:187-189 (2005).
Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3:74-82 (2008).
Zelle et al., "Malic acid production by *Saccharomyces cerevisiae*: engineering of pyruvate carboxylation, oxaloacetate reduction, and malate export," *Appl. Environ. Microbiol.*, 74(9):2766-2777 (2008).
Zhao et al., "Molecular evolution by staggered extension process (StEP) in vitro recombination," *Nat. Biotechnol.*, 16:258-261 (1998).
Zhou et al., "Comparison of fumaric acid production by Rhizopus oryzae using different neutralizing agents," *Bioproc. Biosyst. Eng.*, 25(3):179-181 (2002).
Zhou et al., "Mycelial pellet formation by Rhizopus oryzae ATCC 20344," *Appl. Biochem. Biotechnol.*, 84-86:779-789 (2000).

* cited by examiner

MICROORGANISMS AND METHODS FOR THE BIOSYNTHESIS OF FUMARATE, MALATE, AND ACRYLATE

This application is a continuation of U.S. Ser. No. 14/716,767 filed May 19, 2015, which is a continuation of U.S. Ser. No. 13/372,332 filed Feb. 13, 2012 (now U.S. Pat. No. 9,062,330), which is a continuation of U.S. Ser. No. 12/486,724 filed Jun. 17, 2009 (now U.S. Pat. No. 8,129,154), which claims the benefit of priority of U.S. Provisional Ser. No. 61/073,348, filed Jun. 17, 2008; U.S. Provisional Ser. No. 61/077,127, filed Jun. 30, 2008; and U.S. Provisional Ser. No. 61/088,628, filed Aug. 13, 2008, each of which is incorporated by reference in their entirety.

BACKGROUND

The present disclosure relates generally to the design of engineered organisms and, more specifically to organisms having selected genotypes for the production of fumarate, malate, and acrylate.

Fumaric acid is used in industrial processes as a raw material in a wide range of chemical syntheses. The presence of a double bond and two carboxyl groups in this compound facilitates its use in making polyesters and other polymers. Some of its industrial applications include manufacturing of synthetic resins and biodegradable polymers. It also finds widespread use as a food acidulant, a dietary supplement and as a beverage ingredient. Fumaric acid is currently derived from maleic anhydride, which is produced by the catalytic oxidation of benzene or butene feedstocks. Even though fumaric acid is approximately 10% more expensive than maleic anhydride, the non-toxic nature of the former and the special properties, such as greater hardness, that it imparts to the polymer structure makes it a good option for polymer industry as compared to maleic anhydride. Recently, two new applications for fumaric acid have been developed: (i) it can be used medicinally for treating a skin condition called psoriasis, and (ii) it can be used as a supplement for cattle feed.

Malic acid is used as an acidulant and taste enhancer in the beverage and food industry. Racemic malic acid is synthesized petrochemically from maleic anhydride whereas enantiometrically pure L-malic acid (used in pharmaceutical production) is produced from fumarate by hydration with fumarase.

Acrylic acid is a large volume petrochemical product. For example, acrylic acid is a commodity monomer intermediate used for the production of polymeric materials such polyacrylic acid, which is a major component of superabsorbant diapers. Acrylic acid also is used for the production of acrylate esters, which are utilized in water-soluble latex coatings, adhesives and inks. Acrylic acid and acrylate esters are manufactured by petrochemical processes such as oxidation of propylene, followed by esterification with alcohols such as methanol, butanol, and 2-ethylhexanol.

Chemicals manufactured from petroleum feedstocks suffer the burden of high and volatile prices, insecure foreign supply chains, and declining reserves (Frost, J. W., Redefining chemical manufacture. *Ind. Biotechnol.* 1:23-24 (2005)). Therefore, a method of producing large volume chemicals or their intermediates by alternative means that reduce petroleum-based processes and also use less energy- and capital-intensive processes would be beneficial.

Thus, there is a need to gain access to microorganisms having the commercially valuable characteristics of efficiently biosynthesizing fumarate, malate, and acrylate in high yields. The present invention satisfies this need and provides related advantages as well.

SUMMARY OF THE INVENTION

In some embodiments, the present invention provides a non-naturally occurring microbial organism that includes one or more gene disruptions occurring in genes encoding enzymes selected from the group of fumarate reductase (FRD), alcohol dehydrogenase (ADHEr) and lactate dehydrogenase (LDH_D) such that the one or more gene disruptions confers increased production of fumarate onto said non-naturally occurring microbial organism.

In some embodiments, the present invention provides a method for producing fumaric acid that includes culturing a non-naturally occurring microbial organism having one or more gene disruptions occurring in genes encoding enzymes selected from the group of fumarate reductase (FRD), alcohol dehydrogenase (ADHEr) and lactate dehydrogenase (LDH_D) such that the one or more gene disruptions confers increased production of fumarate onto said non-naturally occurring microbial organism.

In some embodiments, the present invention provides a non-naturally occurring microbial organism that includes one or more gene disruptions occurring in genes encoding enzymes selected from a group of fumarate reducatse (FRD), alcohol dehydrogenase (ADHEr), fumarase (FUM) and lactate dehydrogenase (LDH_D), when the gene disruption reduces an activity of the enzyme it confers increased production of malate onto said non-naturally occurring microbial organism.

In some embodiments, the present invention provides a method for producing malic acid that includes culturing a non-naturally occurring microbial organism having one or more gene disruptions occurring in genes encoding enzymes selected from a group of fumarate reducatse (FRD), alcohol dehydrogenase (ADHEr), fumarase (FUM) and lactate dehydrogenase (LDH_D), when the gene disruption reduces an activity of the enzyme it confers increased production of malate onto said non-naturally occurring microbial organism.

In some embodiments, the present invention provides a non-naturally occurring eukaryotic organism, comprising one or more gene disruptions occurring in genes encoding enzymes imparting increased fumarate production in the organism when the gene disruption reduces an activity of the enzyme, whereby the one or more gene disruptions confers increased production of fumarate onto the organism.

In some embodiments, the present invention provides a method for producing fumaric acid that includes culturing a non-naturally occurring eukaryotic organism having one or more gene disruptions occurring in genes encoding an enzyme providing increased fumarate production in the organism when the gene disruption reduces an activity of the enzyme, whereby the one or more gene disruptions confers increased production of fumarate onto the organism.

In some embodiments, the present invention provides a non-naturally occurring eukaryotic organism that includes one or more gene disruptions occurring in genes encoding enzymes imparting increased malate production in the organism when the gene disruption reduces an activity of the enzyme, whereby the one or more gene disruptions confers enhanced production of malate onto the organism.

In some embodiments, the present invention provides a method for producing malic acid that includes culturing a non-naturally occurring eukaryotic organism having one or more gene disruptions occurring in genes encoding enzymes imparting increased malate production to the organism when the gene disruption reduces an activity of the enzyme, whereby the one or more gene disruptions confers increased production of malate onto the organism.

In some embodiments, the present invention provides a non-naturally occurring eukaryotic organism that includes one or more gene disruptions occurring in genes encoding enzymes imparting increased acrylate production in the organism when the gene disruption reduces an activity of the enzyme, whereby the one or more gene disruptions confers increased production of acrylate onto the organism.

In some embodiments, the present invention provides a method for producing acrylic acid that includes culturing a non-naturally occurring eukaryotic organism having one or more gene disruptions occurring in genes encoding enzymes imparting enhanced acrylate production in the organism when the gene disruption reduces an activity of the enzyme, whereby the one or more gene disruptions confers increased production of acrlyate onto the organism.

In some embodiments, the present invention provides a non-naturally occurring microbial organism that includes a microbial organism having an olefin pathway having at least one exogenous nucleic acid encoding an olefin pathway enzyme expressed in a sufficient amount to produce an olefin, the olefin pathway including a decarboxylase.

In some embodiments, the present invention provides a method for producing an olefin that includes culturing a non-naturally occurring microbial organism having an olefin pathway that includes at least one exogenous nucleic acid encoding an olefin pathway enzyme expressed in a sufficient amount to produce an olefin under conditions and for a sufficient period of time to produce an olefin, the olefin pathway including a decarboxylase.

In some embodiments, the present invention provides a non-naturally occurring microbial organism that includes a microbial organism having an acrylate pathway having at least one exogenous nucleic acid encoding an acrylate pathway enzyme expressed in a sufficient amount to produce acrylate, the acrylate pathway including a decarboxylase.

In some embodiments, the present invention provides a method for producing acrylate that includes culturing a non-naturally occurring microbial organism having an acrylate pathway, the pathway includes at least one exogenous nucleic acid encoding an acrylate pathway enzyme expressed in a sufficient amount to produce acrylate under conditions and for a sufficient period of time to produce acrylate, the acrylate pathway including a decarboxylase.

In some embodiments, the present invention provides a method for producing acrylate that includes a) culturing a first non-naturally occurring microbial organism that includes one or more gene disruptions occurring in one or more genes encoding one or more enzymes that enhance fumarate production toin the organism when the one or more genes disruptions reduces an activity of the one or more enzymes, whereby the one or more gene disruptions confers increased production of fumarate onto the non-naturally occurring organism, and b) adding a decarboxylase to the cultured first non-naturally occurring microbial organism, the decarboxylase catalyzing the decarboxylation of fumarate.

BRIEF DESCRIPTION OF THE DRAWINGS

FIG. 10, light gray; FIG. 11 dark gray, dashed; and and FIG. 12 light gray, dashed, compared with each other and with the production characteristics of the wild-type *S. cerevisiae* network (black). Note the reduction in feasible solution space as additional deletions are imposed on the network.

DETAILED DESCRIPTION OF THE INVENTION

Figure 1:
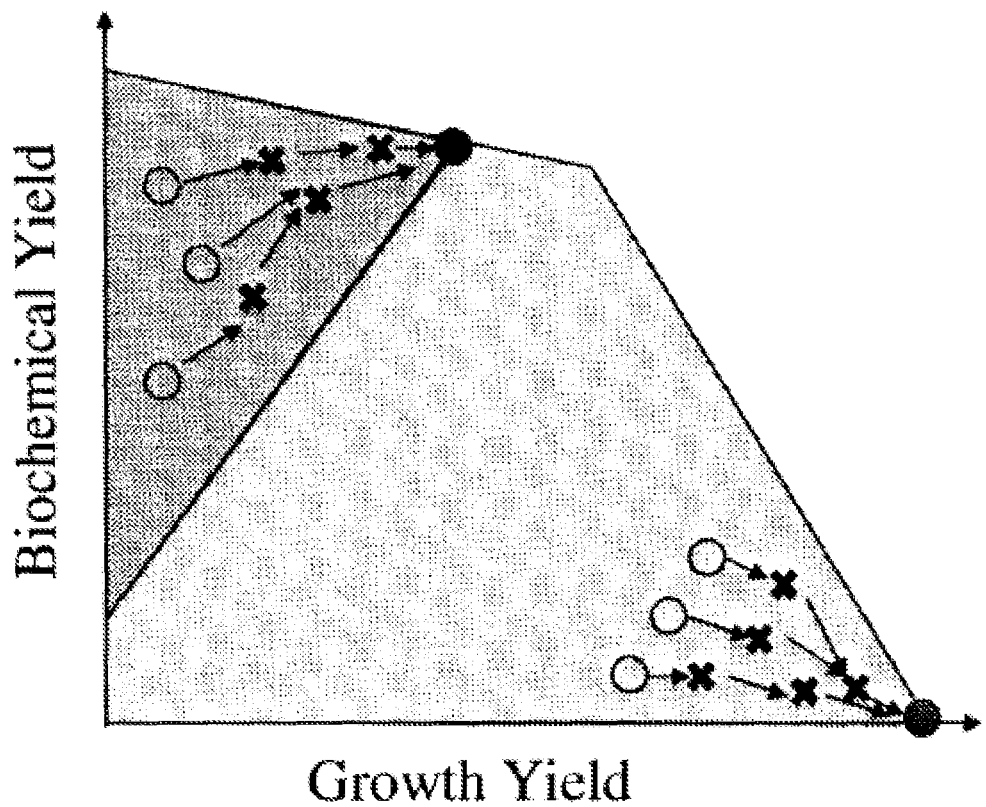
FIG. 1 shows the hypothetical production envelopes of an OptKnock-designed strain contrasted against a typical non-growth-coupled production strain. Note that the potential evolutionary trajectories of the OptKnock strain are fundamentally different in that they will lead to a high producing phenotype.

This invention is directed, in part, to engineered organisms having biosynthetic pathways to fumarate, malate, and acrylate. In some embodiments, the invention utilizes optimization-based approaches based on in silico stoichiometric models of *Escherichia coli* and *Saccharomyces cerevisiae* metabolism that identify metabolic designs for increased production of fumarate, malate, and acrylate in these organisms. A bilevel programming framework, OptKnock, is applied within an iterative algorithm to predict multiple sets of gene disruptions, that collectively result in increased production of fumarate, malate, or acrylate. As disclosed herein, various combinations of gene deletions or functional disruptions of genes significantly improve the fumarate, malate, or acrylate production capabilities of *E. coli* and *S. cerevisiae*.

Production of acrylate, in particular, involves not only primary metabolic production of fumarate, but also subsequent mono-decarboxylation. Thus, the invention is also directed, in part, to a developing a route to acrylate from fumarate by reaction with a decarboxylase enzyme. The decarboxylase enzyme can be introduced as an exogenous nucleic acid into the same organism that has been engineered for increased fumarate production via gene disruptions, or alternatively through a secondary transformation involving extracellular addition of a decarboxylase to a culture containing over-produced fumarate. Another alternative is to provide a second organism having decarboxylase activity. In such a case, the fumarate-producing organism can be co-cultured or serially cultured with the second organism possessing the requisite decarboxylase.

The engineering designs are equally applicable if an organism other than *E. coli* or *S. cerevisiae* is chosen as the production host, even if the organism naturally lacks the activity or exhibits low activity of a subset of the gene products marked for disruption. In those cases, disruptions must only be introduced to eliminate or lessen the enzymatic activities of the gene products that are naturally present in the chosen production host. Production of fumarate, malate, or acrylate for the in silico designs are confirmed by construction of strains having the designed metabolic genotype. These metabolically engineered cells or organisms can also be subjected to adaptive evolution to further augment product production.

In a further embodiment, the invention is directed to an integrated computational and engineering platform for developing metabolically altered microorganism strains having enhanced fumarate, malate, or acrylate producing characteristics. Strains identified via the computational component of the platform are put into actual production by genetically engineering the predicted metabolic alterations which lead to the enhanced production of fumarate, malate, or acrylate. Production of the desired product is optionally coupled to optimal growth of the microorganism. Strains exhibiting increased production of these products can be further subjected to adaptive evolution to further augment product biosynthesis. The levels of product production following adaptive evolution also can be predicted by the computational component of the system where, in this specific embodiment, the elevated product levels are realized following evolution.

Currently, the only organisms known to produce fumarate at a reasonable level are *Rhizopus* (Tsao et al., *Adv. Biochem. Eng. Biotechnol.*, 65:243-280 (1999); Lee et al., *Macromolecular Bioscience*, 4:157-164 (1999); Rhodes et al., *Appl. Microbiol.* 1962, 10(1):9-15; and Rhodes et al., *Appl. Microbiol.* 7(2):74-80 (1959)). Fumarate production in these organisms utilizes pyruvate carboxylase to fix carbon dioxide, converting pyruvate into oxaloacetate (Kenealy et al., *Appl. Environ. Microbiol.* 52(1):128-133 (1986)). This is subsequently converted into malate and finally into fumarate. Some reports on fumarate production in *Rhizopus* have outlined fermentation and culture conditions for obtaining fumarate (Moresi et al., *J. Chem. Technol. Biotechnol.* 54(3):283-2890 (1992)). Optimum concentrations of metal ions and phosphate have been determined to maximize the fumarate production during the fermentation process (Zhou et al., *Appl. Biochem. Biotechnol.* 84-86:779-89 (2000)). Another study examined various cassava bagasse hydrolysates as a cheap carbon source, reporting a yield of 22 g/L of fumarate (Carta et al., *Bioresource Technology* 68(1):23-28 (1999)). A study of neutralizing agents for fumarate production was also undertaken. It was determined that utilizing $CaCO_3$ provides the highest fumaric acid weight yield (53.4%) and volumetric productivity (1.03 g/L·hr) (Zhou et al., *Bioprocess Biosyst. Eng.* 25(3):179-181 (2002)).

However, growing mycelia often form interlocking hyphae mingled with calcium carbonate, resulting in oxygen transfer limitations, thus slowing down the rate of fermentation. Another difficulty involved in fumarate production is the tendency of *Rhizopus* sporangiospores to grow into mycelial mats or mycelial lumps (Zhou et al., *Appl. Biochem. Biotechnol.* 84-86:779-89 (2000)), interfering with the function of bafflers and propellers inside a reactor. A rotary biofilm contactor has been utilized in a simultaneous fermentation-adsorption process to obtain yields of 85 g/L of fumarate from 100 g/L of glucose. Finally, *R. arrhizus* NRR11526 immoblized on a polyurethane sponge was used to facilitate continuous fermentation for fumarate production. Yields of approximately 12.3 g/L of fumaric acid were obtained in this work (Lee et al., *Macromolecular Bioscience* 4:157-164 (2004)). However, despite the above efforts, the approaches employed have several drawbacks which hinder applicability in commercial settings. Chemical processes remain predominantly used in fumarate production because of (a) the cost benefits of chemical production and (b) the complications associated with maintaining the right size of mycelial particles for fumarate production.

Malic acid production has been reported in a wide range of organisms, including both yeast and bacteria (Jantama, K., et al., *Biotechnol Bioeng*, 99(5):1140-53 (2008); Moon, S. Y., et al., *Biochemical Engineering Journal* (2008).). Most recently, malic acid titers of up to 59 g/L with yields of 0.42 mol/mol glucose were reported in *Saccharomyces cerevisiae*. (Zelle, R. M., et al., *Appl Environ Microbiol*, 74(9):2766-77 (2008)). This level of malic acid production was achieved by introducing three genetic modifications: (i) overexpression of the native pyruvate carboxylase, (ii) increasing the expression of malate dehydrogenase and retargeting it to cytosol, and (iii) functional expression of a heterologous malate transporter gene. Other yeasts in which malic acid has been produced successfully include *Aspergillus flavus, Rhizopus arrhizus*, and *Zygosaccharomyces rouxii*. (Zelle, R. M., et al., *Appl Environ Microbiol*, 74(9): 2766-77 (2008)). The highest malic acid titer has been reported in *A. flavus* (113 g/L) with malic acid yield at 63% of the maximum theoretical yield on glucose. However, potential aflatoxin production has rendered this organism unusable for the production of food-grade malic acid. Malic acid yields with other yeasts are not high enough to pursue commercial production. (Zelle, R. M., et al., *Appl Environ Microbiol*, 74(9):2766-77 (2008)). Relatively higher malate yields have been reported in a mutant strain of *Escherichia coli* C (1.4 mol/mol glucose) which was engineered to inhibit secretion of byproducts such as acetate, lactate, formate, and ethanol. (Jantama, K., et al., *Biotechnol Bioeng*, 99(5):1140-53 (2008)).

This invention is also directed, in part, to methods for producing olefins by decarboxylation an alpha, beta-unsaturated carboxylic acids as exemplified in FIG. 19*a*. The unsaturated carboxylic acid substrate can be of any structural olefin geometry. For example the unsaturated carboxylic acid may be substituted at either the alpha or beta position. Additionally, beta-substituted unsaturated carboxylic acid substrates can have either E or Z olefin geometry. The product will typically be a terminal olefin. Furthermore, the carboxylic acid substrate can be further conjugated as shown in FIG. 19*b*, wherein pentadienoic acid is decarboxylated to the commercially valuable commodity chemical 1,3-butadiene. 1,3-butadiene is an important chemical in the manufacture of synthetic rubbers, for example.

Figure 20:
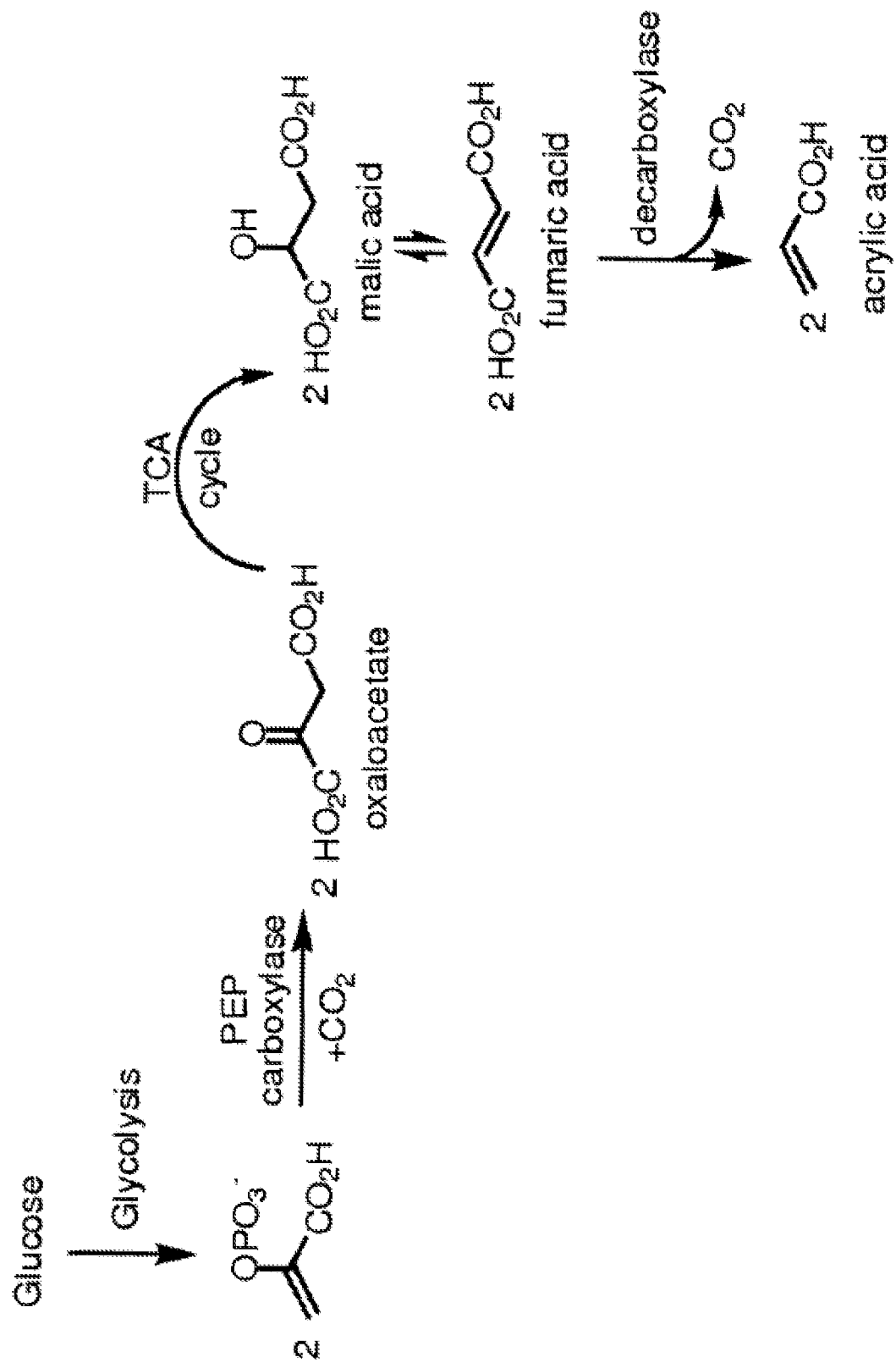
FIG. 20 shows a biosynthetic pathway for the direct production of acrylate through decarboxylation of fumarate.

In some embodiments this invention is directed to methods of producing acrylic acid involving primary metabolic production of fumaric acid, followed by decarboxylation. FIG. 20 shows a biosynthetic scheme for producing acrylic acid which involves treatment of fumaric acid with a decarboxylase enzyme in a pathway leading directly to acrylate, or alternatively through a secondary transformation involving extracellular addition of a decarboxylase to a culture containing over-produced fumarate.

As shown in FIG. 20, two moles of acrylic acid are produced from each mole of glucose consumed and carbon is utilized in a very efficient manner. Carbon from 1 mole of glucose provides two moles of phosphoenol pyruvate (PEP) through glycolysis, which then reacts with carbon dioxide (via PEP carboxylase or PEP caboxykinase) to afford a maximum theoretical yield of 2.0 moles of fumaric acid, which upon decarboxylation leads to two moles of acrylic acid. This efficient use of carbon is important for achieving high yields (0.8 g acrylic acid/g glucose) and favorable process economics in the production of acrylic acid from renewable feedstocks. In addition, although the final decarboxylation step leads to release of carbon dioxide, the conversion of phosphoenolpyruvate to oxaloacetate actually consumes one mole of carbon dioxide, leading to an overall process that is $CO_2$ neutral. The decarboxylation of fumarate to acrylate also will drive the equilibrium between malate and fumarate, thus leading to all carbon being funneled to the desired acrylic acid product.

Production of acrylic acid by fermentation involving renewable feedstocks has been investigated previously, and several designs have been proposed (Straathof, A. J. et al., *Appl. Microbiol. Biotechnol.*, 67:727-34 (2005)). In particular, processes involving conversion of lactate or lactoyl-CoA to acrylate or acryloyl-CoA have been explored, but suffer from unfavorable thermodynamics and undesirably high levels of lactate secretion. Another bioprocess for acrylic acid production proceeds through the intermediate 3-hydroxypropionic acid (3-HP), which is produced first by fermentation and then isolated and dehydrated in a second step under anhydrous conditions (Cameron, D. C. and P. F. Suthers WO0242418).

Such two-step routes to acrylic acid via 3-HP have presented challenges and are still under development. Direct conversion of biomass-derived sugars to acrylic acid is highly desirable due to substantial economic benefits associated with reduction in capital and energy costs relative to multi-step processes.

The maximum theoretical yield of each of the acid products described herein is 2 moles per mole of glucose consumed (see equations 1-3 below), indicating a significant potential for improving the existing biochemical processes further.

$$C_6H_{12}O_6 + 2CO_2 \rightarrow 2C_4H_4O_4 + 2H_2O \text{ (fumaric acid)} \qquad \text{equation 1}$$

$$C_6H_{12}O_6 + 2CO_2 \rightarrow 2C_4H_6O_5 \text{ (malic acid)} \qquad \text{equation 2}$$

$$C_6H_{12}O_6 \rightarrow 2C_3H_4O_2 + 2H_2O \text{ (acrylic acid)} \qquad \text{equation 3}$$

Many different substrates derived from renewable feedstocks, such as glucose, xylose, arabinose, sorbitol, sucrose, glycerol, or even synthesis gas (a mixture carbon monoxide, hydrogen and carbon dioxide), can serve as carbon and energy sources for a fermentation process. Each of these substrates can be used for biological production of fumarate, malate, or acrylate.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a cyclohexanone biosynthetic pathway.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation methods that inactivate the encoded gene product. One particularly useful method of gene disruption is complete gene deletion because it reduces or eliminates the occurrence of genetic reversions in the non-naturally occurring eukaryotic organisms of the invention. The term "gene disruption" is also intended to mean a genetic alteration that lowers the activity of a given gene product relative to its activity in a wild-type organism. This attenuation of activity can be due to, for example, a deletion in a portion of the gene which results in a truncated gene product or any of various mutation methods that render the encoded gene product less active than its natural form, replacement or mutation of the promoter sequence leading to lower or less efficient expression of the gene, culturing the organism under a condition where the gene is less highly expressed than under normal culture conditions, or introducing antisense RNA molecules that interact with complementary mRNA molecules of the gene and alter its expression.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein the term "parent decarboxylase" refers to both wild-type and previously engineered decarboxylases that serve as a starting point for further optimization of the decarboxylation activity. Optimizations can include not only changes made to the nucleic acid sequence encoding the decarboxylase, but also post-translational modifications to the enzyme product.

As used herein the terms "acrylate" and "acrylic acid" are used interchangeably. One skilled in the art will appreciate that the ionization state of a typical carboxylic acid will depend on the pH of its environment. For example, with a $pK_a$ of approximately 4, acrylic acid can be significantly in its ionized acrylate form when the pH is 6 or more. While the final isolated product of any given process can be acrylic acid, the direct product of fermentation will frequently be the corresponding acrylate salt, although this can vary depending on the pH conditions employed. In a similar manner, "fumarate" and "fumaric acid," "malate" and "malic acid," and "carboxylate" and "carboxylic acid" are used interchangeably.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having cyclohexanone biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% can represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16 2098) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism, that includes one or more gene disruptions. The disruptions occur in genes encoding an enzyme that is obligatory to coupling fumarate production to growth of the microorganism when the gene disruption reduces the activity of the enzyme, such that the gene disruptions confer stable growth-coupled production of fumarate onto the non-naturally occurring microorganism. In other embodiments, engineered organisms that include one or more gene disruptions can enhance non-growth coupled production fumarate by linking the production of fumarate to energy generation and/or redox balance.

In other embodiments, the disruptions occur in genes encoding an enzyme obligatory to coupling malate production to growth of the microorganism when the gene disruption reduces the activity of the enzyme, such that the gene disruptions confer stable growth-coupled production of malate onto the non-naturally occurring microorganism. Engineered organisms that include one or more gene disruptions can also enhance non-growth coupled production malate by linking the production of malate to energy generation and/or redox balance.

In other embodiments, the invention provides a non-naturally occurring microbial organism that includes one or more gene disruptions. The disruptions occur in genes encoding an enzyme obligatory to coupling acrylate production to growth of the microorganism when the gene disruption reduces the activity of the enzyme, such that the gene disruptions confer stable growth-coupled production of acrylate onto the non-naturally occurring microorganism. In other embodiments, engineered organisms that include one or more gene disruptions can also enhance non-growth coupled production acrylate by linking the production of acrylate to energy generation and/or redox balance.

In some embodiments, the invention provides a non-naturally occurring prokaryotic organism, that includes one or more gene disruptions. The disruptions occur in genes encoding an enzyme obligatory to coupling fumarate production to growth of the microorganism when the gene disruption reduces the activity of the enzyme, such that the gene disruptions confer stable growth-coupled production of fumarate onto the non-naturally occurring microorganism. In other embodiments, an engineered prokaryotic organism that includes one or more gene disruptions can also enhance non-growth coupled production fumarate by linking the production of fumarate to energy generation and/or redox balance.

In other embodiments, the invention provides a non-naturally occurring prokaryotic organism that includes one or more gene disruptions. The disruptions occur in genes encoding an enzyme obligatory to coupling malate production to growth of the microorganism when the gene disruption reduces the activity of the enzyme, such that the gene disruptions confer stable growth-coupled production of malate onto the non-naturally occurring microorganism. In other embodiments, an engineered prokaryotic organism that includes one or more gene disruptions can also enhance non-growth coupled production malate by linking the production of malate to energy generation and/or redox balance.

In still further embodiments, the invention provides a non-naturally occurring prokaryotic organism that includes one or more gene disruptions. The disruptions occur in genes encoding an enzyme obligatory to coupling acrylate production to growth of the organism when the gene disruption reduces the activity of the enzyme, such that the gene disruptions confer stable growth-coupled production of acrylate onto the non-naturally occurring organism. In other embodiments, an engineered prokaryotic organism that includes one or more gene disruptions can also enhance non-growth coupled production acrylate by linking the production of acrylate to energy generation and/or redox balance.

In some embodiments, the invention provides a non-naturally occurring eurakoytic organism, that includes one or more gene disruptions. The disruptions occur in genes encoding an enzyme obligatory to coupling fumarate production to growth of the organism when the gene disruption reduces the activity of the enzyme, such that the gene disruptions confer stable growth-coupled production of fumarate onto the non-naturally occurring organism. In other embodiments, an engineered eukaryotic organism that includes one or more gene disruptions can also enhance non-growth coupled production fumarate by linking the production of fumarate to energy generation and/or redox balance.

In other embodiments, the invention provides a non-naturally occurring eukaryotic organism that includes one or more gene disruptions. The disruptions occur in genes encoding an enzyme obligatory to coupling malate production to growth of the organism when the gene disruption reduces the activity of the enzyme, such that the gene disruptions confer stable growth-coupled production of malate onto the non-naturally occurring organism. In other embodiments, an engineered eukaryotic organism that includes one or more gene disruptions can also enhance non-growth coupled production malate by linking the production of malate to energy generation and/or redox balance.

In still further embodiments, the invention provides a non-naturally occurring eukaryotic organism that includes one or more gene disruptions. The disruptions occur in genes encoding an enzyme obligatory to coupling acrylate production to growth of the organism when the gene disruption reduces the activity of the enzyme, such that the gene disruptions confer stable growth-coupled production of acrylate onto the non-naturally occurring organism. In other embodiments, an engineered eukaryotic organism that includes one or more gene disruptions can also enhance non-growth coupled production acrylate by linking the production of acrylate to energy generation and/or redox balance.

Further, the present invention provides methods of producing such non-naturally prokaryotic or eukaryotic organisms having stable growth-coupled production of fumarate, malate, or acrylate. For fumarate production, for example, the method includes: (a) identifying in silico a set of metabolic modifications requiring fumarate production during cell growth, and (b) genetically modifying a microorganism to contain the set of metabolic modifications requiring fumarate production.

The engineered organisms described herein are useful not only for enhancing growth-coupled production, but they are also well-suited for enhancing non-growth coupled production because they link the production of fumarate, malate and/or acrylate to energy generation and/or redox balance. Exemplary non-growth coupled production methods include implementing an aerobic growth phase followed by an anaerobic production phase. For example, Vemuri et al. *J. Ind. Microbiol. Biotechnol.*, 6:325-332, (2002) describe a dual-phase process for the production of succinate in *E. Coli*. A similar non-growth couple production process in a strain of *Corynebacterium glutamicum* has been described (Okino et al., *Appl. Microbiol. Biotechnol.* 81:459-464 (2008)).

Another such method involves withholding an essential nutrient from a propagated cell culture, thereby limiting growth, but not precluding production as described in Durner et al., *Appl. Environ. Microbiol.* 8:3408-3414(2000). Yet another strategy aimed at decoupling growth from production involves replacing the growth substrate with another compound that is more slowly metabolizable as described in Altamirano et al., *Biotechnol. Bioeng.* 76:351-360 (2001). Growth decoupled-product formation can also be brought about by specific genetic modifications as described in Blombach et al. *Appl. Microbiol. Biotechnol.* 79:471-479 (2008).

One computational method for identifying and designing metabolic alterations favoring growth-coupled production of a product is the OptKnock computational framework, Burgard et al., *Biotechnol Bioeng,* 84:647-657 (2003). OptKnock is a metabolic modeling and simulation program that suggests gene disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production.

The concept of growth-coupled biochemical production can be visualized in the context of the biochemical production envelopes of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. Although exceptions exist, typically the production of a desired biochemical is in direct competition with biomass formation for intracellular resources. Thus, enhanced rates of biochemical production will necessarily result in sub-maximal growth rates. The knockouts suggested by OptKnock are designed to restrict the allowable solution boundaries forcing a change in metabolic behavior from the wild-type strain as depicted in FIG. 1. Although the actual solution boundaries for a given strain will expand or contract as the substrate uptake rate(s) increase or decrease, each experimental point should lie within its calculated solution boundary. Plots such as these enable one to visualize how close strains are to their performance limits or, in other words, how much room is available for improvement. The OptKnock framework has already been able to identify promising gene deletion strategies for biochemical overproduction, (Burgard et al., *Biotechnol Bioeng,* 84:647-657 (2003); Pharkya et al., *Biotechnol Bioeng,* 84:887-899 (2003)) and establishes a systematic framework that will naturally encompass future improvements in metabolic and regulatory modeling frameworks. Lastly, when complete gene deletions are constructed there is a negligible possibility of the designed strains reverting to their wild-type states because the genes selected by OptKnock are completely removed from the genome.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. patent application Ser. No. 10/043,440, filed Jan. 10, 2002, and in International Patent No. PCT/US02/00660, filed Jan. 10, 2002.

Another computational method for identifying and designing metabolic alterations favoring growth-coupled production of a product is metabolic modeling and simulation system termed SimPheny®. This computational method and system is described in, for example, U.S. patent application Ser. No. 10/173,547, filed Jun. 14, 2002, and in International Patent Application No. PCT/US03/18838, filed Jun. 13, 2003.

SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *S. cerevisiae* on a variety of single-carbon sources as well as the metabolism of *H. influenzae* as described in Edwards and Palsson, *Proc. Natl. Acad. Sci.* 97:5528-5533 (2000), *Edwards and Palsson, J.*

Bio. Chem. 274:17410-17416 (1999) and Edwards et al., Nature Biotech. 19:125-130 (2001).

Once the solution space has been defined, it can be analyzed to determine possible solutions under various conditions. This computational approach is consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement growth-coupled production of a biochemical product. Such metabolic modeling and simulation methods include, for example, the computational systems exemplified above as SimPheny® and OptKnock. For simplicity in illustrating the invention, the methods and strains will be described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The ability of a cell or organism to obligatory couple growth to the production of a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. As shown in FIG. 1, the production of a desired biochemical generally is in direct competition with biomass formation for intracellular resources. Under these circumstances, enhanced rates of biochemical production will necessarily result in sub-maximal growth rates. The knockouts suggested by the above metabolic modeling and simulation programs such as OptKnock are designed to restrict the allowable solution boundaries forcing a change in metabolic behavior from the wild-type strain as depicted in FIG. 1. Although the actual solution boundaries for a given strain will expand or contract as the substrate uptake rate(s) increase or decrease, each experimental point will lie within its calculated solution boundary. Plots such as these enable accurate predictions of how close the designed strains are to their performance limits which also indicates how much room is available for improvement.

The OptKnock mathematical framework is exemplified herein for pinpointing gene deletions leading to growth-coupled biochemical production as illustrated in FIG. 1. The procedure builds upon constraint-based metabolic modeling which narrows the range of possible phenotypes that a cellular system can display through the successive imposition of governing physico-chemical constraints, Price et al., Nat Rev Microbiol, 2: 886-97 (2004). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1, \ldots, N\}$ of metabolites and a set $M=\{1, \ldots, M\}$ of metabolic reactions is expressed mathematically as follows:

$$\text{maximize } v_{cellular\ objective}$$

$$\text{subject to } \sum_{j=1}^{M} S_{ij} v_j = 0, \quad \forall i \in N$$

$$v_{substrate} = v_{substrate\_uptake} \text{ mmol/gDW} \cdot \text{hr} \quad \forall i \in \{\text{limiting substrate(s)}\}$$

$$v_{atp} \geq v_{atp\_main} \text{ mmol/gDW} \cdot \text{hr}$$

$$v_j \geq 0, \quad \forall j \in \{irrev.\ \text{reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., 2nd ed. 1996, Washington, D.C.: ASM Press. 2 v. (xx, 2822, 1xxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., Biotechnol Bioeng, 74: 364-375 (2001), Burgard et al., Biotechnol Prog, 17: 791-797 (2001). These binary variables, $$y_j = \begin{cases} 1, & \text{if reaction flux } v_j \text{ is active} \\ 0, & \text{if reaction flux } v_j \text{ is not active} \end{cases},$$

$$\forall j \in M$$

assume a value of 1 if reaction j is active and a value of 0 if it is inactive. The following constraint, $$v_j^{min} \cdot y_j \leq v_j \leq v_j^{max} \cdot y_j, \forall j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., Metab Eng, 5: 264-76 (2003).

Figure 2:
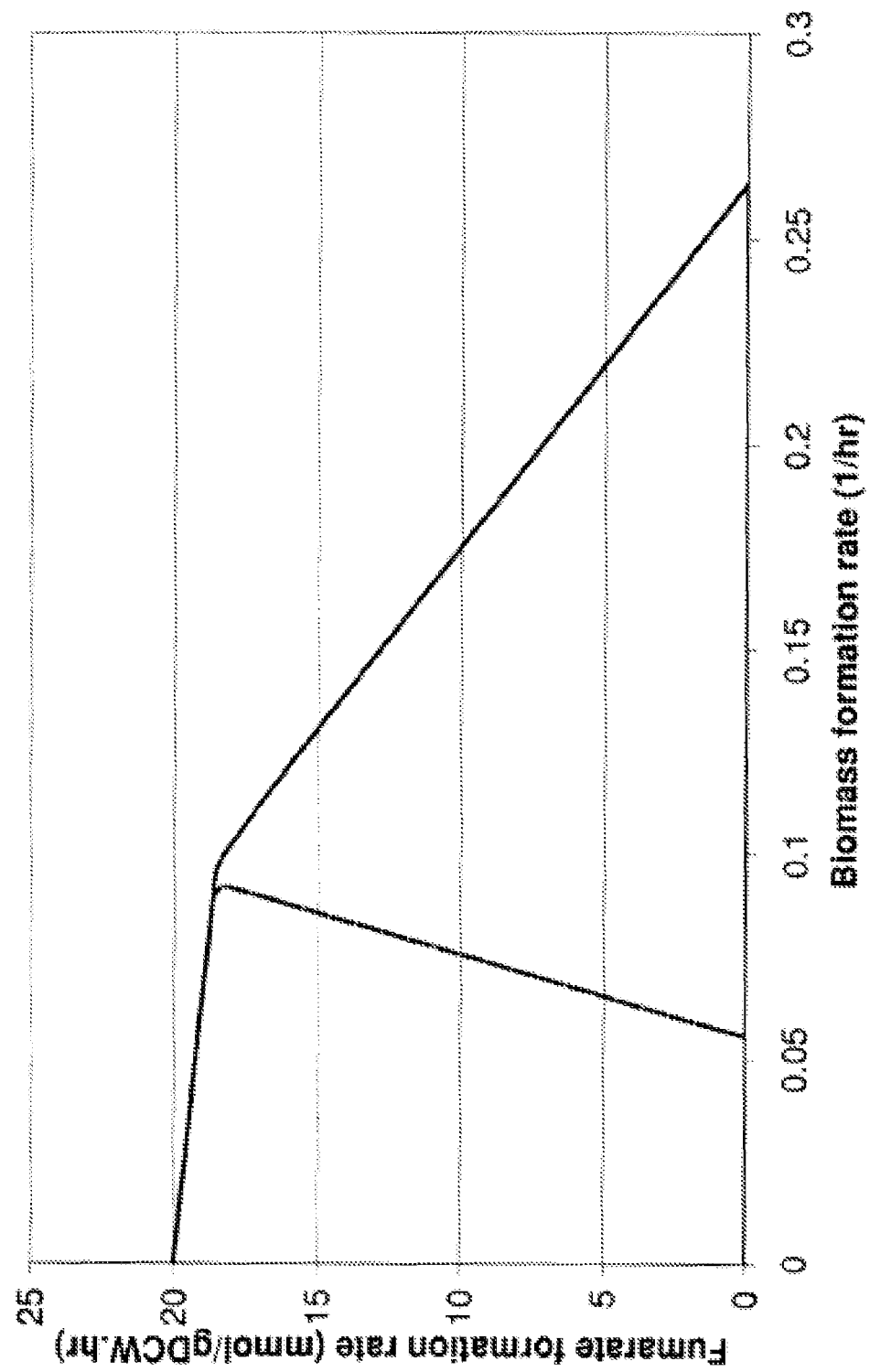
FIG. 2 shows increased fumarate production characteristics of one strain (black, dashed) compared with those of the wild-type *E. coli* network (black). At the maximum rate of growth, the wild-type network is not expected to form any fumarate.

Optimal gene/reaction knockouts are identified by solving a bilevel optimization problem that chooses the set of active reactions ($y_j=1$) such that an optimal growth solution for the resulting network overproduces the chemical of interest. Schematically, this bilevel optimization problem is illustrated in FIG. 2. Mathematically, this bilevel optimization problem is expressed as the following bilevel mixed-integer optimization problem:

$$\begin{aligned}
&\underset{y_j}{\text{maximize}}\; v_{chemical}\; (OptKnock)\\
&\left(\begin{array}{ll}
\text{subject to maximize } v_{biomass}\\
\quad\quad\quad\quad\quad v_j\\
\text{subject to } \sum_{j=1}^{M} S_{ij} v_j = 0, & \forall\, i \in N\\
v_{substrate} = v_{substrate\_uptake} & \forall\, i \in \{\text{limiting substrate(s)}\}\\
v_{atp} \geq v_{atp\_main}\\
v_{biomass} \geq v_{biomass}^{target}
\end{array}\right)\\
&v_j^{min}\cdot y_j \leq v_j \leq v_j^{max}\cdot y_j,\; \forall\, j \in M\\
&\sum_{j\in M^{forward}} (1-y_j) = K\\
&y_j \in \{0,1\},\; \forall\, j \in M
\end{aligned}$$

where $v_{chemical}$ is the production of the desired target product, for example fumarate or other biochemical product, and K is the number of allowable knockouts. Note that setting K equal to zero returns the maximum biomass solution of the complete network, while setting K equal to one identifies the single gene/reaction knockout ($y_j$=0) such that the resulting network involves the maximum overproduction given its maximum biomass yield. The final constraint ensures that the resulting network meets a minimum biomass yield. Burgard et al., *Biotechnol Bioeng*, 84: 647-57 (2003), provide a more detailed description of the model formulation and solution procedure. Problems containing hundreds of binary variables can be solved in the order of minutes to hours using CPLEX 8.0, *GAMS: The Solver Manuals*. 2003: GAMS Development Corporation, accessed via the GAMS, Brooke et al., *GAMS Development Corporation* (1998), modeling environment on an IBM RS6000-270 workstation. The OptKnock framework has already been able to identify promising gene deletion strategies for biochemical overproduction, Burgard et al., *Biotechnol Bioeng*, 84: 647-57 (2003), Pharkya et al., *Biotechnol Bioeng*, 84: 887-899 (2003), and establishes a systematic framework that will naturally encompass future improvements in metabolic and regulatory modeling frameworks.

Any solution of the above described bilevel OptKnock problem will provide one set of metabolic reactions to disrupt. Elimination of each reaction within the set or metabolic modification can result in fumarate as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve increased fumarate, malate, or acrylate production are implemented in the target cell or organism by functional disruption of at least one gene encoding each metabolic reaction within the set. As described previously, one particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the product coupling are desired or when genetic reversion is less likely to occur.

To identify additional productive solutions to the above described bilevel OptKnock problem which lead to further sets of reactions to disrupt or metabolic modifications that can result in the growth-coupled production of fumarate, malate, acrylate, or other biochemical products, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatory couples product biosynthesis to growth. For example, if a previously identified growth-coupled metabolic modification specifies reactions 1, 2, and 3 for disruption, then the following constraint prevents the same reactions from being simultaneously considered in subsequent solutions: $y_1+y_2+y_3 \geq 1$. The integer cut method is well known in the art and can be found described in, for example, reference, Burgard et al., *Biotechnol Prog*, 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny.

Constraints of the above form preclude identification of larger reaction sets that include previously identified sets. For example, employing the integer cut optimization method above in a further iteration would preclude identifying a quadruple reaction set that specified reactions 1, 2, and 3 for disruption since these reactions had been previously identified. To ensure identification of all possible reaction sets leading to growth-coupled production of a product, a modification of the integer cut method was employed.

Briefly, the modified integer cut procedure begins with iteration 'zero' which calculates the maximum production of the desired biochemical at optimal growth for a wild-type network. This calculation corresponds to an OptKnock solution with K equaling 0. Next, single knockouts are considered and the two parameter sets, $objstore_{iter}$ and $ystore_{iter,j}$, are introduced to store the objective function ($v_{chemical}$) and reaction on-off information ($y_j$), respectively, at each iteration, iter. The following constraints are then successively added to the OptKnock formulation at each iteration.

$$v_{chemical} \geq objstore_{iter} + \varepsilon - M\cdot\Sigma_{j\in ystore_{iter,j}=0} y_j$$

In the above equation, ε and M are a small and a large numbers, respectively. In general, ε can be set at about 0.01 and M can be set at about 1000. However, numbers smaller and/or larger then these numbers also can be used. M ensures that the constraint can be binding only for previously identified knockout strategies, while ε ensures that adding knockouts to a previously identified strategy must lead to an increase of at least ε in biochemical production at optimal growth. The approach moves onto double deletions whenever a single deletion strategy fails to improve upon the wild-type strain. Triple deletions are then considered when no double deletion strategy improves upon the wild-type strain, and so on. The end result is a ranked list, represented as desired biochemical production at optimal growth, of distinct deletion strategies that differ from each other by at least one knockout. This optimization procedure as well as the identification of a wide variety of reaction sets that, when disrupted, lead to increased production of a biochemical product are exemplified in detail further below. Given the teachings and guidance provided herein, those skilled in the art will understand that the methods and metabolic engineering designs exemplified herein are applicable to linking cell or microorganism growth to any biochemical product.

Employing the methods exemplified above, one can construct cells and organisms that obligatorily couple the production of a target biochemical product to growth of the cell or organism engineered to harbor the identified genetic alterations. In this regard, metabolic alterations have been identified that obligatorily couple the production of fumarate, malate, or acrylate to organism growth. Prokaryotic or eukaryotic organism strains constructed with the identified metabolic alterations produce elevated levels of fumarate, malate, or acrylate during the exponential growth phase. These strains can be beneficially used for the commercial production of fumarate, malate, or acrylate in continuous fermentation process without being subjected to the negative selective pressures described previously.

As described above, the metabolic alterations also enable non-growth coupled production of fumarate, malate, or acrylate. The invention is described herein with general reference to the metabolic reaction, reactant or product thereof, or with specific reference to one or more genes associated with the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene also constitutes a reference to the corresponding encoded enzyme and the reaction it catalyzes as well as the reactants and products of the reaction.

The methods of the invention provide a set of metabolic modifications that are identified by an in silico method selected from OptKnock. The set of metabolic modifications can include functional disruption of one or more metabolic reactions including, for example, disruption by gene deletion. Exemplary reactions, reaction nomenclature, reactants, products, cofactors and genes encoding enzymes catalyzing a reaction involved in the growth-coupled production of fumarate and malate in E. Coli are set forth in Tables 1, 2, 3, and 4.

The invention provides non naturally occurring microorganisms having increased production of fumarate or malate. Fumarate or malate production can be obligatorily linked to the exponential growth phase of the microorganism by genetically altering the metabolic pathways of the cell. The genetic alterations make fumarate an obligatory product during the growth phase. In some embodiments, fumarate or malate production is not obligatorily linked to growth. In such a case, the production of fumarate or malate takes place during a non-growth phase, for example. Sets of metabolic alterations or transformations that result in elevated levels of fumarate or malate biosynthesis are exemplified in Tables 1 and 2, respectively. Each alteration within a set corresponds to the requisite metabolic reaction that can be functionally disrupted. Functional disruption of all reactions within each set results increased production of fumarate or malate by the engineered strain. The corresponding reactions to the referenced alterations in Tables 1 and 2, and the gene or genes that potentially encode them in E. coli, are set forth in Table 3.

For example, for each strain exemplified in Table 1, the metabolic alterations that can be generated for increased fumarate production are shown in each row. These alterations include the functional disruption of from one to six or more reactions. In particular, 348 strains are exemplified in Table 1 that have non-naturally occurring metabolic genotypes. Each of these non-naturally occurring alterations result in an enhanced level of fumarate production during the exponential growth phase of the microorganism compared to a wild-type strain, under appropriate culture conditions. Appropriate conditions include, for example, those exemplified further below in the Example I such as particular carbon sources or reactant availabilities and/or adaptive evolution.

One such strain design for fumarate production involves deletions in fumarate reductase (FRD), alcohol dehydrogenase (ADHEr), lactate dehydrogenase (LDH_D), and glutamate dehydrogenase (GLUDy). This strain is predicted to have a growth-coupled yield of 1.83 moles of fumarate per mole of glucose consumed and the maximum growth rate is anticipated to be 0.09/hr as shown in FIG. 2. The deletion of FRD, ADHEr, and LDH_D prevents the formation and secretion of byproducts, namely succinate, ethanol and lactate. The elimination of glutamate dehydrogenase that transaminates alpha-ketoglutarate into glutamate with the utilization of a molecule of NADPH, disrupts a loop of reactions that form and use NADPH for synthesis of amino acids such as alanine and valine. All the disruptions can be implemented sequentially based on the necessity to do so. FIG. 2 shows the growth-coupled fumarate production characteristics of the strain (black, dashed) incorporating these disruptions compared with those of the wild-type E. coli network (black, at the maximum rate of growth, the wild-type network is not expected to form any fumarate.)

Figure 3:
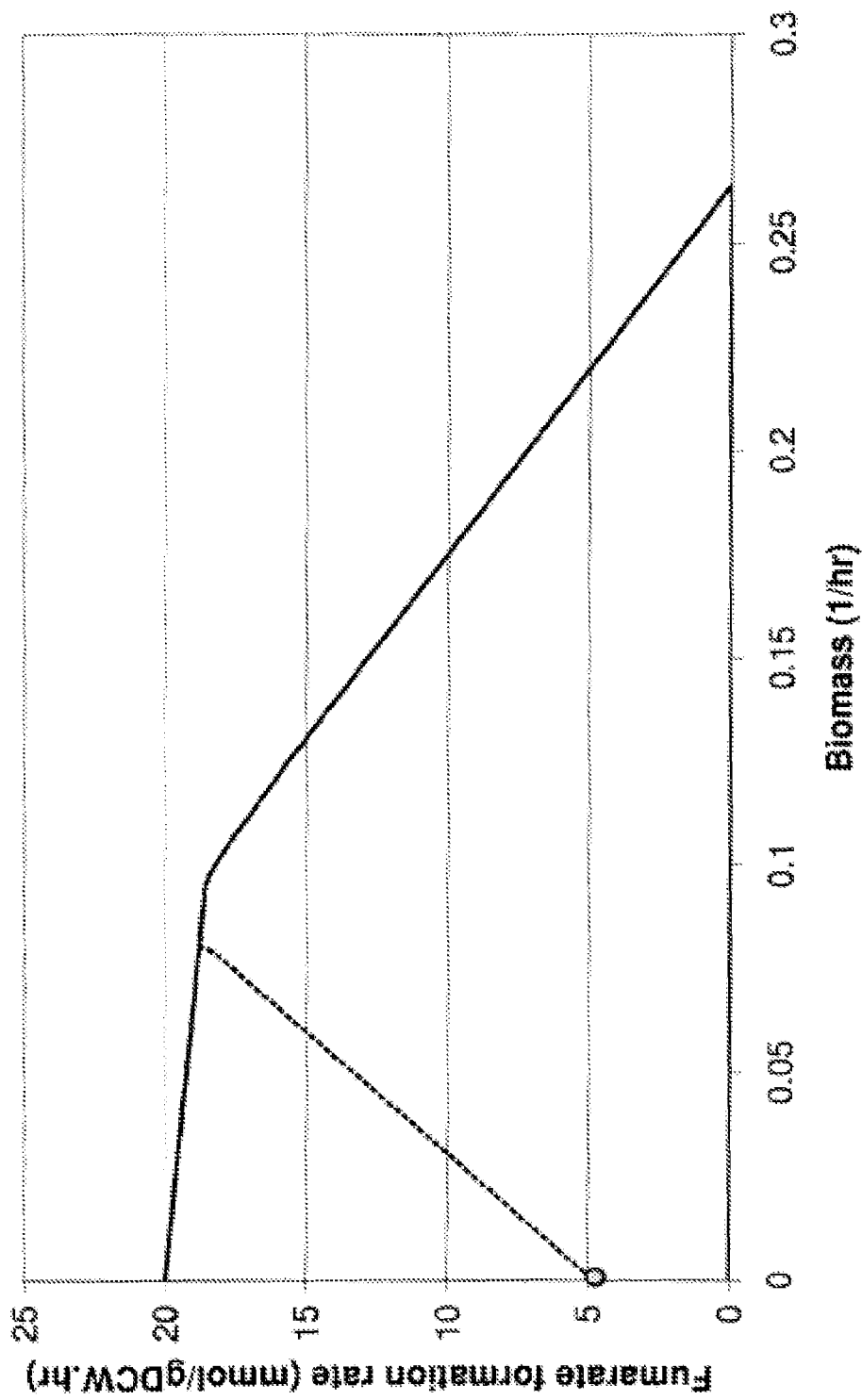
FIG. 3 shows increased fumarate production characteristics of another strain (black, dotted) compared with those of the wild-type *E. coli* network (black). The grey point shows the minimum amount of product formation expected from this strain.

Another strain, shown in FIG. 3, has three common deletions with the strain shown in FIG. 2 and involves elimination of malic enzyme (ME2) and transhydrogenase (THD2) activity additionally. Malic enzyme catalyzes the decarboxylation of malate to form pyruvate with the concomitant reduction of a molecule of NADP to form NADPH. Transhydrogenase catalyzes the oxidation of NADH causing the reduction of NADP into NADPH. The deletion of the NADPH-forming malic enzyme and the membrane-bound proton-translocating transhydrogenase catalyzed by PntAB prevents or reduces the formation of NADPH, thus preventing or reducing carbon from being funneled into amino acids instead of being converted into fumarate. The efficacy of the two latter knockouts for fumarate production can be assessed and implemented sequentially based on the necessity to do so.

The strain of FIG. 3 is expected to have a maximum growth-coupled yield of 1.87 moles of fumarate per mole of glucose consumed at an expected maximum growth rate of 0.08/hr. Note also that the strain is has a minimum theoretical product yield of 0.48 moles per mole of glucose (the grey point on the black, dotted curve). FIG. 3 shows the growth-coupled fumarate production characteristics of the strain (black, dotted) compared with those of the wild-type E. coli network (black). The grey point shows the minimum amount of product formation expected from this strain.

An additional disruption in PFL (pyruvate formate lyase) can improve the theoretical yield of fumarate marginally to 1.89 moles per mole of glucose consumed and the expected growth rate of this strain is 0.07 per hour.

Figure 4:
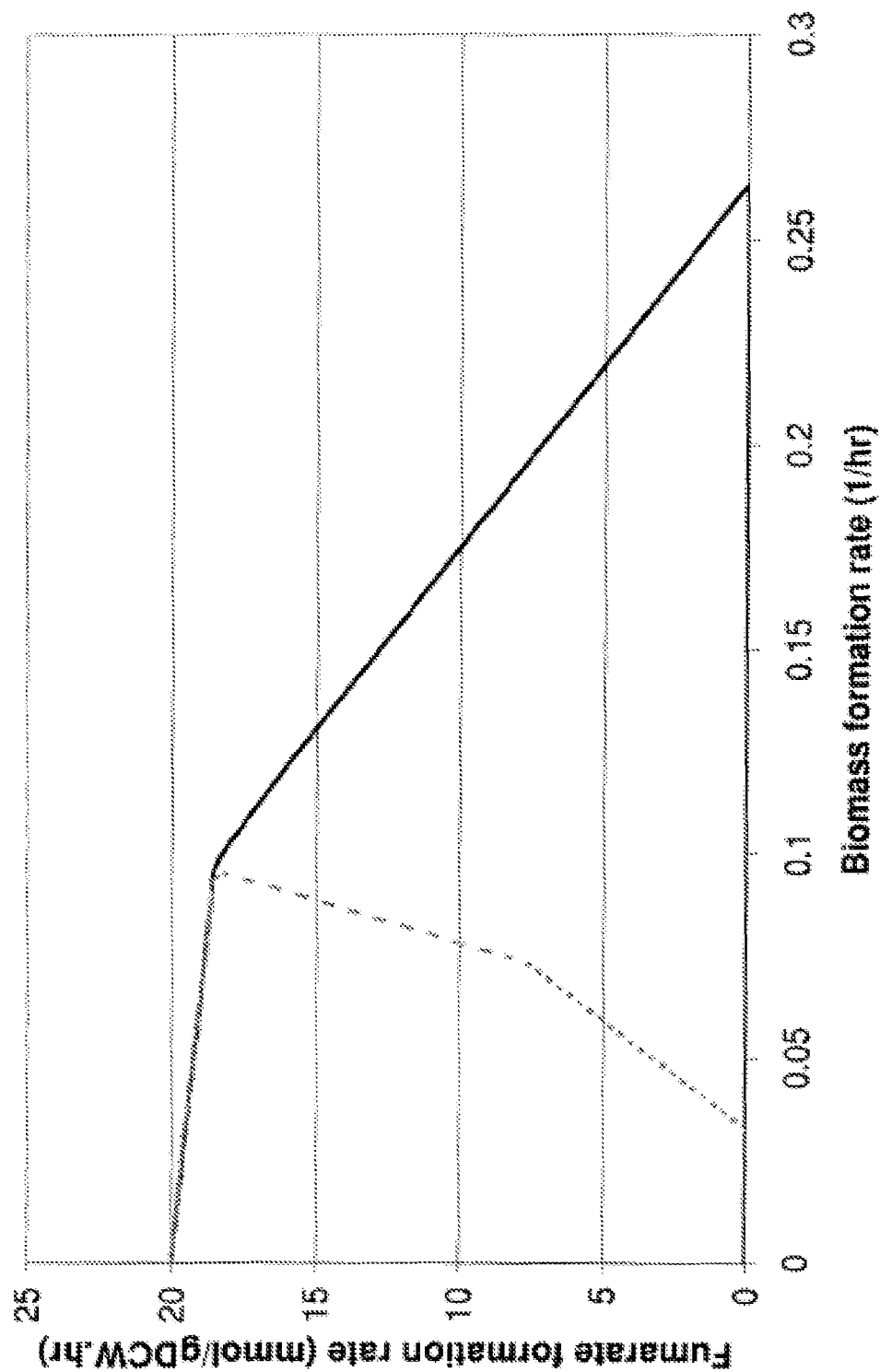
FIG. 4 shows the production curve for still another strain (grey, dashed) compared with the production curve for the wild-type *E. coli* network (black). Note that this strain design is equivalent to design B if an additional deletion in THD2 is introduced.

Another strain, shown in FIG. 4, disrupts the GLCpts mechanism of glucose transport and instead relies on hexokinase activity. This disruption along with disruption of FRD, ADHEr, LDH_D, and ME2 leads to an expected maximum growth rate for the strain at approximately 0.1 per hour. The product yield is expected to be 1.82 moles per mole of glucose consumed. The strain is expected to start producing fumarate once it reaches approximately 36% of its maximum theoretical biomass formation rate. FIG. 4 shows the production curve for this strain (grey, dashed) compared with the production curve for the wild-type E. coli network (black). Note that this strain is equivalent to the strain of FIG. 2 if an additional deletion in THD2 is introduced.

Figure 5:
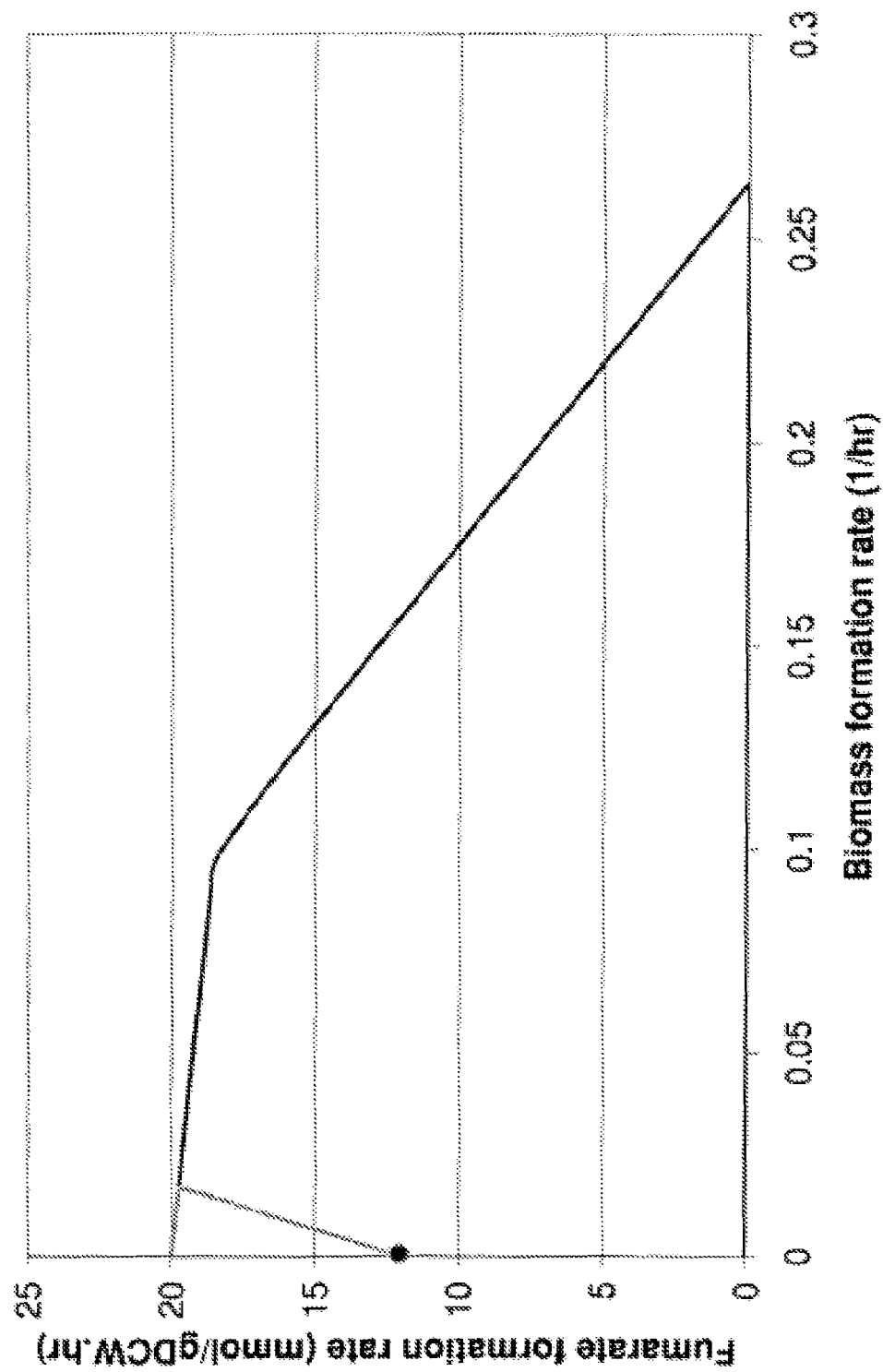
FIG. 5 shows the production curve for yet another strain (grey, dashed) compared with the production curve of the wild type *E. coli* network (black). The black point indicates the minimum amount of product formation expected from this strain.

Another strain, shown in FIG. 5, has deletions in FRD, ADHEr, LDH_D, ME2, THD2 and HEX1. The deletion in HEX1 forces glucose flux through the PTS system, converting an equivalent molar amount of phosphoenolpyruvate (PEP) into pyruvate. To attain a balance of cofactors, the network is forced to convert most of the pyruvate back into PEP through PEP synthase. This is an energy-intensive step and limits the biomass formation in the network. However, the carbon distribution provides PEP to be used by PPCK and subsequent channeling into the reductive TCA cycle. This leads to the very high fumarate yields in the network of up to 1.97 moles per mole of glucose consumed as shown in FIG. 5. These disruptions reduce the feasible solution space of the mutant network significantly and the strain is expected to have a minimum product yield of at least 1.25 moles per mole of glucose consumed as shown by the black point in FIG. 5. Although strain is predicted to grow slowly at a rate of approximately 0.02 per hour, the prospect of achieving near maximum theoretical product yields makes this design particularly useful. The strain is expected to secrete very small quantities of acetate and formate. FIG. 5 shows the production curve for the strain (grey, dashed) compared with the production curve of the wild type E. coli network (black). The black point indicates the minimum amount of product formation expected from this strain.

Figure 6:
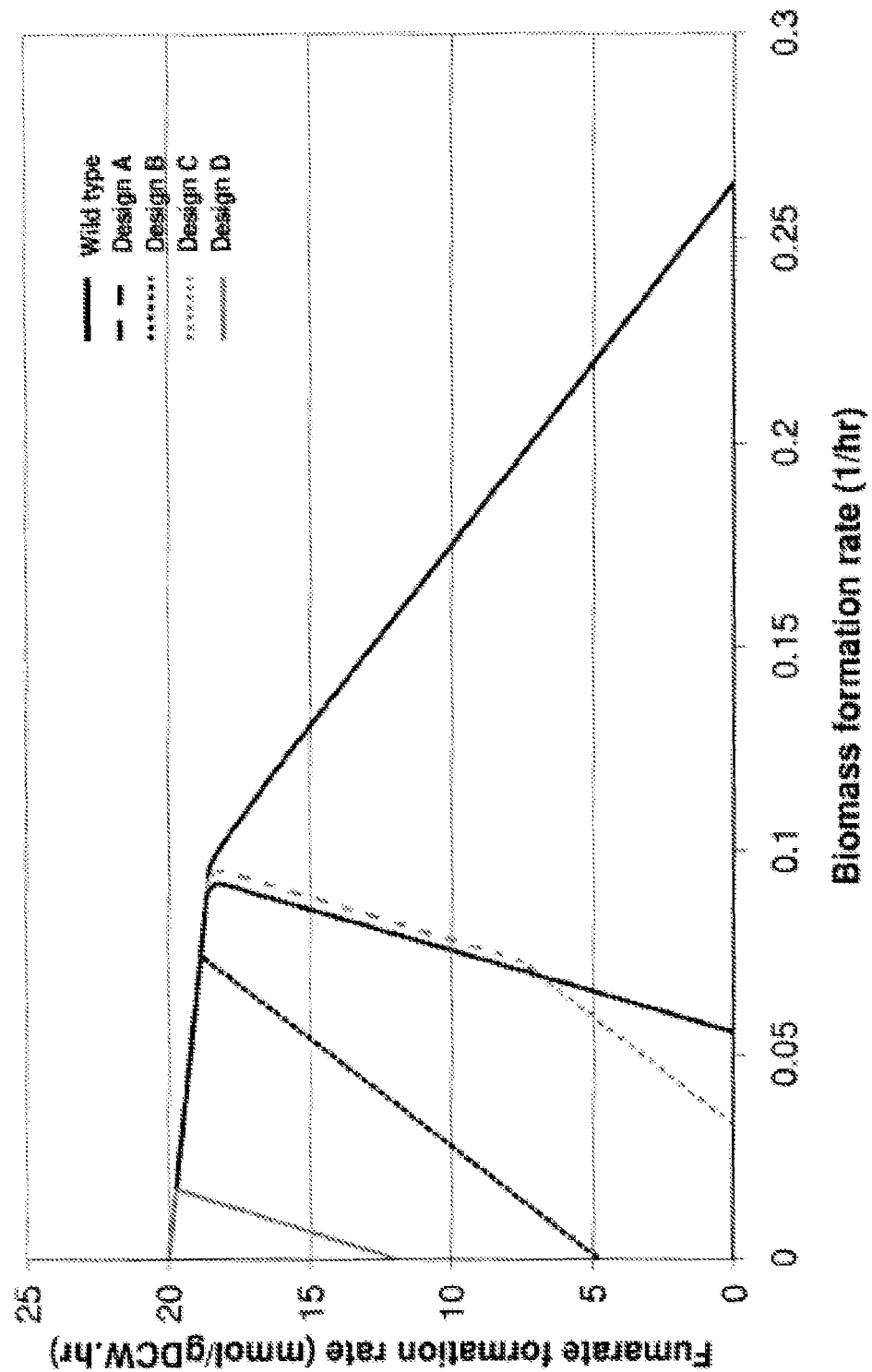
FIG. 6 shows the production curves for the strains in FIG. 2 (black, dashed), FIG. 3 (black, dotted), FIG. 4 (grey, dashed) and FIG. 5 (grey) compared with each other and with the production characteristics of the wild-type *E. coli* network (black). Note the reduction in feasible solution space as additional deletions are imposed on the network.

To provide a comparison of the fumarate production characteristics of the four strains discussed above, the production curves are presented on the same plot and compared with those of the wild-type E. coli network as shown in FIG. 6. Other strains for fumarate production in E. Coli are listed in Table 1. FIG. 6 shows the production curves for the strains in 1) black, dashed, 2) black, dotted, 3) grey, dashed and 4) grey compared with each other and with the production characteristics of the wild-type E. coli network in black. Note the reduction in feasible solution space as additional deletions are imposed on the network.

The anaerobic designs for the formation of malate are described below and utilize disruptions that have already been described for fumarate production. The strain designs for malate production have additional knockouts that preclude fumarate formation in the network.

Figure 7:
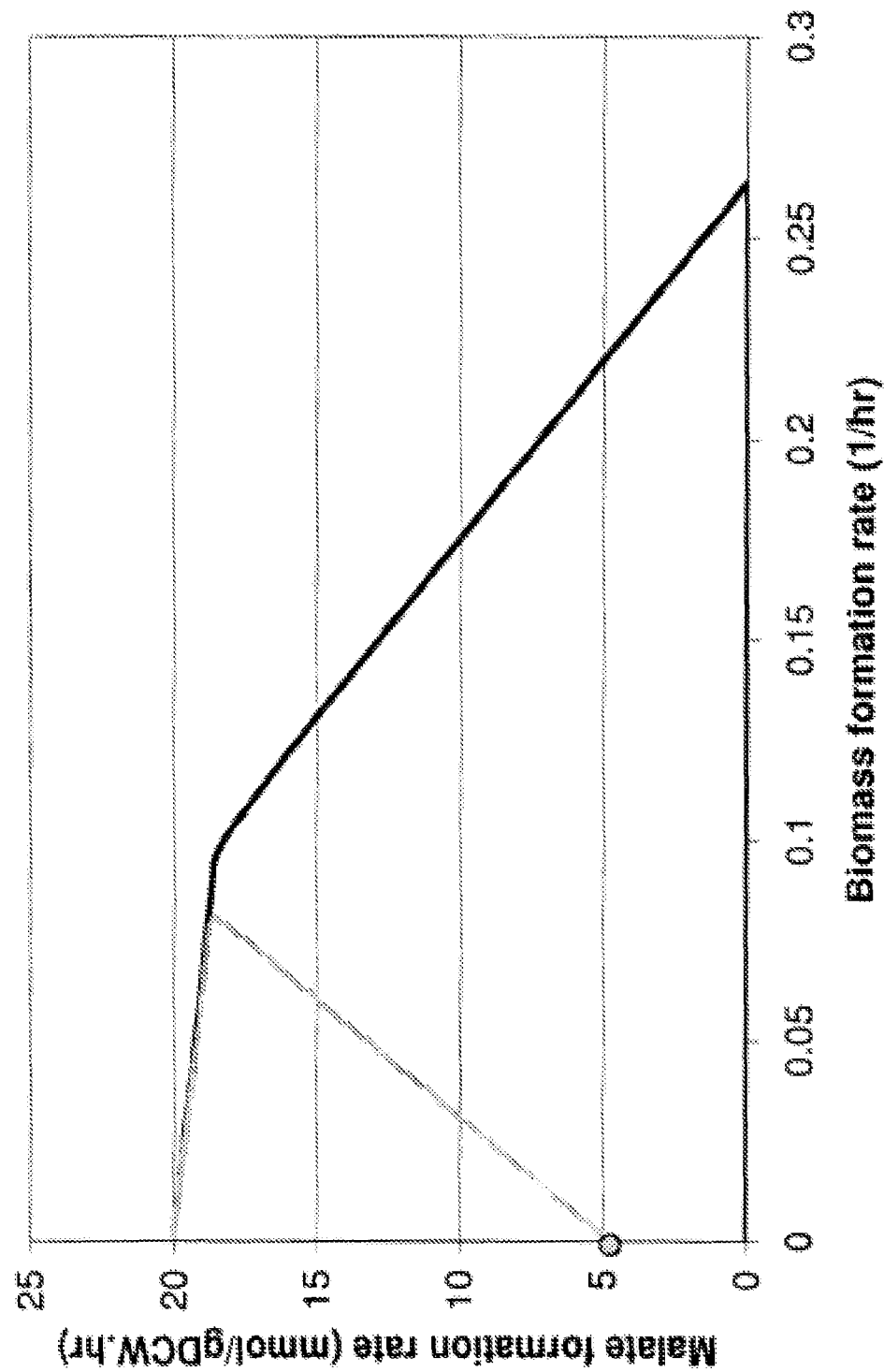
FIG. 7 shows the malate production curve for one strain (light grey) compared with the production curve for the wild type *E. coli* network (black).

One strain, shown in FIG. 7, allows for increased formation of malate by building upon the disruptions in the strain of FIG. 2. As described above, deletions in ADHEr, LDH_D, FRD, ME2 and THD2 allow for the enhanced formation of either fumarate or malate. An additional deletion in fumarase (FUM) prevents or reduces the conversion of malate into fumarate, leading to increase malate production of 1.86 moles per mole of glucose consumed as shown in FIG. 7.

Figure 8:
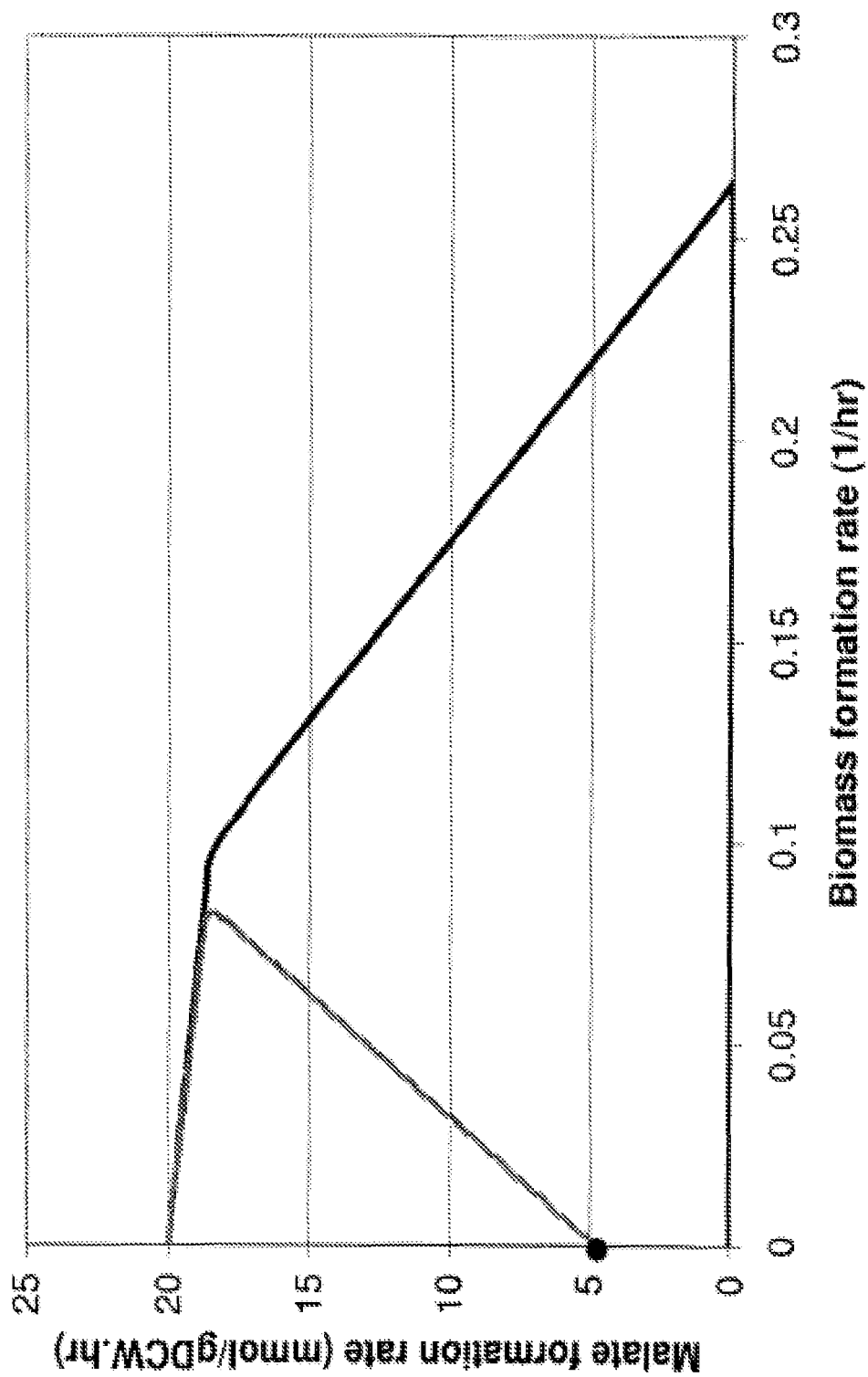
FIG. 8 shows the production curve for a modified malate-producing strain design based on the strain of FIG. 7, replacing deletion of FRD with deletion of ASPT, (grey) compared with that of the wild-type *E. coli* network (black).

Small modifications in this strain lead to another high-yielding strain shown in FIG. 8. Thus, instead of the FRD deletion, this strain has a disruption in aspartase (ASPT). The deletion of ASPT reinforces the effect of the fumarase deletion by preventing the network from converting oxaloacetate into aspartate which can subsequently be transformed into fumarate via aspartase. Without the deletion in ASPT, the strain can produce approximately 1.55 moles of succinate per mole of glucose consumed. This modified strain design with deletions in ADHEr, THD2, LDH_D, ME2, FUM, and ASPT leads to a growth-coupled theoretical yield of 1.85 moles of malate per mole of glucose consumed, shown in FIG. 8, with an expected growth rate of 0.08 per hour. Each of these strains is expected to have a non-zero minimum rate of malate production. Note the grey and black points in FIGS. 7 and 8 respectively. Several other strains with increased malate yields in E. Coli have been identified and are listed in Table 2.

Based on these strains, the invention also provides a non-naturally occurring microorganism having a set of metabolic modifications coupling fumarate or malate production to growth of the microorganism, the set of metabolic modifications includes disruption of one or more genes selected from the set of genes encoding proteins that include: (a) a fumarate reductase (FRD), an alcohol dehydrogenase (ADHEr), and a lactate dehydrogenase (LDH_D).

Analysis of the strains for fumarate production allows identification of a minimum set of deletions that increase fumarate production in the network. Note that PPCK was assumed to be reversible in the network. Briefly, deletions in fumarate reductase (FRD), alcohol dehydrogenase (ADHEr), and lactate dehydrogenase (LDH_D) prevent the formation of competing byproducts, namely, succinate, ethanol and lactate. The minimum enzyme disruption set based on the aforementioned strains includes disruption of fumarate reductase, alcohol dehydrogenase and lactate dehydrogenase. This corresponds to the following minimal exemplary gene disruption set:

frd (b4151 or b4152 or b4153 or b4154), adhE (b1421), and ldhA (b1380)

Additional disruptions have been identified by the OptKnock framework for the increased formation of fumarate. Note that these disruptions may have been predicted because no regulatory information is accounted for in the metabolic network. Nevertheless, it is predicted that supplementary disruptions or deletions in one or more of the functionalities, namely glutamate dehydrogenase (GLUDy), malic enzyme (ME2), and transhydrogenase (THD2) are useful for increased formation of the diacids of interest. These deletions can be introduced sequentially into E. coli K12. If these deletions/dirsuptions have to be introduced, the minimal set of activities that need to be deleted can be expanded to include the following:

Fumarate reductase, alcohol dehydrogenase, lactate dehydrogenase, and glutamate dehydrogenase, or Fumarate reductase, alcohol dehydrogenase, lactate dehydrogenase, and malic enzyme, or Fumarate reductase, alcohol dehydrogenase, lactate dehydrogenase, malic enzyme, and transhydrogenase Correspondingly, the minimal gene set can be expanded to yield:

frd (b4151 or b4152 or b4153 or b4154), adhE (b1421), ldhA (b1380), and gdhA (b1761), or frd (b4151 or b4152 or b4153 or b4154), adhE (b1421), ldhA (b1380), and maeB (b2463), or frd (b4151 or b4152 or b4153 or b4154), adhE (b1421), ldhA (b1380), pntAB (b1602, b1603), and maeB (b2463)

Further improvement in yields can be attained by disrupting one or more of the following functionalities: phosphotransacetylase (PTAr), the PTS mechanism of glucose transport (GLCpts), hexokinase (HEX1) or pyruvate formate lyase (PFL). Note that all the isozymes capable of carrying out a given activity should be disrupted or deleted given a possibility of the isozymes becoming active due to adaptive evolution. The enzyme disruption set after introducing these auxiliary deletions are listed below:

Fumarate reductase, alcohol dehydrogenase, lactate dehydrogenase, transhydrogenase, malic enzyme, and hexokinase, or Fumarate reductase, alcohol dehydrogenase, lactate dehydrogenase, malic enzyme, and the PTS transport mechanism of glucose, or Fumarate reductase, alcohol dehydrogenase, lactate dehydrogenase, transhydrogenase, malic enzyme, and pyruvate formate lyase The corresponding gene deletion sets are:

frd (b4151 or b4152 or b4153 or b4154), adhE (b1421), ldhA (b1380), pntAB (b1602, b1603), maeB (b2463) and glk (b2388)

frd (b4151 or b4152 or b4153 or b4154), adhE (b1421), ldhA (b1380), maeB (b2463), and pts (b1101 or b2415 or b2416 or b2417)

frd (b4151 or b4152 or b4153 or b4154), adhE (b1421), ldhA (b1380), pntAB (b1602, b1603), maeB (b2463), and pflAB (b0902, b0903)

For homomalate production, a disruption in fumarase (FUM) is utilized in addition to disruptions in alcohol dehydrogenase (ADHEr), lactate dehydrogenase (LDH_D) and fumarate reductase (FRD). Thus, the minimal enzyme deletion set is:

Fumarate reductase, alcohol dehydrogenase, lactate dehydrogenase, and fumarase

The disruption of these activities corresponds to the deletion of the following genes:

frd (b4151 or b4152 or b4153 or b4154), adhE (b1421), ldhA (b1380), and fumABC (b1611, b1612, b4122)

An alternative set of enzyme deletions can also enable homomalate production is as follows:

Alcohol dehydrogenase, lactate dehydrogenase, fumarase and L-aspartase

This corresponds to a minimum gene deletion set of:

adhE (b1421), ldhA (b1380), and fumABC (b1611, b1612, b4122) and aspA (b4139)

Thus, in some embodiments, the present invention provides a non-naturally occurring microbial organism that includes one or more gene disruptions occurring in genes encoding enzymes that increase homomalate production when the gene disruption reduces an activity of the enzyme, whereby the one or more gene disruptions confers increased production of homomalate onto said non-naturally occurring microorganism.

However, as explained earlier for fumarate production, disruptions in one or more out of the following reactions, glutamate dehydrogenase (GLUDy), transhydrogenase (THD2) and malic enzyme (ME2), can be useful, yielding the following minimal enzyme sets for deletion:

Fumarate reductase, alcohol dehydrogenase, lactate dehydrogenase, fumarase, and glutamate dehydrogenase, or Fumarate reductase, alcohol dehydrogenase, lactate dehydrogenase, fumarase, and malic enzyme, or Fumarate reductase, alcohol dehydrogenase, lactate dehydrogenase, fumarase, transhydrogenase and malic enzyme Accordingly, the gene deletion sets expand and are listed below:

frd (b4151 or b4152 or b4153 or b4154), adhE (b1421), ldhA (b1380), fumABC (b1611, b1612, b4122), and gdhA (b1761), or frd (b4151 or b4152 or b4153 or b4154), adhE (b1421), ldhA (b1380), fumABC (b1611, b1612, b4122), and maeB (b2463), or frd (b4151 or b4152 or b4153 or b4154), adhE (b1421), ldhA (b1380), fumABC (b1611, b1612, b4122), pntAB (b1602, b1603), and maeB (b2463).

Each of these strains may be supplemented with additional deletions if it is determined that the strain does not sufficiently increase the formation of the product. Alternatively, some other enzymes not known to possess significant activity may become active due to adaptive evolution or random mutagenesis and they will also have to be disrupted as well. For example, succinate dehydrogenase which oxidizes succinate to fumarate and is known to be active only under aerobic conditions may assume significant activity even under anaerobic conditions and may have to be disrupted. However, the list of gene disruption sets provided here serves as a starting point for construction of high-yielding malate and fumarate producing strains.

For fumarate and malate production metabolic modifications in eukarotic organisms sets of metabolic modifications are listed in Table 5. For acrylate production metabolic modifications in eukaryotic organisms can be selected from the set of metabolic modifications listed in Table 6.

The non-naturally occurring eukaryotic organism can have one or more gene disruptions included in a metabolic modification listed in Tables 5 or 6. The one or more gene disruptions can be a deletion. The non-naturally occurring eukaryotic organism of the invention can be selected from a group of eukaryotic organism having a metabolic modification listed in Tables 5 or 6. Non-naturally occurring eurkaryotic organisms of the invention include yeast, fungus, or any of a variety of other microorganisms applicable to fermentation processes. Exemplary eukaryotic species include those selected from *Saccharomyces cerevisiae, Schizosaccharomyces pombe, Kluyveromyces lactis, Kluyveromyces marxianus, Aspergillus terreus, Aspergillus niger, Rhizopus arrhizus, Rhizopus oryzae,* and *Pichia pastoris.*

The eukaryotic organisms having increased fumarate, malate, or acrylate production are exemplified herein with reference to an *S. cerevisiae* genetic background. However, with the complete genome sequence available for now more than 550 species (with more than half of these available on public databases such as the NCBI), including 395 microorganism genomes and a variety of yeast, fungi, plant, and mammalian genomes, the identification of an alternate species homolog for one or more genes, including for example, orthologs, paralogs and nonorthologous gene displacements, and the interchange of genetic alterations between organisms is routine and well known in the art. Accordingly, the metabolic alterations enabling increased production of the products described herein with reference to a particular organism such as *S. cerevisiae* can be readily applied to other microorganisms, especially other eukaryotic organisms. Given the teachings and guidance provided herein, those skilled in the art will know that a metabolic alteration exemplified in one organism can be applied equally to other organisms.

As described previously, homologues can include othologs and/or nonorthologous gene displacements. In some instances, such as when a substitute metabolic pathway exists in the species of interest, functional disruption can be accomplished by, for example, deletion of a paralog that catalyzes a similar, yet non-identical metabolic reaction which replaces the referenced reaction. Because there are differences among metabolic networks between different organisms, those skilled in the art will understand that the actual genes disrupted between different organisms may differ. However, given the teachings and guidance provided herein, those skilled in the art also will understand that the methods of the invention can be applied to all microorganisms to identify the cognate metabolic alterations between organisms and to construct an organism in a species of interest that will enhance the coupling of fumarate, malate, or acrylate biosynthesis to growth.

As described previously and further below, exemplary reactions, reaction nomenclature, reactants, products, cofactors and genes encoding enzymes catalyzing a reaction involved in the increased production of fumarate, malate, and acrylate in S. Cerevisiae are set forth in Tables 5, 6, 7, and 8.

The invention provides non naturally occurring eukaryotic organisms having growth-coupled production of fumarate, malate, or acrylate. Product production can be optionally obligatorily linked to the exponential growth phase of the microorganism by genetically altering the metabolic pathways of the cell. The genetic alterations can make the formation of the desired product obligatory to growth. Sets of metabolic alterations or transformations that result in elevated levels of fumarate, malate, or acrylate biosynthesis are exemplified in Tables 5 and 6, respectively. Each alteration within a set corresponds to the requisite metabolic reaction that should be functionally disrupted. Functional disruption of all reactions within each set results in the obligatory production of fumarate, malate, or acrylate by the engineered strain during the growth phase. The corresponding reactions to the referenced alterations in Tables 5 and 6, and the gene or genes that potentially encode them in S. cerevisiae, are set forth in Table 7.

For example, for each strain exemplified in Table 5, the metabolic alterations that can be generated for increase fumarate or malate production are shown in each row. These alterations include the functional disruption of from one to six or more reactions. In particular, 278 strains are exemplified in Table 5 that have non-naturally occurring metabolic genotypes. Each of these non-naturally occurring alterations result in an enhanced level of fumarate or malate production in the eukaryotic organism compared to a wild-type strain, under appropriate culture conditions. Appropriate conditions include, for example, those exemplified further below in the Example II such as particular carbon sources or reactant availabilities and/or adaptive evolution. Similarly, 495 strains are exemplified in Table 6 that have non-naturally occurring metabolic genotypes. Each of these non-naturally occurring alterations result in an enhanced level of acrylate production during the exponential growth phase of the eukaryotic organism compared to a wild-type strain, under appropriate culture conditions.

Given the teachings and guidance provided herein, those skilled in the art will understand that to disrupt an enzymatic reaction it is necessary to disrupt the catalytic activity of the one or more enzymes involved in the reaction. Disruption can occur by a variety of means including, for example, deletion of an encoding gene or incorporation of a genetic alteration in one or more of the encoding gene sequences as described previously in reference to the disruptions for E. Coli. The encoding genes targeted for disruption can be one, some, or all of the genes encoding enzymes involved in the catalytic activity. For example, where a single enzyme is involved in a targeted catalytic activity disruption can occur by a genetic alteration that reduces or destroys the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits in order to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is destroyed.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding an enzyme of a targeted metabolic reaction can be practiced in the methods of the invention and incorporated into the non-naturally occurring eukaryotic organisms of the invention in order to achieve the growth-coupled product production.

Herein below are described the designs identified for increasing fumarate, malate, and acrylate production in S. cerevisiae. For prediction of the strains, it was assumed that (i) the glucose uptake rate in the network was 10 mmol/gDCW·hr, (ii) a minimum non-growth associated maintenance requirement of 1 mmol/gDCW·hr was imposed upon the network, and (iii) phosphoenolpyruvate carboxykinase (PPCK) could operate in the carbon-fixing direction towards oxaloacetate. The reversibility of PPCK allows for the fixing of carbon dioxide such that a yield of 2 moles per mole of glucose for each of these products can be attained under microaerobic/anaerobic conditions. More importantly, it allows for production of ATP in the process. The ATP generation accompanying the reverse operability of PPCK supports the energy requirements for biomass formation as well as for product formation and export under anaerobic conditions. Note that the production of fumaric, malic and acrylic acids is otherwise energetically neutral in the S. cerevisiae metabolic network. The native PPCK in S. cerevisiae, encoded by Pck1, plays a key role in gluconeogenesis and operates to consume ATP to form PEP (Haarasilta and Oura, Eur. J. Biochem., 52:1-7 (1975)). Therefore, a heterologous enzyme, for example from *Mannheimia succiniciproducens* (Lee et al., Appl Environ Microbiol, 72:1939-1948 (2006)), *Anaerobiospirillum succiniciproducens* (Laivenieks et al., Appl Environ Microbiol, 63:2273-2280 (1997)), or *Actinobacillus succinogenes* (Kim, P. et al., Appl Environ Microbiol, 70:1238-1241 (2004)) with more favorable kinetics in the desired direction will be introduced into *S. cerevisiae*. The functioning of the enzyme in the requisite direction may require high concentrations of dissolved carbon dioxide in the fermentation medium. The protein sequences of the PEP carboxykinase enzymes mentioned in the text can be found via the following GenBank accession numbers and are summarized below:

| Gene name | Organism | Accession Number |
|---|---|---|
| pckA | *Mannheimia succiniciproducens* | YP_089485 (GI: 52426348) |
| pckA | *Anaerobiospirillum succiniciproducens* | O09460 (GI: 3122621) |
| pck | *Actinobacillus succinogenes* | ABX39017 (GI: 160415396) |

The designs for fumaric and malic acid production, but not for acrylic acid production, use a small supply of oxygen in the network. This is because diacid production in *S. cerevisiae* is energetically neutral under anaerobic conditions, even upon assuming the reversibility of PPCK. Assuming that the symport of the fumarate or malate dianion is feasible with a proton at moderately low pH values, one additional proton needs to be pumped out to maintain homeostasis. The ATPase in *S. cerevisiae* uses one ATP for exporting out each proton which makes fumarate and malate production energetically neutral under anaerobic conditions. A limited supply of oxygen therefore provides for favorable energetics that can enable growth and product export. Note that a more favorable proton translocation stoichiometry of the ATPase can render these designs energetically feasible even in the absence of oxygen. It has been recently shown that introducing point mutations into the ATPase encoded by PMA1 in *S. cerevisiae* can increase or decrease its proton coupling efficiency and in some cases, bring the number of protons excreted per ATP hydrolyzed closer to two (Guerra, G. et al., *Biochim Biophys Acta*, 1768:2383-2392 (2007)). Alternatively, a non-native ATPase with an increased coupling efficiency can be introduced, as was demonstrated (Morsomme, P. et al., *Embo J*, 15:5513-5526 (1996)) where a mutated plant ATPase permitted growth of an ATPase-deficient *S. cerevisiae* strain at a pH of 4.

In some embodiments, microaerobic (substantially anaerobic) designs can be used based on increased formation of the desired product. To examine this, production cones were constructed for each strain by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs were given a low priority.

The fumarate-production strategies identified by the OptKnock framework were ranked on the basis of their (i) theoretical yields, and (ii) growth-coupled fumarate formation characteristics. All the strains with high product yields involve four or more knockouts because fewer knockouts were found to provide markedly lower yields. Strains with high yields include, for example, those with about 70% or more yield. The engineered strains can include further metabolic modifications aimed at limiting the production of the fumarate precursor, malate that is at the same redox state as fumarate. For example, the fumarase enzyme(s) can be manipulated by using techniques such as directed evolution so that the overall kinetics favors the conversion of malate into fumarate. Another option is to use a fumarase enzyme from any of the *Rhizopus* species that are known to produce high concentrations of fumarate without malate formation (e.g. fumR from *R. oryzae*, GenBank accession number: X78576). In another embodiment, one can use the fumarase from *Euglena gracilis* with a $K_m$ value of 0.031 mM for fumaric acid (Shibata et al., *J Bacteriol*, 164:762-768 1985)). Further, if an additional enzyme activity is introduced into *S. cerevisiae* to channel fumarate into a different growth-coupled end product, it will drive the metabolism towards fumarate formation and prevent malate formation. A case in point is the production of acrylic acid. The introduction of an appropriate decarboxylase enzyme can shift the equilibrium between malate and fumarate towards fumarate, thus leading to all carbon being funneled to the desired acrylic acid product. Using all the above options will ensure that the conversion of malate into fumarate is at a higher rate than the export of malate via any of the malate transporters.

For the strains that follow, the enzyme names, their abbreviations, and the corresponding reaction stoichiometries are listed in Table 7. The genes that can be mutated in order to prevent the activities of the enzymes identified for disruption are also shown in Table 7. Finally, metabolites names corresponding to the abbreviations in the reaction equations are listed in Table 8.

Figure 9:
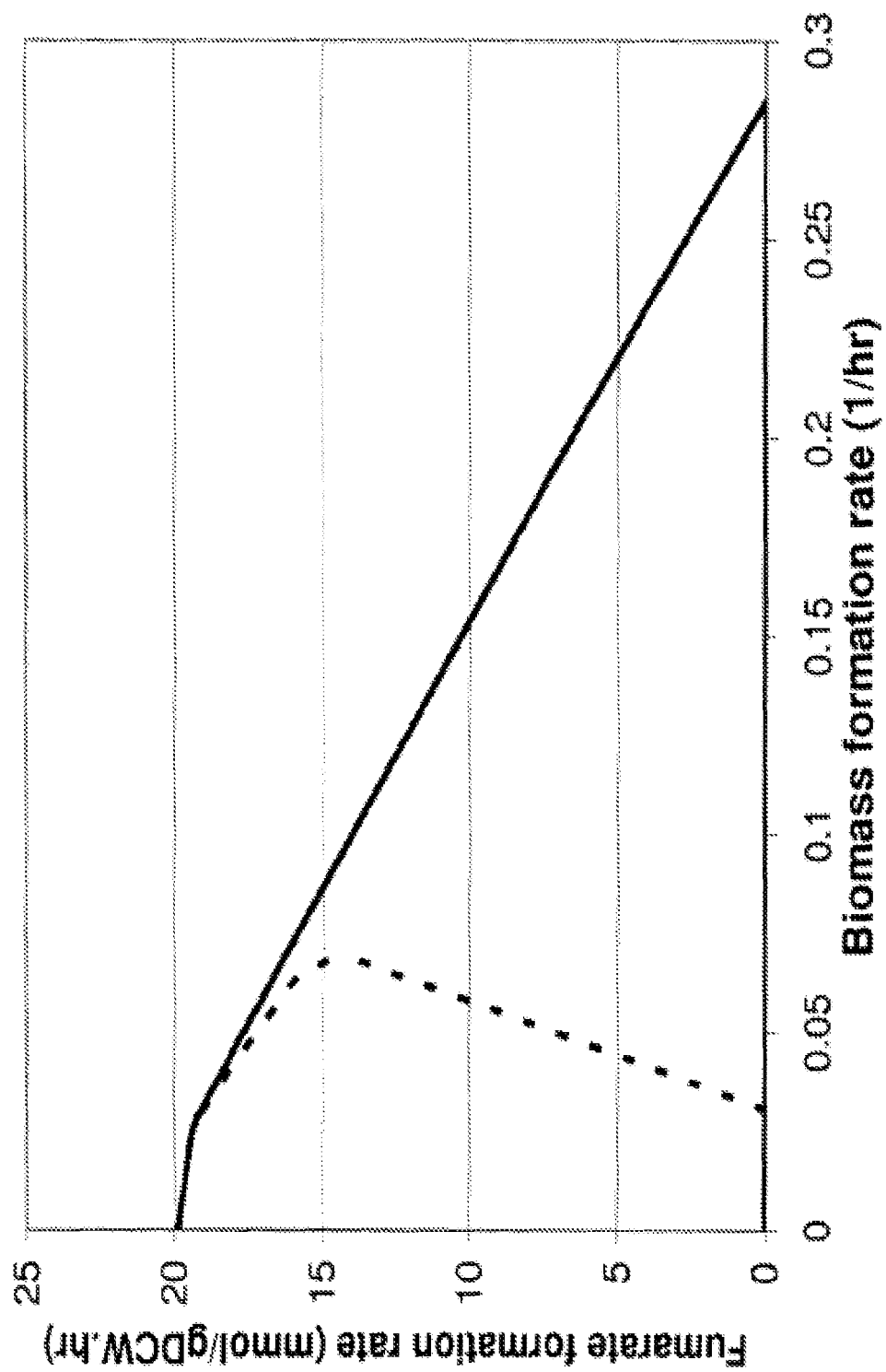
FIG. 9 shows increased fumarate production characteristics of one strain (black, dotted) compared with those of the wild-type *S. cerevisiae* network (black). At the maximum rate of growth, the wild-type network is not expected to form any fumarate.

One strain for fumarate production, shown in FIG. 9, involves disruptions in glycerol-3-phosphate dehydrogenase (G3PD), pyruvate decarboxylase (PYRDC), mitochondrial fumarase (FUMm), and soluble fumarate reductase (FRDcm). The disruptions in G3PD and PYRDC prevent glycerol secretion and reduce ethanol formation respectively. The disruption in FUMm prevents the carbon flux from being routed into the reductive mitochondrial TCA cycle. The network instead employs the cytosolic TCA cycle reactions to form fumarate. Finally, the disruption in FRDcm prevents the conversion of cytosolic fumarate into succinate. This strain is predicted to have a growth-coupled yield of 1.47 moles of fumarate per mole of glucose consumed and the maximum growth rate is anticipated to be 0.07/hr as shown in FIG. 9. If required, the sorbitol reductase activity (encoded by YHR104W) can be removed from the network. All the proposed disruptions can be implemented sequentially based on the necessity to do so.

Figure 10:
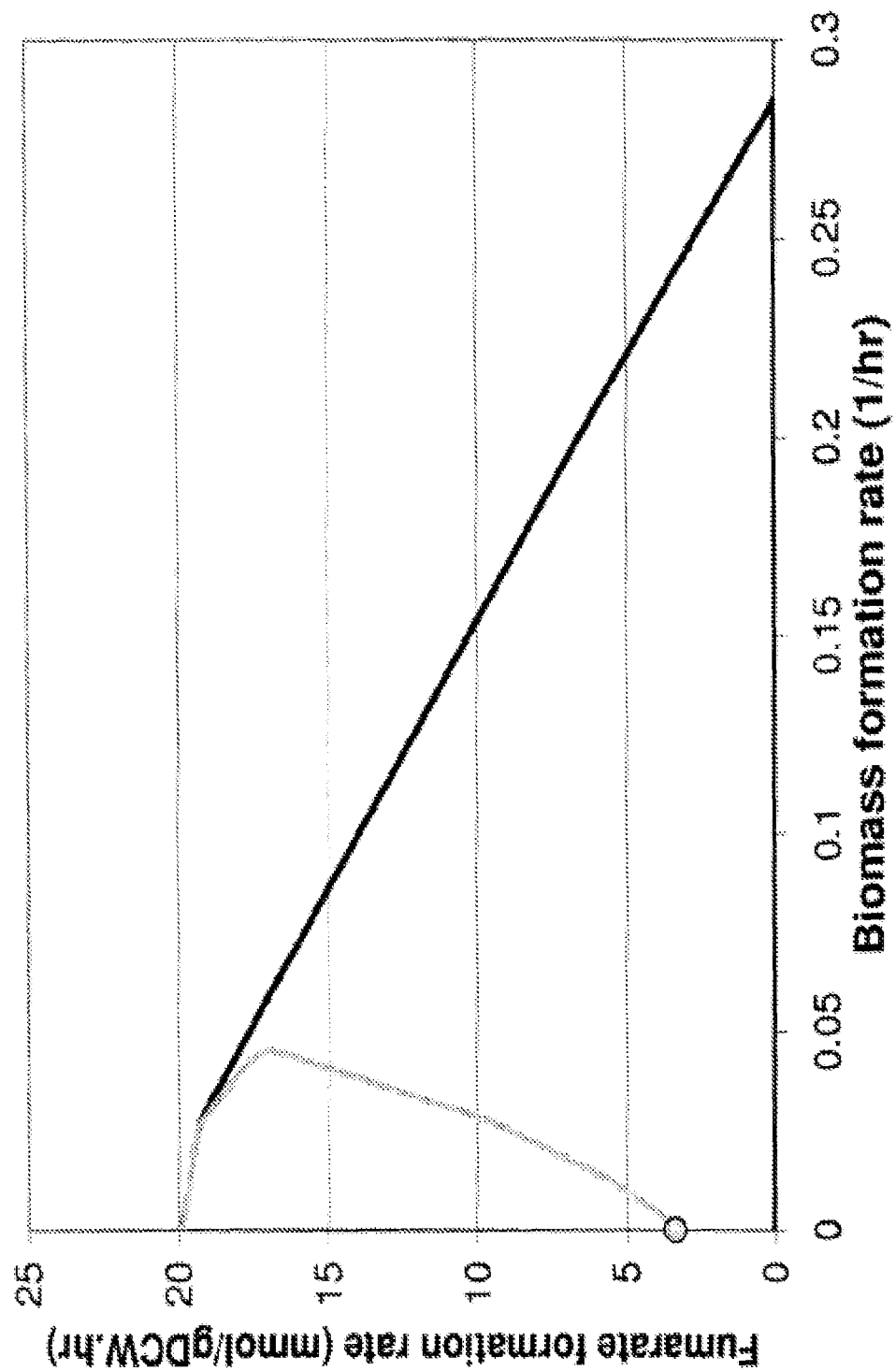
FIG. 10 shows increased fumarate production characteristics of another strain (light gray) compared with those of the wild-type *S. cerevisiae* network (black). The gray point shows the minimum amount of product formation expected from this strain.

The strain shown in FIG. 10 has four disruptions including malic enzyme (ME1m), pyruvate kinase (PYK), fumarase (FUMm), and soluble fumarate reductase (FRDcm), two of which are the same as those in FIG. 9. Under microaerobic conditions, this set of disruptions is expected to yield fumarate up to 1.71 moles/mole of glucose consumed. The disruptions in pyruvate kinase and the malic enzyme are targeted at preventing pyruvate formation in the network such that the maximum amount of PEP can be routed into the reductive TCA cycle using the energy-generating PPCK. As explained earlier, the disruptions in mitochondrial fumarase and in the soluble fumarate reductase prevent the carbon flux from being routed into the reductive mitochondrial TCA cycle and prevent further reduction of fumarate into succinate, respectively. With the imposed disruptions, the strain is expected to produce a minimum of 18% of its maximum theoretical yield see gray point in FIG. 10. The strain is predicted to have a maximum growth rate of 0.045/hr.

Figure 11:
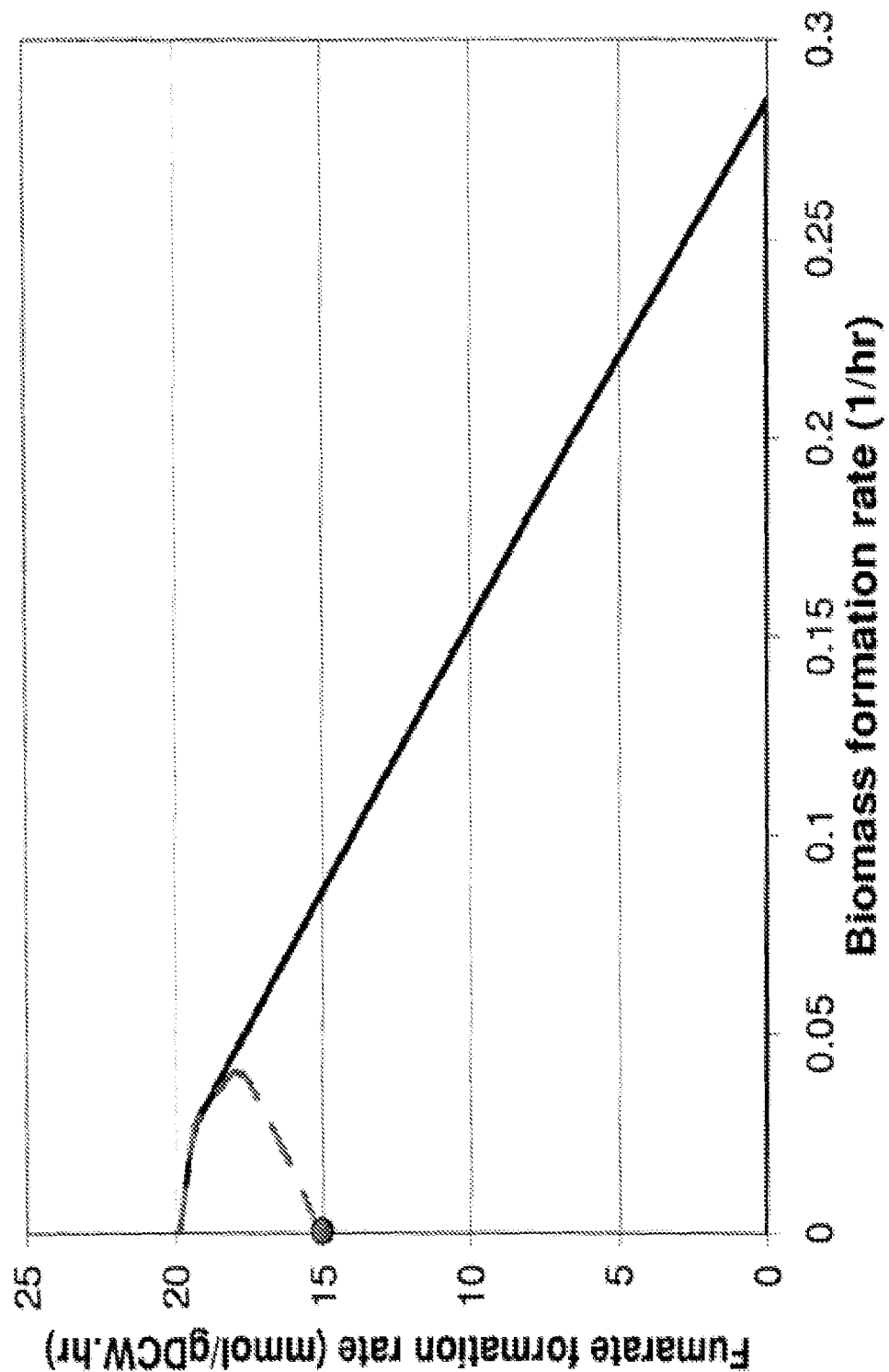
FIG. 11 shows the production curve for yet another strain (dark gray, dashed) compared with the production curve for the wild-type *S. cerevisiae* network (black). The dark gray point shows the minimum amount of fumarate production expected from this design.

The strain in FIG. 11 has an additional disruption in glucose-6-phosphate dehydrogenase as compared to the strain in FIG. 9. The disruption of G6PDH alters the cofactor balance in the network favorably for fumarate production at the cost of biomass production by preventing the NADPH formation required for biomass synthesis. These disruptions lead to an expected maximum growth rate of approximately 0.041 per hour for the strain as shown in FIG. 11. The maximum theoretical fumarate yield is 1.79 moles per mole of glucose consumed. The imposed disruptions reduce the feasible phenotypes significantly such that the strain is anticipated to produce a minimum of 84% of its maximum theoretical yield just to grow as shown by the dark gray point in FIG. 11.

Figure 12:
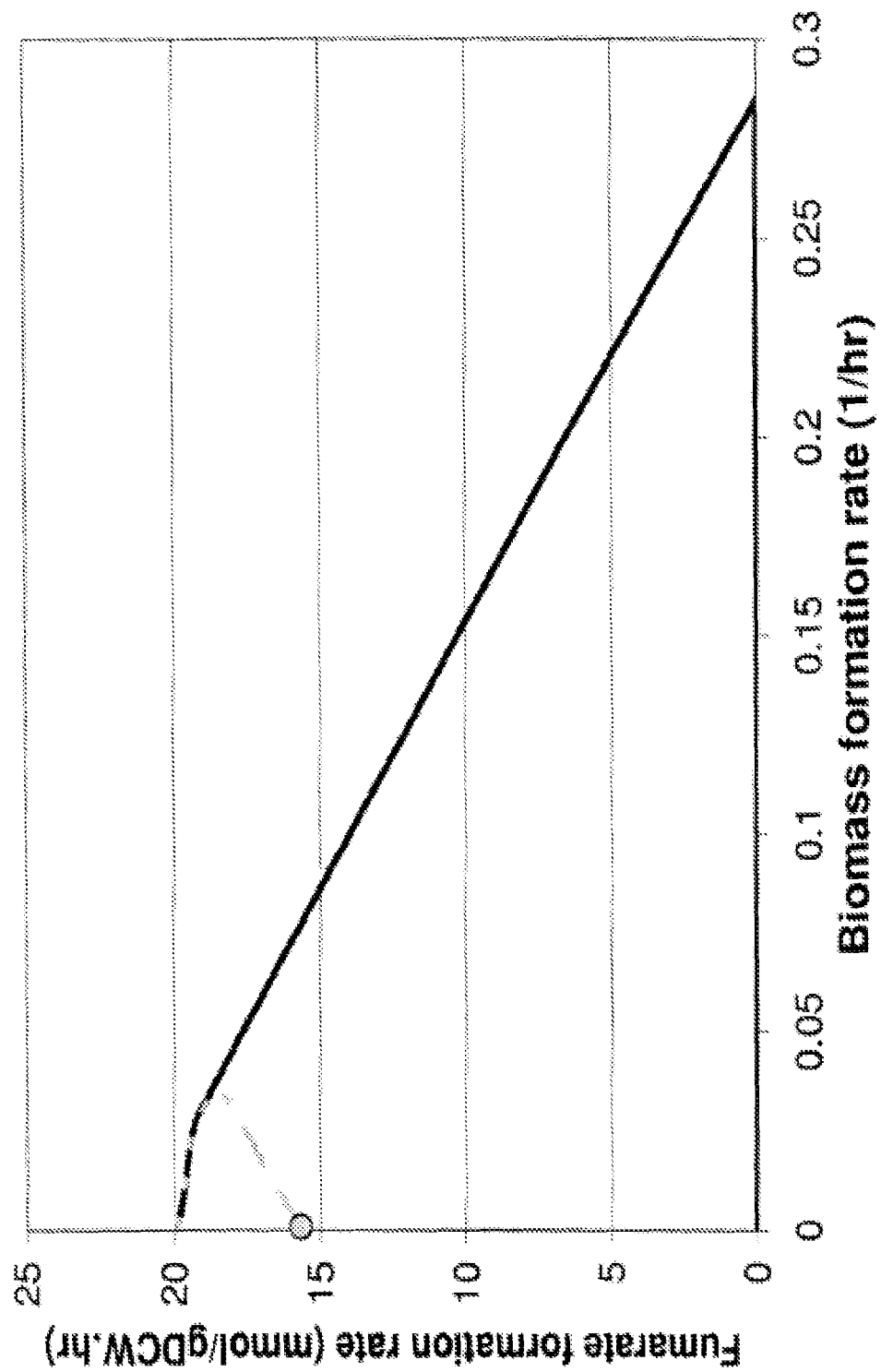
FIG. 12 shows the production curve for still another strain (light gray, dashed) compared with the production curve of the wild type *S. cerevisiae* network (black). The light gray point indicates the minimum amount of product formation expected from this strain.
Figure 13:
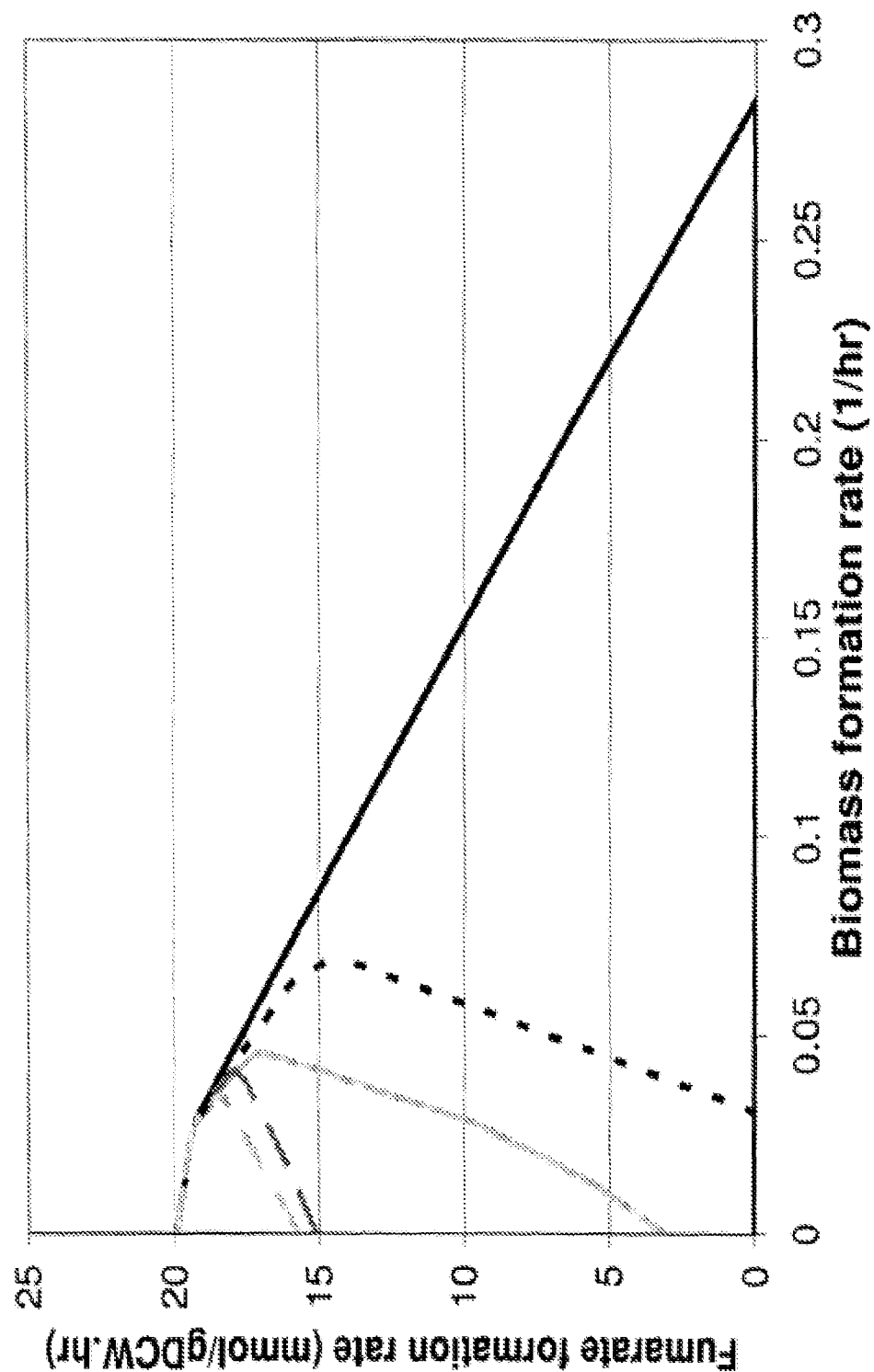
FIG. 13 shows the production curves for various strains in FIG. 9, black, dotted.

Another strain, shown in FIG. 12, has an additional disruption in isocitrate dehydrogenase as compared to the strain in FIG. 11, leading to a marginal increase in the expected maximum theoretical fumarate yield to 1.83 moles per mole of glucose consumed. The rationale is analogous to that explained for the disruption of G6PDH in design. The maximum biomass formation rate is anticipated to decrease from 0.04 per hour to 0.03 per hour.

To provide a comparison of the fumarate production characteristics of the four strains in FIGS. 9-12, FIG. 13 shows their production curves on the same plot and compares them with those of the wild-type S. cerevisiae network. All the other designs for fumarate production are listed in Table 5. All the designs proposed for fumarate production described above and in Table 5 can be used for malate production under microaerobic conditions by introducing an additional disruption in the cytosolic fumarase gene that will prevent the conversion of malate into fumarate.

The appropriate reactions for acrylate production from fumarate were added to a genome-scale model of S. cerevisiae very similar to the one described in Duarte et al., Genome Res, 14:1298-1309 (2004). Acrylic acid is a monocarboxylic acid and it has been assumed that it is exported by proton symport. This mechanism of acrylate export makes its production energetically feasible even under anaerobic conditions when a reversible PPCK in introduced. Several design strategies for producing acrylic acid were identified, a few of which are described in detail here with the remaining designs listed in Table 6.

Figure 14:
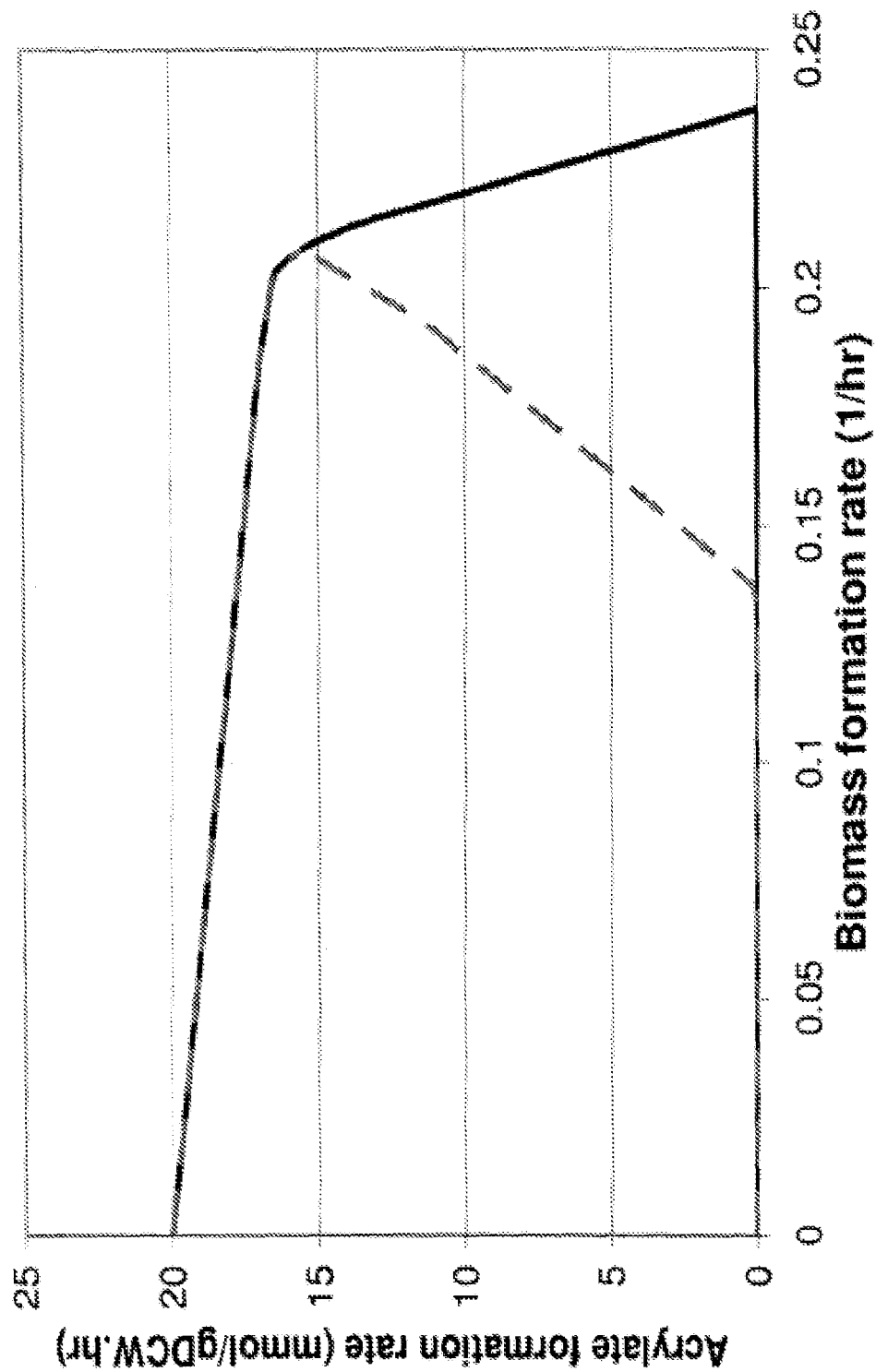
FIG. 14 shows the acrylate production curve for one strain (dark gray, dashed) compared with the production curve for the wild type *S. cerevisiae* network (black).

One strain for acrylate production, shown in FIG. 14, has a disruption in pyruvate decarboxylase (PYRDC). Under anaerobic conditions, a disruption in pyruvate decarboxylase reduces ethanol formation significantly. All the carbon flux is instead redirected towards acrylate production which also allows for the regeneration of the NADH generated in the network, leading to a tight coupling with biomass formation in the network. The maximum product yield is predicted to be 1.55 moles per mole of glucose consumed at the highest growth rate of 0.21 per hour.

Figure 15:
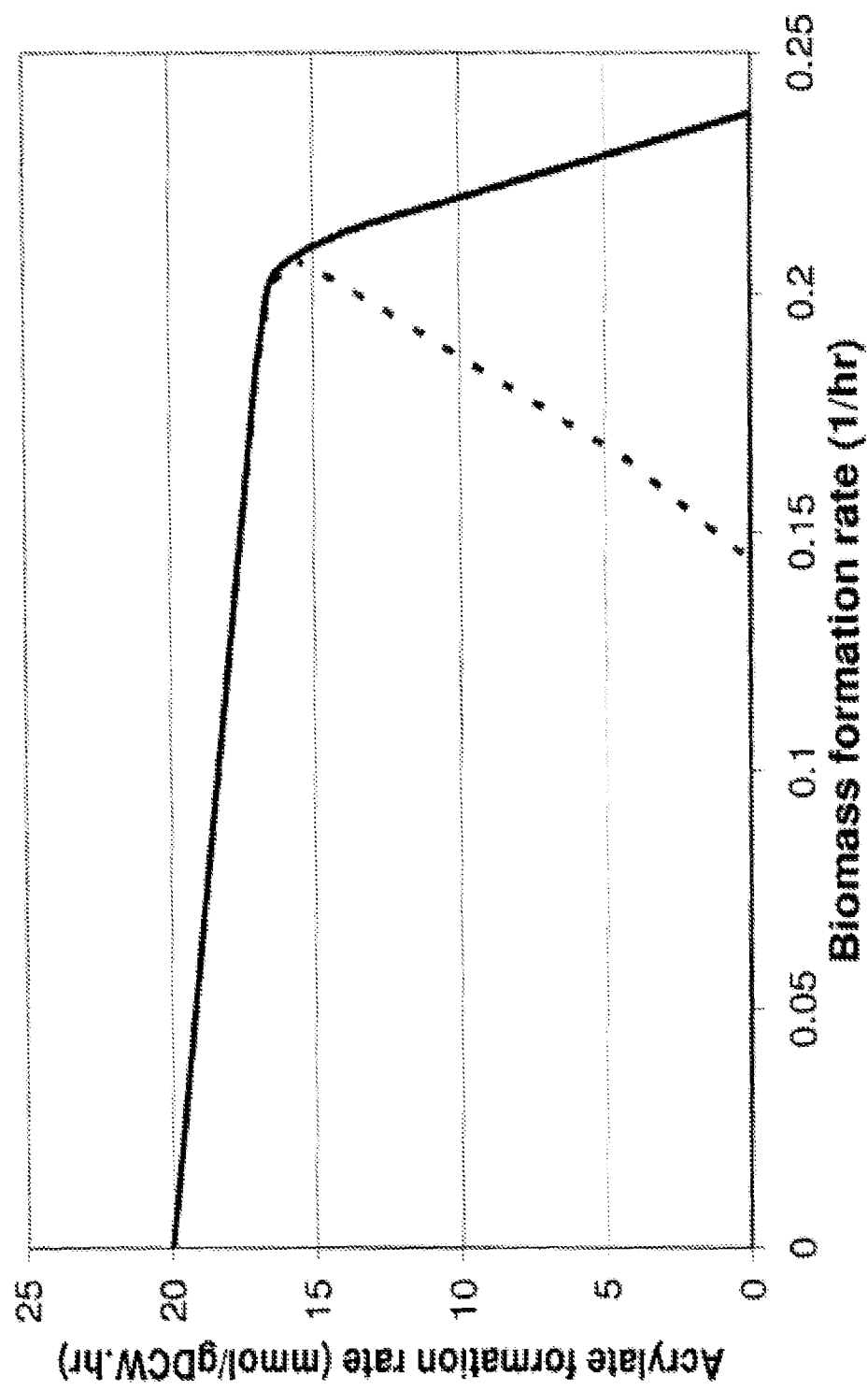
FIG. 15 shows the acrylate production curve for another strain (black, dotted) compared with the production curve for the wild type *S. cerevisiae* network (black).

Another strain, shown in FIG. 15, has disruptions in pyruvate kinase (PYK) and mitochondrial ATP synthase (ATPSm). The disruption in PYK prevents PEP conversion into pyruvate. The disruption of ATP synthase prevents ATP formation in the mitochondrion, removing the incentive for the network to route carbon flux into the mitochondrion. The product of YRJ121W is directly involved in the formation of F1-ATP synthase (beta subunit), while YMR064W is a translational regulator required for expression of the mitochondrial ATPase subunit 9 in yeast (Saltzgaber-Muller et al., *J Biol Chem.* 258:11465-11470 (1983)). Disruption of either of these two genes does not affect viability of the organism, making them good deletion candidates for lowering or eliminating the ATPSm activity. Other genes can also be targeted for elimination of the ATP synthase activity in *S. cerevisiae* (Tzagoloff and Dieckmann, *Microbiol Rev.* 54:211-225 (1990)). Under anaerobic conditions, the maximum theoretical acrylate yield of the strain is expected to be 1.55 moles per mole of glucose consumed at the maximum predicted growth rate of 0.21 per hour. In microaerobic conditions, this strain provides a slightly higher acrylate yield at 1.69 moles per mole of glucose and the maximum growth rate of the strain is predicted to be 0.23 per hour.

Figure 16:
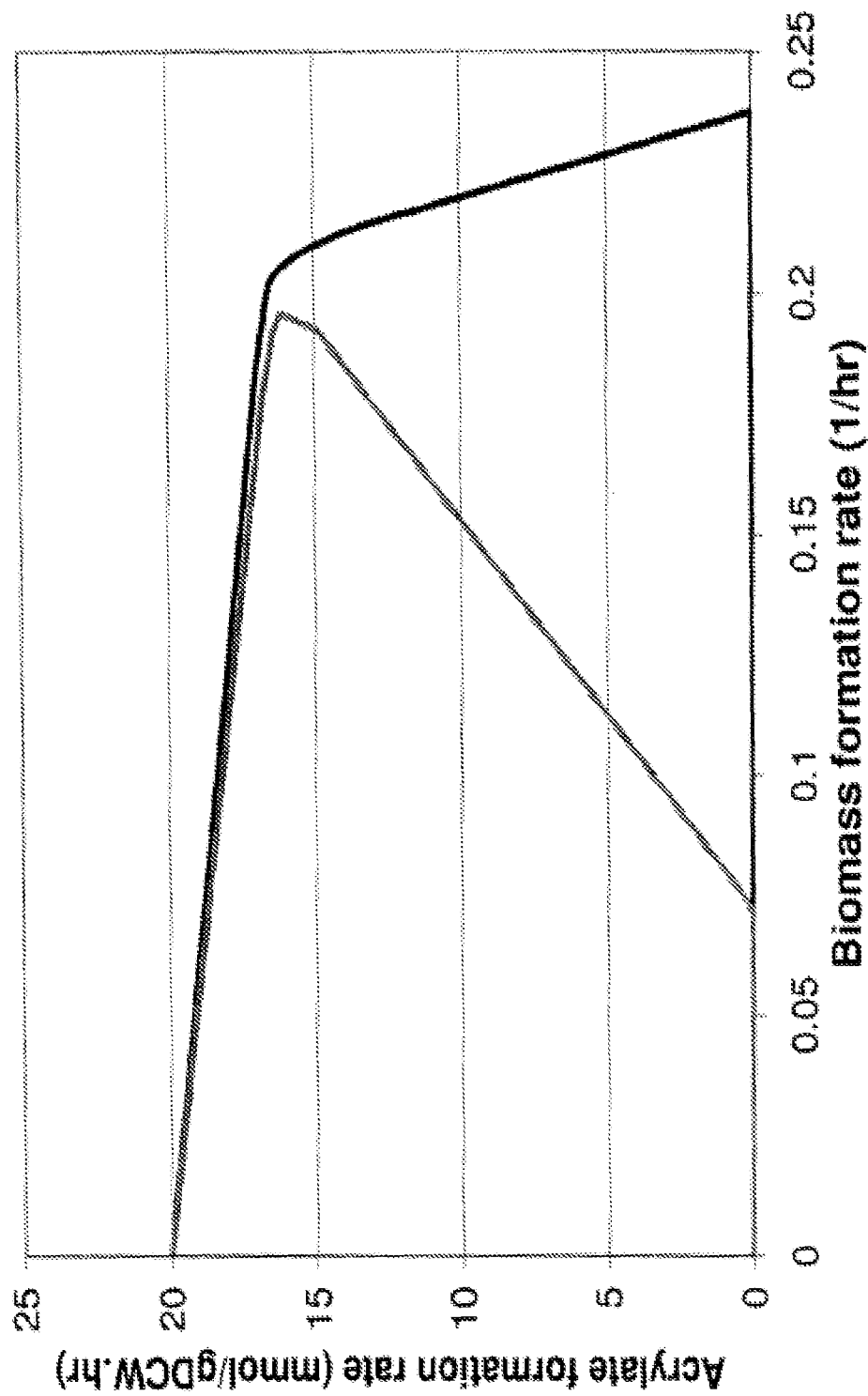
FIG. 16 shows the acrylate production curve for yet another strain (dark gray) compared with the production curve for the wild type *S. cerevisiae* network (black).

Another strain, shown in FIG. 16, has disruptions in malic enzyme (NAD-dependent) (ME1m) and in pyruvate kinase (PYK). These disruptions are geared towards preventing pyruvate formation in the network. Thus, they have a similar effect to the disruption of PYRDC which limits pyruvate formation by preventing its utilization for acetaldehyde and subsequently, ethanol formation. Overall, these two disruptions cause a high flux through PPCK, ultimately leading to a growth-coupled acrylate yield of 1.61 moles per mole of glucose in the network. The strain is calculated to have a maximum growth rate of 0.19 per hour.

Figure 17:
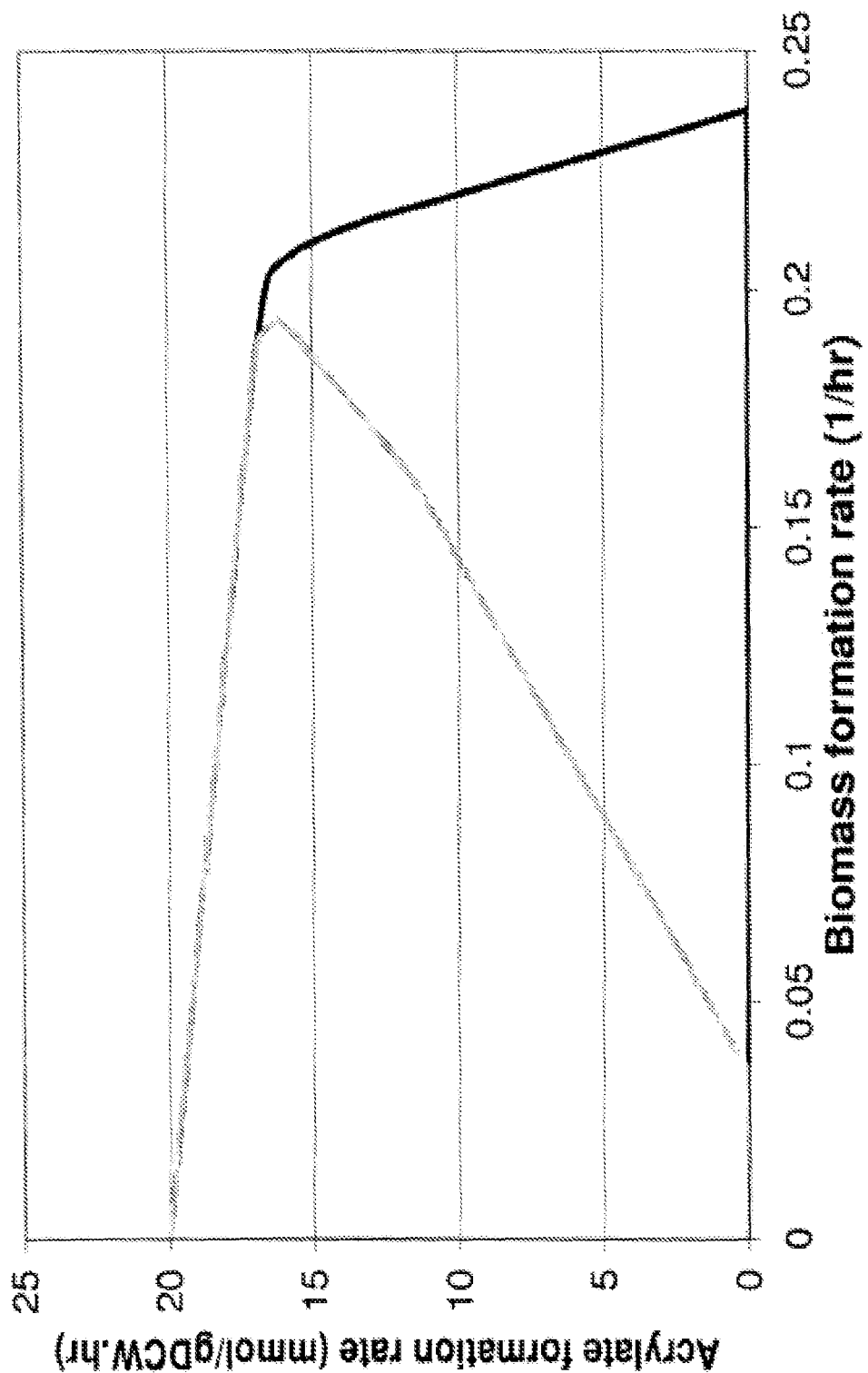
FIG. 17 shows the acrylate production curve for still another strain (light gray) compared with the production curve for the wild type *S. cerevisiae* network (black).

Yet another strain, shown in FIG. 17, has additional disruptions in fumarase (FUMm) and soluble fumarate reductase (FRDcm). These additional disruptions prevent the formation of succinate in the network. The net acrylate yield calculated for this design is 1.62 moles per mole of glucose consumed and the maximum growth rate is predicted to be 0.19 per hour.

Figure 18:
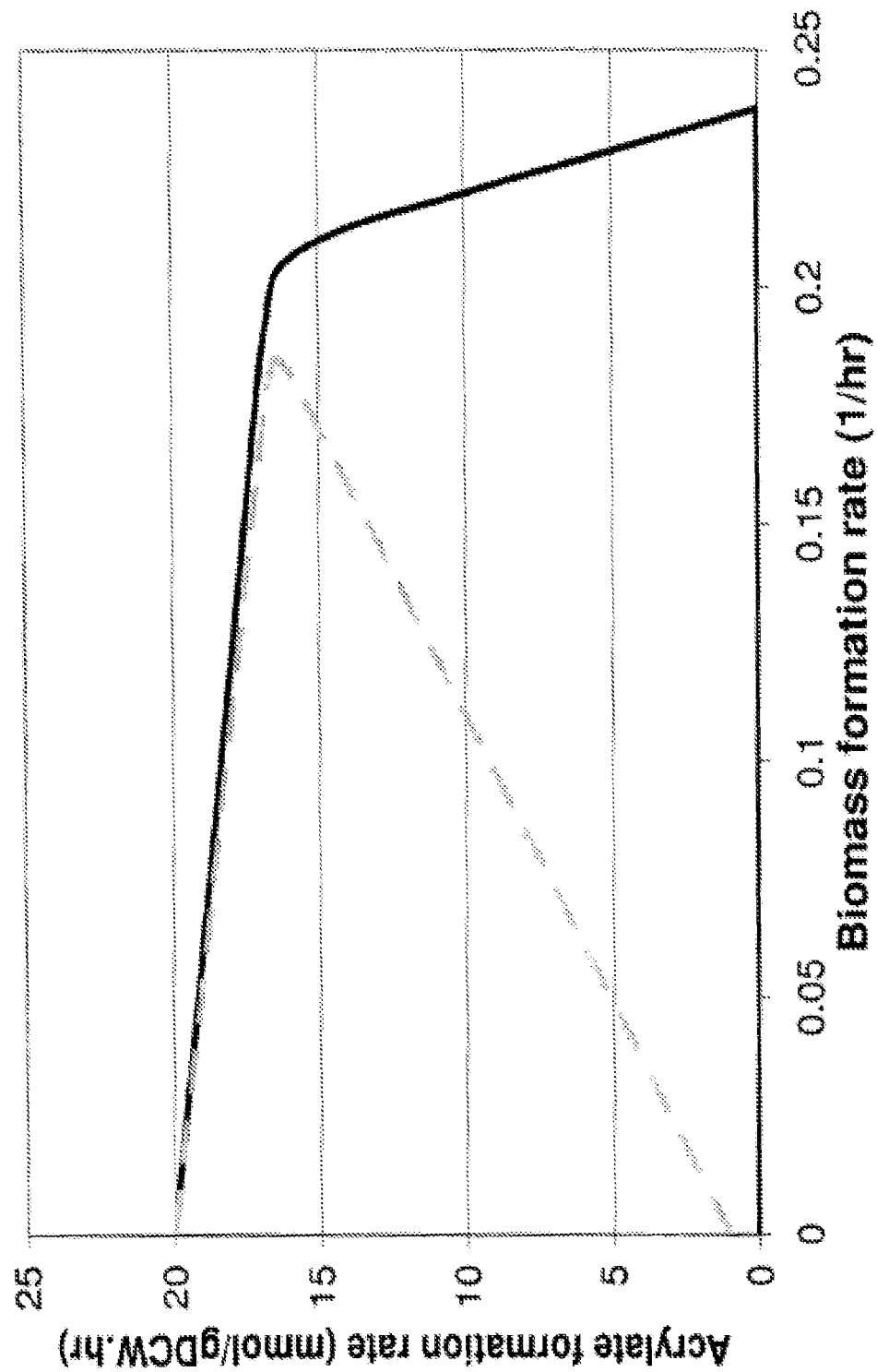
FIG. 18 shows the acrylate production curve for yet still another strain (light gray, dashed) compared with the production curve for the wild type *S. cerevisiae* network (black).

Still another strain, shown in FIG. 18, has additional disruptions in fumarase (FUMm) and soluble fumarate reductase (FRDcm). This strain can be grown in anaerobic conditions leading to acrylate production. The maximum theoretical acrylate yield of the strain is expected to be 1.65 moles per mole of glucose consumed at the maximum predicted growth rate of 0.18 per hour.

Accordingly, the invention also provides a non-naturally occurring eukaryotic organism having a set of metabolic modifications coupling fumarate, malate, or acrylate production to growth of the organism, the set of metabolic modifications includes disruption of one or more genes selected from the set of genes encoding proteins that include: (a) glycerol-3-phosphate dehydrogenase (G3PD), (b) pyruvate decarboxylase (PYRDC), (c) soluble fumarate reductase (FRDcm) and (d) mitochondrial fumarase (FUMm). In other embodiments, the set of metabolic modifications includes disruption of one or more genes selected from the set of genes encoding proteins that include: (a) malic enzyme (ME1m), (b) pyruvate kinase (PYK), (c) soluble fumarate reductase (FRDcm), and (d) mitochondrial fumarase (FUMm).

Based on an analysis of the strains for fumarate production, two alternative minimum set of disruptions can enable growth-coupled fumarate/malate production in the network. Note that PPCK was assumed to be reversible. Briefly, disruptions in glycerol-3-phosphate dehydrogenase (G3PD), pyruvate decarboxylase (PYRDC), soluble fumarate reductase (FRDcm) and mitochondrial fumarase (FUMm) are required for preventing or reducing the formation of competing byproducts, glycerol, ethanol and succinate. An alternative enzyme disruption set entails the removal of malic enzyme (ME1m), pyruvate kinase (PYK), soluble fumarate reductase (FRDcm) and mitochondrial fumarase (FUMm) for coupling fumarate production to growth. These correspond to the following minimal enzyme disruption sets:

Glycerol-3-phosphate dehydrogenase (G3PD), pyruvate decarboxylase (PYRDC), soluble fumarate reductase (FRDcm) and mitochondrial fumarase (FUMm), or Malic enzyme (ME1m), pyruvate kinase (PYK), soluble fumarate reductase (FRDcm) and mitochondrial fumarase (FUMm).

These enzyme disruption sets correspond to the following gene disruption sets: YDL022W (G3PD), YLR044C, YGR087C, YLR134W (isozymes for PYRDC), YPL262W (FUMm), and YEL047C (FRDcm), or YKL029C (ME1m), YOR347C, YAL038W (isozymes for PYK), YPL262W (FUMm), and YEL047C (FRDcm).

Note that all the isozymes capable of carrying out a given activity can be deleted given a possibility of the isozymes becoming active due to adaptive evolution. Further improvement in yields can be attained by deleting one or more of the following functionalities: glucose-6-phosphate dehydrogenase (G6PDH) and cytosolic NADP-dependent isocitrate dehydrogenase (ICDHy). The enzyme disruption sets after introducing these auxiliary disruptions are: Glycerol-3-phosphate dehydrogenase (G3PD), pyruvate decarboxylase (PYRDC), soluble fumarate reductase (FRDcm) and mitochondrial fumarase (FUMm), and glucose-6-phosphate dehydrogenase (G6PDH), or Malic enzyme (ME1m), pyruvate kinase (PYK), soluble fumarate reductase (FRDcm) and mitochondrial fumarase (FUMm), glucose-6-phosphate dehydrogenase (G6PDH) and cytosolic NADP-dependent isocitrate dehydrogenase (ICDHy).

These enzyme sets corresponds to the following gene disruption sets: YDL022W (G3PD), YLR044C, YGR087C, YLR134W (isozymes for PYRDC), YPL262W (FUMm), and YEL047C (FRDcm), YNL241C (G6PDH), or YKL029C (ME1m), YOR347C, YAL038W (isozymes for PYK), YPL262W (FUMm), and YEL047C (FRDcm), YNL241C (G6PDH), and YLR174W (ICDHy).

For malate production, the enzyme disruption sets can be augmented with the disruption of the cytosolic fumarase which is also encoded by YPL262W. Note that YPL262W encodes for both the cytosolic and the mitochondrial fumarases. However, its localization is determined by the N-terminal mitochondrial targeting sequence and its conformation (Sass et al., *J Biol Chem.* 278:45109-45116 (2003)).

Acrylate production in *S. cerevisiae* is feasible under anaerobic conditions assuming the reversibility of PPCK. Three alternative minimum enzyme disruption sets were identified. These entail (i) disruption in pyruvate decarboxylase, or (ii) disruption in malic enzyme in conjunction with a disruption in pyruvate kinase, or (iii) disruptions in pyruvate kinase and mitochondrial ATP synthase. The corresponding gene disruption sets are: YLR044C, YGR087C, YLR134W (PYRDC), or YKL029C (ME1m), YOR347C, YAL038W (PYK), or YOR347C, YAL038W (encode for PYK isozymes), YJR121W and YMR064W or any other combination of genes that eliminates mitochondrial synthase activity.

Each of these minimal sets can be augmented with supplementary disruptions to further enhance the acrylate yields. The auxiliary disruptions include but are not limited to mitochondrial fumarase, soluble fumarate reductase and glycerol-3-phosphate dehydrogenase. The corresponding gene disruptions are: YPL262W (FUMm), and YEL047C (FRDcm) and YDL022W (G3PD).

The disruption of pyruvate decarboxylase is very similar to the disruption of alcohol dehydrogenase in that both are targeted to prevent ethanol formation in the network. The disruption of alcohol dehydrogenase activity can completely eliminate ethanol formation. However, due to the presence of multiple alcohol dehydrogenases and the substrate promiscuity of these dehydrogenases, it can be difficult to completely remove the alcohol dehydrogenase activity. Therefore, PYRDC is included in the minimum enzyme disruption set.

Each of the strains described above can be supplemented with additional disruptions if it is determined that the predicted strain designs do not sufficiently couple the formation of the product with biomass formation. Alternatively, some other enzymes not known to possess significant activity under the growth conditions can become active due to adaptive evolution or random mutagenesis and can also be knocked out. For example, succinate dehydrogenase that oxidizes succinate to fumarate and is known to be active only under aerobic conditions may assume significant activity even under anaerobic conditions and may have to be knocked out. However, the list of gene disruption sets provided here serves as a starting point for construction of high-yielding growth-coupled malate, fumarate and acrylate production strains.

Therefore, the invention provides a method for producing fumaric acid malic acid, or acrylic acid that includes culturing a non-naturally occurring prokaryotic or eukaryotic microbial organism that includes one or more gene disruptions. The disruptions can occur in genes encoding an enzyme obligatory to coupling fumarate or malate production to growth of the microorganism when the gene disruption reduces an activity of the enzyme, such that the disruptions confer stable growth-coupled production of fumarate or malate onto the non-naturally occurring microorganism.

The non-naturally occurring prokaryotic or eukaryotic organisms of the invention can be employed in the growth-coupled production of fumarate, malate, or acrylate. Essentially any quantity, including commercial quantities, can be synthesized using the growth-coupled fumarate, malate, or acrylate producers of the invention. Because the organisms of the invention obligatorily couple fumarate, malate, or acrylate to continuous growth or near-continuous growth processes are particularly useful for biosynthetic production of fumarate, malate, or acrylate. Such continuous and/or near continuous growth processes are described above and exemplified below in the Example I. Continuous and/or near-continuous microorganism growth processes also are well known in the art. Briefly, continuous and/or near-continuous growth processes involve maintaining the microorganism in an exponential growth or logarithmic phase. Procedures include using apparatuses such as the Evolugator™ evolution machine (Evolugate LLC, Gainesville, Fla.), fermentors and the like. Additionally, shake flask fermentation and grown under microaerobic conditions also can be employed. Given the teachings and guidance provided herein those skilled in the art will understand that the growth-coupled fumarate producing microorganisms can be employed in a variety of different settings under a variety of different conditions using a variety of different processes and/or apparatuses well known in the art.

Generally, the continuous and/or near-continuous production of fumarate, malate, or acrylate will include culturing a non-naturally occurring growth-coupled fumarate, malate, or acrylate producing organism of the invention in sufficient nutrients and medium to sustain and/or nearly sustain growth in an exponential phase. Continuous culture under such conditions can be grown, for example, for a day, 2, 3, 4, 5, 6 or 7 days or more. Additionally, continuous cultures can include time durations of 1 week, 2, 3, 4 or 5 or more weeks and up to several months. It is to be understood that the continuous and/or near-continuous culture conditions also can include all time intervals in between these exemplary periods. In particular embodiments, culturing is conducted in a substantially anaerobic culture medium.

Fumarate, malate, or acrylate can be harvested or isolated at any time point during the continuous and/or near-continuous culture period exemplified above. As exemplified below, the longer the microorganisms are maintained in a continuous and/or near-continuous growth phase, the proportionally greater amount of fumarate and malate can be produced.

One consideration for bioprocessing is whether to use a batch or continuous fermentation scheme. One difference between the two schemes that will influence the amount of product produced is the presence of a preparation, lag, and stationary phase for the batch scheme in addition to the exponential growth phase. In contrast, continuous processes are kept in a state of constant exponential growth and, if properly operated, can run for many months at a time. For growth-associated and mixed-growth-associated product formation, continuous processes provide much higher productivities (i.e., dilution rate times cell mass) due to the elimination of the preparation, lag, and stationary phases. For example, given the following reasonable assumptions:

Monod kinetics(i.e.,$\mu=\mu_m \cdot S/(K_s+S)$)

$\mu_m=1.0\ hr^{-1}$ final cell concentration/initial cell concentration=20

$t_{prep}+t_{lag}+t_{stat}=5\ hr$ feed concentration of limiting nutrient>>$K_s$ increased productivity from a continuous process has been estimated at 8-fold, Shuler et al, *Prentice Hall, Inc.: Upper Saddle River, N.J.*, 245-247.

Despite advantages in productivity, many more batch processes are in operation than continuous processes for a number of reasons. First, for non-growth associated product formation (e.g., penicillin), the productivity of a batch system may significantly exceed that of a continuous process because the latter would have to operate at very low dilution rates. Next, production strains generally have undergone modifications to their genetic material to improve their biochemical or protein production capabilities. These specialized strains are likely to grow less rapidly than their parental complements whereas continuous processes such as those employing chemostats (fermenters operated in continuous mode) impose large selection pressures for the fastest growing cells. Cells containing recombinant DNA or carrying point mutations leading to the desired overproduction phenotype are susceptible to back-mutation into the original less productive parental strain. It also is possible for strains having single gene disruptions to develop compensatory mutations that will tend to restore the wild-type growth phenotype. The faster growing cells usually outcompete their more productive counterparts for limiting nutrients, drastically reducing productivity. Batch processes, on the other hand, limit the number of generations available by not reusing cells at the end of each cycle, thus decreasing the probability of the production strain reverting back to its wild-type phenotype. Finally, continuous processes are more difficult to operate long-term due to potential engineering obstacles such as equipment failure and foreign organism contamination. The consequences of such failures also are much more considerable for a continuous process than with a batch culture.

For small-volume production of specialty chemicals and/or proteins, the productivity increases of continuous processes rarely outweigh the risks associated with strain stability and reliability. However, for the production of large-volume, growth-associated products such as fumarate, the increases in productivity for a continuous process can result in significant economic gains when compared to a batch process. Although the engineering obstacles associated with continuous bioprocess operation would always be present, the strain stability concerns can be overcome through metabolic engineering strategies that reroute metabolic pathways to reduce or avoid negative selective pressures and favor production of the target product during the exponential growth phase.

The invention provides a method for producing fumaric acid, malic acid, or acrylic acid that includes culturing a non-naturally occurring prokaryotic or eukaryotic organism that includes one or more gene disruptions as described above. The disruptions can occur in genes encoding an enzyme obligatory to coupling fumarate, malate, or acrylate production to growth of the microorganism when the gene disruption reduces an activity of the enzyme, such that the disruptions confer increased production of fumarate, malate, or acrylate onto the non-naturally prokaryotic or eukaryotic organism. The gene disruptions can also be non-growth coupled in other embodiments.

In some embodiments, the gene disruption can include a complete gene deletion. In some embodiments other means to disrupt a gene include, for example, frameshifting by omission or addition of oligonucleotides or by mutations that render the gene inoperable. One skilled in the art will recognize the advantages of gene deletions, however, because of the stability it may confer to the non-naturally occurring organism from reverting to its wild-type. In particular, the gene disruptions are selected from the gene set that includes genes detailed herein above.

In order to confirm the computational predictions, the strains can be constructed, evolved, and tested. Gene deletions are introduced into wild-type, haploid *S. cerevisiae*, for example, by homologous recombination of the gene interrupted by the KanMX cassette, flanked by loxP sites enabling removal and recycling of the resistance marker (Wach et al., *PCR-based gene targeting in Saccharomyces cerevisiae*, in *Yeast Gene Analysis*, M. F. Tuite, Editor. 1998, Academic Press: San Diego.). Starting with a loxP-kanMX-loxP sequence on a plasmid, an artificial construct with this sequence flanked by fragments of the gene of interest can be created by PCR using primers containing both 45-50 bp target sequence followed by a region homologous to the above cassette. This linear DNA is transformed into wild-type *S. cerevisiae*, and recombinants are selected by geneticin resistance. Colonies can be purified and tested for correct double crossover by PCR. To remove the KanMX marker, a plasmid containing the Cre recombinase and bleomycin resistance will be introduced, promoting recombination between the loxP sites (Gueldener, U., et al., *A second set of loxP marker cassettes for Cre-mediated multiple gene knockouts in budding yeast*, in *Nucleic Acids Res.* 2002. p. e23.). Finally, the resulting strain can be cured of the Cre plasmid by successive culturing on media without any antibiotic present. The final strain will have a markerless gene deletion, and thus the same method can be used to introduce multiple deletions in the same strain.

The engineered strains can be characterized by measuring the growth rate, the substrate uptake rate, and the product/byproduct secretion rate. Cultures are grown overnight and used as inoculum for a fresh batch culture for which measurements are taken during exponential growth. The growth rate can be determined by measuring optical density using a spectrophotometer (A600). Concentrations of glucose and other organic acid byproducts in the culture supernatant are determined by HPLC using an HPX-87H column (BioRad), and used to calculate uptake and secretion rates. All experiments are performed with triplicate cultures.

The disruption strains are initially expected to exhibit suboptimal growth rates until their metabolic networks have adjusted to their missing functionalities. To assist in this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several E. coli mutants that had been adaptively evolved on various substrates to reach the growth rates predicted a priori by an in silico model (Fong and Palsson, Nat Genet, 36:1056-1058 (2004)). Should the OptKnock predictions prove successful; the growth improvements brought about by adaptive evolution will be accompanied by enhanced rates of fumarate, malate or acrylate production. The OptKnock-generated strains are adaptively evolved in triplicate (running in parallel) due to differences in the evolutionary patterns witnessed previously in E. coli ((Fong and Palsson, Nat Genet, 36:1056-1058 (2004); Fong et al., J Bacteriol, 185:6400-6408 (2003); Ibarra et al., Nature 420: 186-189 (2002)) that could potentially result in one strain having superior production qualities over the others. Evolutions will be run for a period of 2-6 weeks, depending upon the rate of growth improvement attained. In general, evolutions will be stopped once a stable phenotype is obtained.

Following the adaptive evolution process, the new strains are characterized again by measuring the growth rate, the substrate uptake rate, and the product/byproduct secretion rate. These results will be compared to the OptKnock predictions by plotting actual growth and production yields along side the production envelopes in the above figures. The most successful OptKnock design/evolution combinations are chosen to pursue further, and are characterized in lab-scale batch and continuous fermentations. The growth-coupled biochemical production concept behind the OptKnock approach should also result in the generation of genetically stable overproducers. Thus, the cultures are maintained in continuous mode for one month to evaluate long-term stability. Periodic samples are taken to ensure that yield and productivity are maintained throughout the experiment.

As will become evident, the teachings contained herein will enable, in a broader sense, the development of methods for decarboxylating alpha, beta-unsaturated carboxylic acids or their salts through the use of naturally occurring or altered decarboxylases. Such alterations can be introduced through a variety of directed and/or adaptive evolution methods.

In some embodiments, the present invention provides a non-naturally occurring microbial organism, that includes a microbial organism having an olefin pathway having at least one exogenous nucleic acid encoding an olefin pathway enzyme expressed in a sufficient amount to produce an olefin. The olefin pathway includes a decarboxylase. In some embodiments, this exogenous nucleic acid is a heterologous nucleic acid. The microbial organism having this decarboxylase can be optionally cultured under substantially anaerobic conditions.

In other embodiments, the present disclosure provides non-naturally occurring microbial organisms having an acrylate pathway that includes at least one exogenous nucleic acid encoding an acrylate pathway enzyme expressed in a sufficient amount to produce acrylate. This acrylate pathway includes a decarboxylase as described herein below. In particular embodiments, the decarboxylase catalyzes fumarate decarboxylation to provide acrylate. Decarboxylases (also known as carboxy lyases) catalyze the loss of carbon dioxide from an organic compound or a cellular metabolite possessing a carboxylic acid function. Decarboxylases are prevalent in nature and can require either pyridoxal phosphate or pyruvate as a co-factor, although many require no bound co-factors. Over 50 decarboxylase enzymes have been reported and characterized by biochemical and/or analytical methods.

Figure 19:
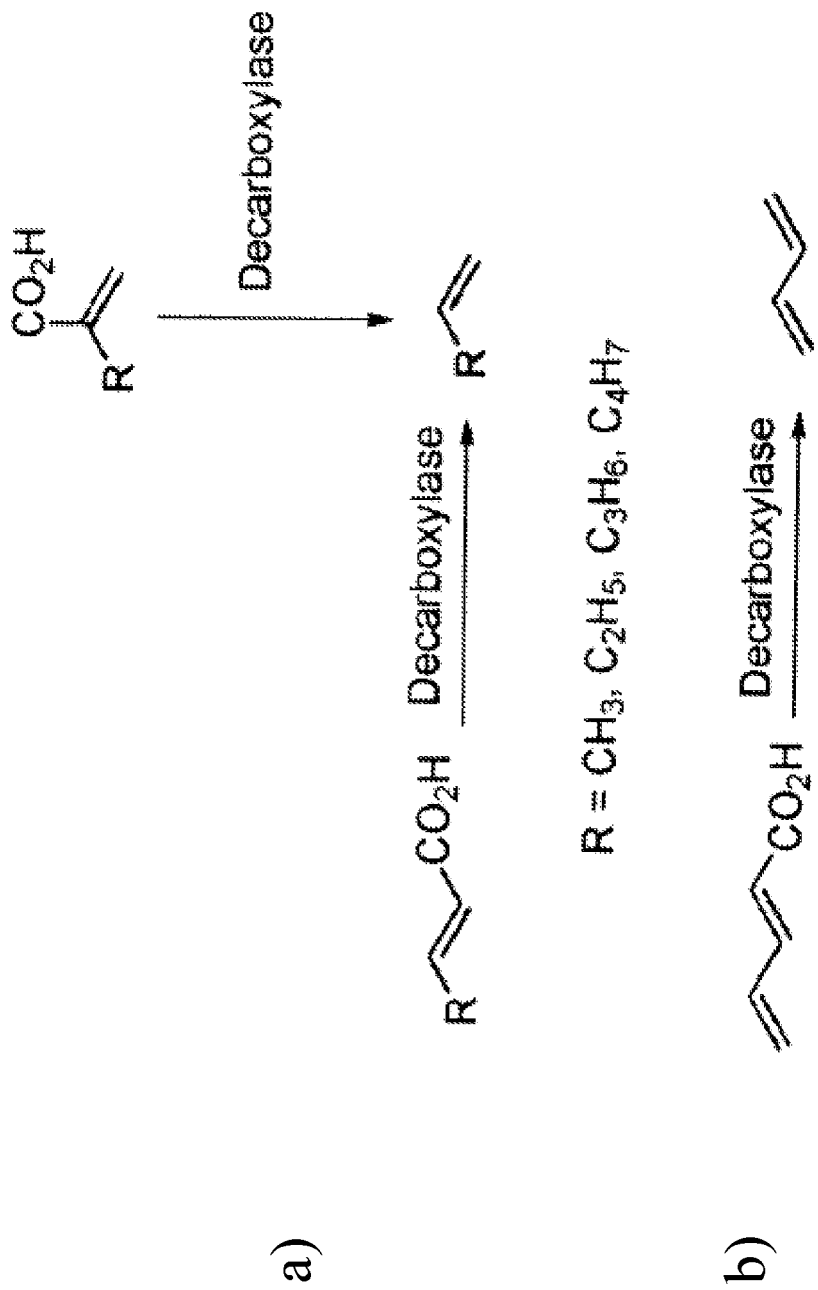
FIG. 19 shows the prophetic transformations of a) 1,1- and 1,2-substituted carboxylic acids to terminal olefins catalyzed by a decarboxylase and b) the transformation of a pentadienoic acid to 1,3-butadiene.
Figures 21A, 21B, 21C, 21D:
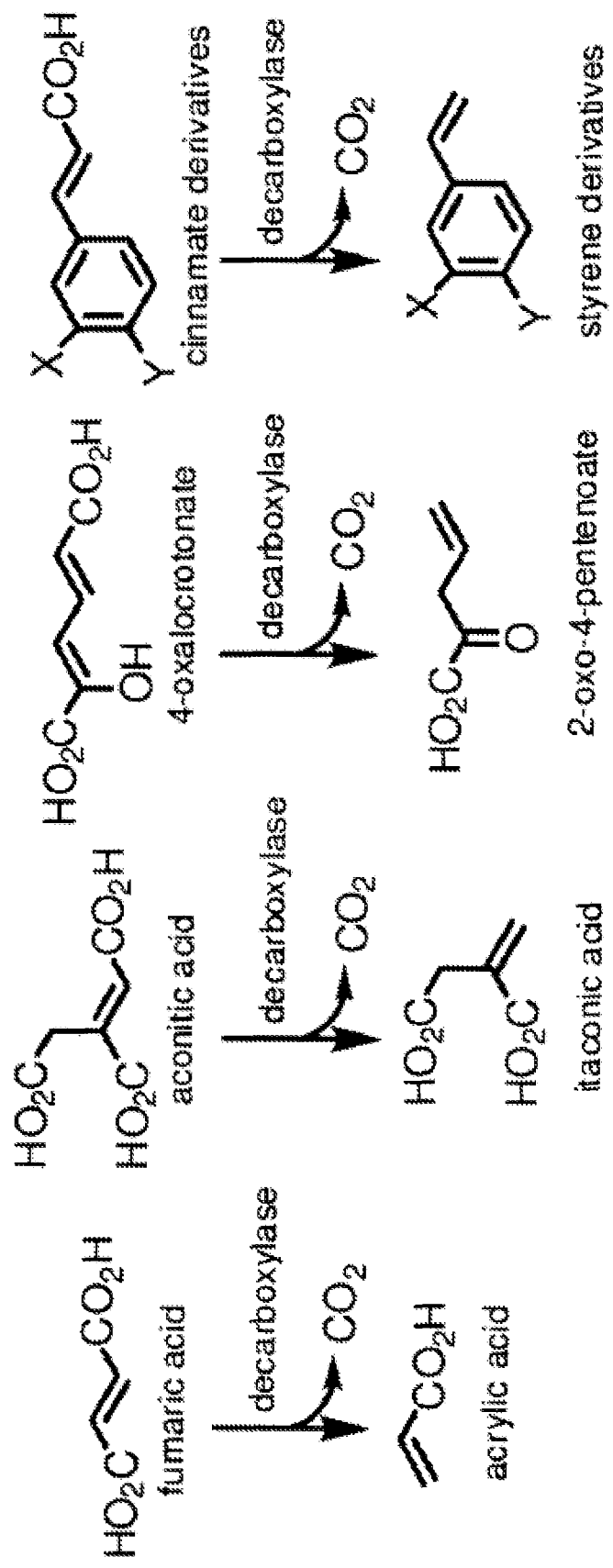
FIG. 21A shows the prophetic transformation of fumarate to acrylate catalyzed by a decarboxylase.
FIG. 21B shows the decarboxylation of aconitate to itaconate catalyzed by aconitate decarboxylase.
FIG. 21C shows the decarboxylation of 4-oxalocrotonate to 2-oxopentenoate catalyzed by 4-oxalocrotonate decarboxylase.
FIG. 21D shows the decarboxylation of cinnamate derivatives to styrene derivatives catalyzed by a decarboxylase.

The process in FIGS. 20 and 21A show the decarboxylation of fumaric acid to acrylic acid. Numerous decarboxylase enzymes have been characterized and shown to decarboxylate structurally similar substrates to fumarate (FIGS. 21B-D). These enzymes are applicable for use in the present invention to decarboxylate fumarate and other unsaturated carboxylic acids, as shown in FIG. 19. One enzyme with closely related function is aconitate decarboxylase (FIG. 21B). This enzyme catalyzes the final step in itaconate biosynthesis in a strain of Candida and also in the filamentous fungus Aspergillus terreus. (Bonnarme et al. J. Bacteriol. 177:3573-3578 (1995); Willke et al. Appl. Microbiol. Biotechnol 56:289-295 (2001)). Aconitate decarboxylase has been purified and characterized from Aspergillus terreus (Dwiarti et al. J. Biosci. Bioeng., 94(1): 29-33 (2002). The gene and protein sequence for the cis-aconitic acid decarboxylase (CAD) enzyme are described in EP2017344 and WO 2009/014437. The protein sequence is listed below along with several close homologs described in EP2017344 and WO2009/014437.

| Gene name | GenBankID | Organism |
| --- | --- | --- |
| CAD | XP_001209273 (GI: 115385453) | Aspergillus terreus |
|  | XP_001217495 (GI: 115402837) | Aspergillus terreus |
|  | XP_001209946 (GI: 115386810) | Aspergillus terreus |
|  | BAE66063 (GI: 83775944) | Aspergillus oryzae |
|  | XP_001393934 (GI: 83775944) | Aspergillus niger |
|  | XP_391316 (GI: 46139251) | Gibberella zeae |
|  | XP_001389415 (GI: 145230213) | Aspergillus niger |
|  | XP_001383451 (GI: 126133853) | Pichia stipitis |
|  | YP_891060 (GI: 118473159) | Mycobacterium smegmatis |
|  | NP_961187 (GI: 41408351) | Mycobacterium avium subsp. pratuberculosis |
|  | YP_880968 (GI: 118466464) | Mycobacterium avium |
|  | ZP_01648681 (GI: 119882410) | Salinispora arenicola |
|  | ZP_01648681 (GI: 119882410) | Salonispora tropica |

Another enzyme type with similar function is 4-oxalocrotonate decarboxylase (FIG. 21C). This enzyme has been isolated from numerous organisms and characterized. Genes encoding this enzyme include dmpH and dmpE in Pseudomonas sp. (strain 600) (Shingler et al. J. Bacteriol. 174:711-724 (1992)), xylII and xylIII from Pseudomonas

*putida* (Kato et al. *Arch. Microbiol.* 168:457-463 (1997); Stanley et al. *Biochemistry* 39:718-726 (2000); Lian et al. *J. Am. Chem. Soc.* 116, 10403-10411 (1994)) and Reut_B5691 and Reut_B5692 from *Ralstonia eutropha* JMP134 (Hughes et al. *J. Bacteriol.* 158:79-83 (1984). The genes encoding the enzyme from *Pseudomonas* sp. (strain 600) have been cloned and expressed in *E. coli* (Shingler et al. *J. Bacteriol.* 174:711-724 (1992)).

Finally, a class of decarboxylases has been characterized that catalyze the conversion of cinnamate (phenylacrylate) and substituted cinnamate derivatives to the corresponding styrene derivatives (FIG. 21D). These enzymes are common in a variety of organisms and specific genes encoding these enzymes that have been cloned and expressed in *E. coli* are: pad 1 from *Saccharomyces cerevisae* (Clausen et al. *Gene* 142:107-112 (1994), pdc from *Lactobacillus plantarum* (Barthelmebs et al. *Appl. Environ. Microbiol.* 67, 1063-1069 (2001); Qi et al. *Metabolic Engineering* 9: 268-276 (2007); Rodriguez et al. *J. Agric. Food Chem.* 56, 3068-3072 (2008)), pofK (pad) from *Klebsiella oxytoca* (Hashidoko et al. *Biosci. Biotech. Biochem.* 58, 217-218 (1994); Uchiyama et al. *Biosci. Biotech. Biochem.* 72: 116-123 (2008)), and *Pedicoccus pentosaceus* (Barthelmebs et al. *J. Bacteriol.* 182: 6724-6731 (2000); Barthelmebs et al. *Appl. Environ. Microbiol.* 67: 1063-1069 (2001)), and padC from *Bacillus subtilis* and *Bacillus pumilus* (Barthelmebs et al. 2001 supra; Qi, et al supra). A ferulic acid decarboxylase from *Pseudomonas fluorescens* also has been purified and characterized (Huang et al. *J Bacteriol.* 176: 5912-5918 (1994)). Importantly, this class of enzymes have been shown to be stable and do not require either exogenous or internally bound co-factors, thus making these enzymes ideally suitable for biotransformations (Sariaslani *Annu. Rev. Microbiol.* 61: 51-69 (2007)). A summary of genes encoding these various decarboxylases for carrying out the transformations shown in FIGS. 21B-21D are shown below.

| Gene name | GenBankID | Organism |
| --- | --- | --- |
| dmpH | CAA43228.1 (GI: 45685) | *Pseudomonas* sp. CF600 |
| dmpE | CAA43225.1 (GI: 45682) | *Pseudomonas* sp. CF600 |
| xylII | YP_709328.1 (GI: 111116444) | *Pseudomonas putida* |
| xylIII | YP_709353.1 (GI: 111116469) | *Pseudomonas putida* |
| Reut_B5691 | YP_299880.1 (GI: 73539513) | *Ralstonia eutropha* JMP134 |
| Reut_B5692 | YP_299881.1 (GI: 73539514) | *Ralstonia eutropha* JMP134 |
| pad1 | AB368798 (GI: 188496948) | *Saccharomyces cerevisae* |
| pdc | U63827 (GI: 1762615) | *Lactobacillus plantarum* |
| pofK (pad) | AB330293 (GI: 149941607) | *Klebsiella oxytoca* |
| padC | AF017117 (GI: 2394281) | *Bacillus subtilis* |
| pad | AJ276891 (GI: 11322456) | *Pedicoccus pentosaceus* |
| pad | AJ278683 (GI: 11691809) | *Bacillus pumilus* |

Each of the decarboxylases listed above represents a suitable enzyme for the transformation shown in FIGS. 20 and 21A. If the desired activity or productivity of the enzyme is not observed in the conversion of fumarate to acrylate, or if acrylic acid production inhibits the decarboxylase enzymes, the decarboxylase enzymes can be evolved using known protein engineering methods to achieve the required performance. Importantly, it was shown through the use of chimeric enzymes that the C-terminal region of decarboxylases appears to be responsible for substrate specificity (Barthelmebs et al. (2001) supra). Accordingly, directed evolution experiments to broaden the specificity of decarboxylases in order to gain activity with fumarate can be focused on the C-terminal region of these enzymes.

Some of the decarboxylases can exhibit higher activity on the cis-isomer of fumarate known as maleate. Fumarate can be converted to maleate by maleate cis-trans isomerase encoded by the maiA gene from *Alcaligenes faecalis* (Hatakeyama, et al., *Biochem. Biophys. Research Comm.* 239, 74-79 (1997)) or similar genes that can be identified by sequence homology including those from *Geobacillus stearothermophilus* and *Ralstonia pickettii* 12D. Additional maleate cis-trans isomerase enzymes are encoded by the enzymes whose amino acid sequences are described (SEQ ID NO:1-4) in U.S. Pat. No. 6,133,014, which is incorporated by reference in its entirety. Useful GenBank information for some of these isomerases is shown below.

| Gene name | GenBankID | Organism |
| --- | --- | --- |
| maiA | BAA23002.1 (GI: 2575787) | *Alcaligenes faecalis* |
| maiA | BAA77296 (GI: 4760466) | *Geobacillus stearothermophilus* |
| Rpic12DDRAFT_0600 | ZP_02009633 (GI: 153888491) | *Ralstonia pickettii* 12D |

The exogenous nucleic acid encoding the decarboxylase can come from another organism such as those described above, thus providing a heterologous nucleic acid. Alternatively, in the case of a microbial organism that already has a native decarboxylase capable of decarboxylating fumarate, additional copies of the decarboxylase can be introduced to increase its expression. In addition to incorporating a decarboxylase, a non-naturally occurring microbial organism will have certain energy requirements for growth and maintenance as outlined below.

Engineering the capability for fumarate decarboxylation into *Escherichia coli*, for example, results in a redox-balanced pathway for the production of acrylate from carbohydrates. Provided that symport of the acrylate monoanion is the predominant means of product export, the pathway as depicted in FIG. 20 can be energetically negative because the high energy phosphate bond contained in each PEP molecule gained from glycolysis will be lost upon conversion to oxaloacetate by PEP carboxylase, a native *E. coli* enzyme that is functional during growth on carbohydrates.

This energetic limitation can be remedied by either supplying a limited amount of an external electron acceptor such as oxygen or nitrate to enable energy generation via respiration, or by at least two strain engineering strategies provided herein below. Either strain engineering method ensures that the pathway for production of acrylate via fumarate decarboxylase generates sufficient energy to support cell growth and maintenance under anaerobic or aerobic conditions. Although the non-naturally occurring microbial organism can be grown under aerobic or anaerobic conditions, a substantially anaerobic culture medium is preferred. The two exemplary designs described below can be implemented in order to generate the requisite energy for growth and maintenance under anaerobic conditions.

In one embodiment, a non-naturally occurring microbial organism can include an exogenous nucleic acid encoding at least one malic enzyme to supply the requisite energy for growth and maintenance. Malic enzymes for this purpose can include, without limitation, malic enzyme (NAD-dependent) and malic enzyme (NADP-dependent). For example, one of the native *E. coli* malic enzymes (Takeo, K., *J Biochem.* 66:379-387 (1969)) or a similar non-native enzyme with higher activity can be expressed to enable the conversion of pyruvate and $CO_2$ to malate. By fixing carbon to pyruvate as opposed to PEP, malic enzyme enables the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl Environ Microbiol* 63:2695-2701 (1997)). Thus, in some embodiments the non-naturally occurring microbial organism can include an exogenous nucleic acid providing a gene such as maeA. A similar observation was made upon overexpressing the malic enzyme from *Ascaris suum* in *E. coli* (Stols et al., *Appl Biochem. Biotechnol* 63-65:153-158 (1997)). The second *E. coli* malic enzyme, encoded by maeB, is NADP-dependent and also decarboxylates oxaloacetate and other alpha-keto acids (Iwakura et al., *J Biochem.* 85:1355-1365 (1979)) Therefore, in other embodiments the non-naturally occurring microbial organism can include an exogenous nucleic acid providing a gene such as maeB. The relevant malic enzyme gene information is shown below.

| Gene name | Organism | Accession Number |
|---|---|---|
| maeA | E. coli | NP_415996 (GI: 90111281) |
| maeB | E. coli | NP_416958 (GI: 16130388) |
| NAD-ME | Ascaris suum | P27443 (GI: 126732) |

Another option for providing an energetically favorable pathway involves introducing a reversible phosphoenolpyruvate kinase (PPCK) enzyme, which unlike PEP carboxylase, can generate one ATP per phosphoenolpyruvate molecule converted to oxaloacetate. In some embodiments, the non-naturally occurring microbial organism can also include an exogenous nucleic acid encoding a phosphoenolpyruvate carboxykinase. PEP carboxykinase is known to produce oxaloacetate from PEP in rumen bacteria such as *Mannheimia succiniciproducens* (Hong et al., *Nat Biotechnol* 22:1275-1281 (2004)) However, the role of PEP carboxykinase, encoded by pck, in producing oxaloacetate in *E. coli* is believed to be minor as compared to PEP carboxylase, possibly due to the higher $K_m$ for bicarbonate of PEP carboxykinase (Kim et al., *Appl Environ Microbiol* 70:1238-1241 (2004)) Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. In addition, examples of non-native PEP carboxykinase genes that have been cloned and shown to function in *E. coli* include those from *M. succiniciproducens* (Lee et al., *Gene. Biotechnol. Bioprocess Eng.* 7:95-99 (2002)), *Anaerobiospirillum succiniciproducens* (Laivenieks et al. *Appl Environ Microbiol* 63:2273-2280 (1997)), and *Actinobacillus succinogenes* (Kim et al., *Appl Environ Microbiol* 70:1238-1241 (2004)). The relevant PEP carboxykinase gene information is shown below.

| Gene name | Organism | Accession Number |
|---|---|---|
| pck | E. coli | NP_417862 (GI: 16131280) |
| pckA | Mannheimia succiniciproducens | YP_089485 (GI: 52426348) |
| pckA | Anaerobiospirillum succiniciproducens | O09460 (GI: 3122621) |
| pck | Actinobacillus succinogenes | ABX39017 (GI: 160415396) |

In addition to the supplying the requisite energy as described above, the formation of acrylate can also be optimized by modifying the non-naturally occurring microbial organism's metabolic production of fumarate. Toward this end, the non-naturally occurring microbial organism can include one or more gene disruptions in addition to the inserted nucleic acid sequences outline above. Gene disruptions can result from, for example, single nucleotide insertion or deletions, stable mutations, and complete gene deletions. Exemplary pathway designs are described below.

The non-naturally occurring microbial organisms that synthesize acrylate can be produced by introducing expressible nucleic acids encoding one or more of the enzymes or proteins participating in one or more acrylate biosynthetic pathways. Depending on the host microbial organism chosen for biosynthesis, nucleic acids for some or all of a particular acrylate biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve acrylate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as acrylate.

Depending on the acrylate biosynthetic pathway constituents of a selected host microbial organism, the non-naturally occurring microbial organisms of the invention will include at least one exogenously expressed acrylate pathway-encoding nucleic acid and up to all encoding nucleic acids for one or more acrylate biosynthetic pathways. For example, acrylate biosynthesis can be established in a host deficient in a pathway enzyme or protein through exogenous expression of the corresponding encoding nucleic acid. In a host deficient in all enzymes or proteins of an acrylate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of acrylate can be included, such as a decarboxylase.

Given the teachings and guidance provided herein, those skilled in the art will understand that the number of encoding nucleic acids to introduce in an expressible form will, at least, parallel the acrylate pathway deficiencies of the selected host microbial organism. Therefore, a non-naturally occurring microbial organism of the invention can have one, two, three, four, up to all nucleic acids encoding the enzymes or proteins constituting an acrylate biosynthetic pathway disclosed herein. In some embodiments, the non-naturally occurring microbial organisms also can include other genetic modifications that facilitate or optimize acrylate biosynthesis or that confer other useful functions onto the host microbial organism. One such other functionality can include, for example, augmentation of the synthesis of one or more of the acrylate pathway precursors such as fumarate.

Generally, a host microbial organism is selected such that it produces the precursor of an acrylate pathway, either as a naturally produced molecule or as an engineered product that either provides de novo production of a desired precursor or increased production of a precursor naturally produced by the host microbial organism. For example, fumarate is produced naturally in a host organism such as E. coli. A host organism can be engineered to increase production of a precursor, as disclosed herein. In addition, a microbial organism that has been engineered to produce a desired precursor can be used as a host organism and further engineered to express enzymes or proteins of an acrylate pathway.

In some embodiments, a non-naturally occurring microbial organism of the invention is generated from a host that contains the enzymatic capability to synthesize acrylate. In this specific embodiment it can be useful to increase the synthesis or accumulation of an acrylate pathway product to, for example, drive acrylate pathway reactions toward acrylate production. Increased synthesis or accumulation can be accomplished by, for example, overexpression of nucleic acids encoding one or more of the above-described acrylate pathway enzymes or proteins. Over expression the enzyme or enzymes and/or protein or proteins of the acrylate pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing acrylate, through overexpression of one, two, three, four, five, that is, up to all nucleic acids encoding acrylate biosynthetic pathway enzymes or proteins. In addition, a non-naturally occurring organism can be generated by mutagenesis of an endogenous gene that results in an increase in activity of an enzyme in the acrylate biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an acrylate biosynthetic pathway onto the microbial organism. Alternatively, encoding nucleic acids can be introduced to produce an intermediate microbial organism having the biosynthetic capability to catalyze some of the required reactions to confer acrylate biosynthetic capability. For example, a non-naturally occurring microbial organism having an acrylate biosynthetic pathway can comprise at least one exogenous nucleic acids encoding desired enzymes or proteins, such as a decarboxylase, and the like.

In addition to the biosynthesis of acrylate as described herein, the non-naturally occurring microbial organisms and methods of the invention also can be utilized in various combinations with each other and with other microbial organisms and methods well known in the art to achieve product biosynthesis by other routes. For example, one alternative to produce acrylate other than use of the acrylate producers is through addition of another microbial organism capable of converting an acrylate pathway intermediate to acrylate. One such procedure includes, for example, the fermentation of a microbial organism that produces an acrylate pathway intermediate. The acrylate pathway intermediate can then be used as a substrate for a second microbial organism that converts the acrylate pathway intermediate to acrylate. The acrylate pathway intermediate can be added directly to another culture of the second organism or the original culture of the acrylate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, acrylate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of acrylate can be accomplished by constructing a microbial organism that contains biosynthetic pathways for conversion of one pathway intermediate to another pathway intermediate or the product. Alternatively, acrylate also can be biosynthetically produced from microbial organisms through co-culture or co-fermentation using two organisms in the same vessel, where the first microbial organism produces a fumarate intermediate and the second microbial organism converts the intermediate to acrylate.

Microorganisms capable of directly producing acrylate are constructed by introducing genes encoding decarboxylase enzymes into the strains engineered as described above for maximal fumarate production. The following example describes the creation of a microbial organism that can produce acrylic acid from renewable feedstocks such as glucose or sucrose.

To generate an *E. coli* strain engineered to produce acrylate or acrylic acid, nucleic acids encoding the decarboxylase enzymes are cloned and expressed in *E. coli* capable of overproducing fumarate using well known molecular biology techniques and recombinant and detection methods well known in the art. Such methods are described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

An acrylate producing strain is constructed, by cloning the individual phenylacrylic acid decarboxylase genes pad1 (AB368798), pdc (U63827), pofK (AB330293), padC (AF017117), pad (AJ276891), and pad (AJ278683) into pZA33 or pZE13 vectors (Expressys, Ruelzheim, Germany) under the IPTG-titratable PA1/lacO promoter. The plasmids are transformed into the fumarate overproducing *E. coli* strain using standard methods such as electroporation. The resulting genetically engineered organism is cultured in glucose-containing medium following procedures well known in the art (see, for example, Sambrook et al., supra, 2001). Expression of the decarboxylase genes are corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce acrylic acid is confirmed using HPLC, gas chromatography-mass spectrometry (GCMS) and/or liquid chromatography-mass spectrometry (LCMS).

Microbial strains engineered to have a functional acrylic acid synthesis pathway are further augmented by optimization for efficient utilization of the pathway. Briefly, the engineered strain is assessed to determine whether exogenous genes are expressed at a rate limiting level. Flux analysis using $^{13}$C-labeled glucose is performed to assess bottlenecks in the system. Expression is increased for enzymes produced at low levels and that limit the flux through the pathway by, for example, introduction of additional gene copy numbers or changes to the promoter and ribosome binding sites.

To generate better acrylate producers, metabolic modeling is utilized to optimize growth conditions. Modeling is also used to design gene knockouts that additionally optimize utilization of the pathway, as described above. Modeling analysis allows reliable predictions of the effects on cell growth of shifting the metabolism towards more efficient production of acrylic acid. Adaptive evolution is performed to improve both growth and production characteristics (Fong and Palsson, *Nat Genet*. 36:1056-1058 (2004)). Based on the results, subsequent rounds of modeling, genetic engineering and adaptive evolution can be applied to the acrylic acid producer to further increase production.

For large-scale production of acrylic acid, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained in the optimum range by addition of acids such as $H_2SO_4$ or bases such as NaOH or $Na_2CO_3$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

*E. coli* and other microorganisms are known to possess fatty acid and organic acid degradation pathways that could lead to acrylate degradation. While fermentative production of acrylic acid under anaerobic conditions should not be accompanied by degradation, should product degradation be observed, the pathways responsible for product degradation will be deleted.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce acrylate.

Sources of encoding nucleic acids for an acrylate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Candida albicans, Candida boidinii, Aspergillus terreus, Pseudomonas* sp. CF600, *Pseudomonas putida, Ralstonia eutropha* JMP134, *Saccharomyces cerevisae, Lactobacillus plantarum, Klebsiella oxytoca, Bacillus subtilis, Bacillus pumilus, Pedicoccus pentosaceus*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite acrylate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of acrylate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative acrylate biosynthetic pathway exists in an unrelated species, acrylate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms can differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize acrylate.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*. *E. coli* is a particularly useful host organism since it is a well characterized microbial organism suitable for genetic engineering. Other particularly useful host organisms include yeast such as *Saccharomyces cerevisiae*.

Methods for constructing and testing the expression levels of a non-naturally occurring acrylate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of acrylate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more acrylate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, a method for producing acrylate, includes culturing a non-naturally occurring microbial organism having an acrylate pathway. The pathway includes at least one exogenous nucleic acid encoding an acrylate pathway enzyme expressed in a sufficient amount to produce acrylate under conditions and for a sufficient period of time to produce acrylate. Ideally, the non-naturally occurring microbial organism is in a substantially anaerobic culture medium as described above.

The acrylate pathway includes a decarboxylase gene introduced into an organism that is engineered to produce high levels of fumaric acid under anaerobic conditions from carbon substrates such as glucose or sucrose. Expression of active decarboxylases for the production of chemicals previously has been demonstrated in *E. coli* (Sariaslani, F. S., *Annu. Rev. Microbiol.* 61:51-69 (2007)). In this scenario, decarboxylation of fumaric acid occurs intracellularly and acrylate is produced directly and is secreted from the cell and recovered through standard methods employed for acid separation and purification.

One challenge with direct acrylate production could be the known cellular toxicity of acrylic acid and acrylate salts (Straathof et al., *Appl. Microbiol. Biotechnol.* 67:727-734 (2005)). Selection of an appropriate production organism involves detailed acrylate toxicity assessment in order to determine inherent levels of tolerance. In addition, adaptive evolution methods are applied to the production host to increase tolerance to acrylate up to the required levels of acrylate (e.g., 5-10% final titers). Previous studies have found evolution to be useful for increasing tolerance of microorganisms to organic acids (Steiner 2003; Patnaik 2002). It has been estimated that production of at least 50 g/L acrylate should be possible through fermentation processes (Straathof et al., *Appl. Microbiol. Biotechnol.* 67, 727-734 (2005)).

Should the toxicity of acrylate prove too high for effective production (the world wide web at toxnet.nlm.nih.gov/cgi-bin/sis/search/r?dbs+hsdb:@term+@rn+@rel+79-10-7 indicates that toxicity to bacteria is low), a second approach involves primary production and secretion of fumarate into a fermentation broth, followed by secondary addition of separately produced decarboxylase enzyme. This approach allows effective conversion of fumarate to acrylate without concern for cell viability. Subsequent processing will be the same as above, involving separation and purification of acrylic acid directly from the broth with no need to separate or isolate fumaric acid prior to treatment with decarboxylase.

An alternative to this production mode is to engineer a decarboxylase enzyme so that it is secreted from the fumarate-producing cell, in which case acrylate production occurs in the same vessel as fumarate production. This approach is particularly effective if decarboxylase enzyme production and secretion are subject to inducible programming (e.g., using a temperature sensitive promoter) such that the enzyme is produced and secreted into the broth following completion of fumarate production.

Thus, in some embodiments, the present invention provides a method for producing acrylate, that includes culturing a first non-naturally occurring microbial organism having one or more gene disruptions. Again, the one or more gene disruptions can occur in one or more genes encoding one or more enzymes obligatory to coupling fumarate production to growth of the microorganism when the disruptions reduce an activity of the enzymes such that the disruptions confer stable growth-coupled production of fumarate. Finally, one adds a decarboxylase to the cultured first non-naturally occurring microbial organism, said decarboxylase catalyzing the decarboxylation of fumarate.

In some embodiments, the decarboxylase is expressed in a second non-naturally occurring microbial organism. In such an instance, the first and second non-naturally occurring microbial organisms can be co-cultured. Additionally, the decarboxylase can also be secreted by a second non-naturally occurring microbial organism which still allows for the first and second microbial organisms to be co-cultured.

Suitable purification and/or assays to test for the production of acrylate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The acrylate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the acrylate producers can be cultured for the biosynthetic production of acrylate.

For the production of acrylate, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can be, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of acrylate.

In addition to renewable feedstocks such as those exemplified above, the acrylate microbial organisms of the invention also can be modified for growth on syngas as its source of carbon. In this specific embodiment, one or more proteins or enzymes are expressed in the acrylate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

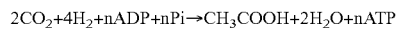

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: cobalamide corrinoid/iron-sulfur protein, methyltransferase, carbon monoxide dehydrogenase, acetyl-CoA synthase, acetyl-CoA synthase disulfide reductase and hydrogenase. Following the teachings and guidance provided herein for introducing a sufficient number of encoding nucleic acids to generate an acrylate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, acrylate and any of the intermediate metabolites in the acrylate pathway. All that is required is to engineer in one or more of the required enzyme or protein activities to achieve biosynthesis of the desired compound or intermediate including, for example, inclusion of some or all of the acrylate biosynthetic pathways. Accordingly, the invention provides a non-naturally occurring microbial organism that produces and/or secretes acrylate when grown on a carbohydrate or other carbon source and produces and/or secretes any of the intermediate metabolites shown in the acrylate pathway when grown on a carbohydrate or other carbon source. The acrylate producing microbial organisms of the invention can initiate synthesis from an intermediate, for example, fumarate.

The non-naturally occurring microbial organisms of the invention are constructed using methods well known in the art as exemplified herein to exogenously express at least one nucleic acid encoding an acrylate pathway enzyme or protein in sufficient amounts to produce acrylate. It is understood that the microbial organisms of the invention are cultured under conditions sufficient to produce acrylate. Following the teachings and guidance provided herein, the non-naturally occurring microbial organisms of the invention can achieve biosynthesis of acrylate resulting in intracellular concentrations between about 0.1-200 mM or more. Generally, the intracellular concentration of acrylate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

The fumarate, malate, or acrylate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the fumarate, malate, or acrylate producers can be cultured for the biosynthetic production of fumarate, malate, or acrylate.

For the production of fumarate, malate, or acrylate, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of fumarate, malate, or acrylate.

In addition to renewable feedstocks such as those exemplified above, the fumarate, malate, or acrylate microbial organisms of the invention also can be modified for growth on syngas as its source of carbon. In this specific embodiment, one or more proteins or enzymes are expressed in the fumarate, malate, or acrylate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

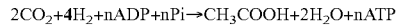

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a fumarate, malate, or acrylate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, fumarate, malate, or acrylate and any of the intermediate metabolites in the fumarate, malate, or acrylate pathway. All that is required is to engineer in one or more of the required enzyme or protein activities to achieve biosynthesis of the desired compound or intermediate including, for example, inclusion of some or all of the fumarate, malate, or acrylate biosynthetic pathways. Accordingly, the invention provides a non-naturally occurring microbial organism that produces and/or secretes fumarate, malate, or acrylate when grown on a carbohydrate or other carbon source and produces and/or secretes any of the intermediate metabolites shown in the fumarate, malate, or acrylate pathway when grown on a carbohydrate or other carbon source. The fumarate, malate, or acrylate producing microbial organisms of the invention can initiate synthesis from any of the aforementioned intermediates.

The non-naturally occurring microbial organisms of the invention are constructed using methods well known in the art as exemplified herein to exogenously express at least one nucleic acid encoding a fumarate, malate, or acrylate pathway enzyme or protein in sufficient amounts to produce fumarate, malate, or acrylate. It is understood that the microbial organisms of the invention are cultured under conditions sufficient to produce fumarate, malate, or acrylate. Following the teachings and guidance provided herein, the non-naturally occurring microbial organisms of the invention can achieve biosynthesis of fumarate, malate, or acrylate resulting in intracellular concentrations between about 0.1-200 mM or more. Generally, the intracellular concentration of fumarate, malate, or acrylate is between about 3-200 mM, particularly between about 10-175 mM and more particularly between about 50-150 mM, including about 50 mM, 75 mM, 100 mM, 125 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the fumarate, malate, or acrylate producers can synthesize fumarate, malate, or acrylate at intracellular concentrations of 5-10 mM or more as well as all other concentrations exemplified herein. It is understood that, even though the above description refers to intracellular concentrations, fumarate, malate, or acrylate producing microbial organisms can produce fumarate, malate, or acrylate intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of fumarate, malate, or acrylate includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of fumarate, malate, or acrylate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of fumarate, malate, or acrylate. Generally, and as with non-continuous culture procedures, the continuous and/or near-continuous production of fumarate, malate, or acrylate can include culturing a non-naturally occurring fumarate, malate, or acrylate producing organism of the invention in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of fumarate, malate, or acrylate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the fumarate, malate, or acrylate producers of the invention for continuous production of substantial quantities of fumarate, malate, or acrylate, the fumarate, malate, or acrylate producers also can be, for example, simultaneously subjected to chemical synthesis procedures to convert the product to other compounds or the product can be separated from the fermentation culture and sequentially subjected to chemical conversion to convert the product to other compounds, if desired.

Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert et al., *Biomol. Eng* 22:11-19 (2005); Huisman et al., Biocatalysis in the pharmaceutical and biotechnology industries, pp. 717-742 (2007) CRC Press, R. N. Patel, Ed.); Otten et al., *Biomol. Eng* 22:1-9 (2005); and Sen et al., *Appl Biochem. Biotechnol* 143:212-223 (2007).) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard et al., *J Theor. Biol.* 234:497-509 (2005).) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii et al., *Nucl. Acids Res* 32:e145 (2004); and Fujii et al., *Nat. Protoc.* 1:2493-2497 (2006).) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, W. P., *Proc Natl Acad Sci U.S.A.* 91:10747-10751 (1994); and Stemmer, W. P., *Nature* 370:389-391 (1994).) typically involves digestion of 2 or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious random neutral mutations that might confer antigenicity.

Staggered Extension (StEP) (Zhao et al., *Nat. Biotechnol* 16:258-261 (1998).) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao et al., *Nucleic Acids Res* 26:681-683 (1998).) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov et al., *Nucleic Acids Res* 27:e18 (1999); and Volkov et al., *Methods Enzymol.* 328:456-463 (2000).) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol* 19:354-359 (2001).) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee et al., *J. Molec. Catalysis* 26:119-129 (2003).) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist et al., *Methods Mol. Biol* 352:191-204 (2007); Bergquist et al., *Biomol. Eng* 22:63-72 (2005); Gibbs et al., *Gene* 271:13-20 (2001).) This can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc Natl Acad Sci US.A* 96:3562-3567 (1999); Ostermeier et al., *Nat. Biotechnol* 17:1205-1209 (1999).) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is almost the same as ITCHY except that phosphothioate dNTPs are used to generate truncations. (Lutz et al., *Nucleic Acids Res* 29:E16 (2001).) Relative to ITCHY, THIO-ITCHY can be easier to optimize, provide more reproducibility, and adjustability.

SCRATCHY—ITCHY combined with DNA shuffling is a combination of DNA shuffling and ITCHY; therefore, allowing multiple crossovers. (Lutz et al. 2001, *Proc Natl Acad Sci U.S.A.* 98:11248-11253 (2001).) SCRATCHY combines the best features of ITCHY and DNA shuffling. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng* 22:63-72 (2005).) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J* 3:74-82 (2008); Wong et al., *Nucleic Acids Res* 32:e26 (2004); and Wong et al., *Anal. Biochem.* 341:187-189 (2005).) Using this technique it can be possible to generate a large library of mutants within 2-3 days using simple methods. This is very non-directed compared to mutational bias of DNA polymerases. Differences in this approach makes this technique complementary (or alternative) to epPCR.

In Synthetic Shuffling, overlapping oligonucleotides are designed to encode "all genetic diversity in targets" and allow a very high diversity for the shuffled progeny. (Ness et al., *Nat. Biotechnol* 20:1251-1255 (2002).) In this technique, one can design the fragments to be shuffled. This aids in increasing the resulting diversity of the progeny. One can design sequence/codon biases to make more distantly related sequences recombine at rates approaching more closely related sequences and it doesn't require possessing the template genes physically.

Nucleotide Exchange and Excision Technology NexT exploits a combination of dUTP incorporation followed by treatment with uracil DNA glycosylase and then piperidine to perform endpoint DNA fragmentation. (Muller et al., *Nucleic Acids Res* 33:e117 (2005).) The gene is reassembled using internal PCR primer extension with proofreading polymerase. The sizes for shuffling are directly controllable using varying dUPT::dTTP ratios. This is an end point reaction using simple methods for uracil incorporation and cleavage. One can use other nucleotide analogs such as 8-oxo-guanine with this method. Additionally, the technique works well with very short fragments (86 bp) and has a low error rate. Chemical cleavage of DNA means very few unshuffled clones.

In Sequence Homology-Independent Protein Recombination (SHIPREC) a linker is used to facilitate fusion between 2 distantly/unrelated genes; nuclease treatment is used to generate a range of chimeras between the two. Result is a single crossover library of these fusions. (Sieber et al., *Nat. Biotechnol* 19:456-460 (2001).) This produces a limited type of shuffling; mutagenesis is a separate process. This technique can create a library of chimeras with varying fractions of each of 2 unrelated parent genes. No homology is needed. SHIPREC was tested with a heme-binding domain of a bacterial CP450 fused to N-terminal regions of a mammalian CP450; this produced mammalian activity in a more soluble enzyme.

In Gene Site Saturation Mutagenesis (GSSM) the starting materials are a supercoiled dsDNA plasmid with insert and 2 primers degenerate at the desired site for mutations. (Kretz et al., *Methods Enzymol.* 388:3-11 (2004).) Primers carry the mutation of interest and anneal to the same sequence on opposite strands of DNA; mutation in the middle of the primer and ~20 nucleotides of correct sequence flanking on each side. The sequence in the primer is NNN or NNK (coding) and MNN (noncoding) (N=all 4, K=G, T, M=A, C). After extension, Dpnl is used to digest dam-methylated DNA to eliminate the wild-type template. This technique explores all possible amino acid substitutions at a given locus (i.e., one codon). The technique facilitates the generation of all possible replacements at one site with no nonsense codons and equal or near-equal representation of most possible alleles. It does not require prior knowledge of structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson et al., *Methods Enzymol.* 208: 564-586 (1991); and Reidhaar-Olson et al., *Science* 241:53-57 (1988).) Simultaneous substitutions at 2 or 3 sites are possible using this technique. Additionally, the method tests a large multiplicity of possible sequence changes at a limited range of sites. It has been used to explore the information content of lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz et al., *Angew. Chem. Int. Ed Engl.* 40:3589-3591 (2001).) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional is mutator plasmids allow increases of 20- to 4000-X in random and natural mutation frequency during selection and to block accumulation of deleterious mutations when selection is not required. (Selifonova et al., *Appl Environ Microbiol*

67:3645-3649 (2001).) This technology is based on a plasmid-derived mutD5 gene, which encodes a mutant subunit of DNA polymerase III. This subunit binds to endogenous DNA polymerase III and compromises the proofreading ability of polymerase III in any of the strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows plasmid curing at 41° C. It should be noted that mutator strains have been explored for quite some time (e.g., see Winter and coworkers, *J. Mol. Biol.* 260:359-3680 (1996). In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal et al., *Proc Natl Acad Sci U.S.A* 102:8466-8471 (2005.) Rather than saturating each site with all possible amino acid changes, a set of 9 is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and should increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (on the world-wide web at verenium.com/Pages/Technology/EnzymeTech/TechEnzyTGR.html) Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM, a large range of mutations can be tested for improved activity. The method allows "blending" and "fine tuning" of DNA shuffling, e.g. codon usage can be optimized.

In Silico Protein Design Automation PDA is an optimization algorithm that anchors the structurally defined protein backbone possessing a particular fold, and searches sequence space for amino acid substitutions that can stabilize the fold and overall protein energetics. (Hayes et al., *Proc Natl Acad Sci U.S.A.* 99:15926-15931 (2002).) This technology allows in silico structure-based entropy predictions in order to search for structural tolerance toward protein amino acid variations. Statistical mechanics is applied to calculate coupling interactions at each position—structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). Choice of sequence variants to test is related to predictions based on most favorable thermodynamics and ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves 1) Use knowledge of structure/function to choose a likely site for enzyme improvement. 2) Saturation mutagenesis at chosen site using Stratagene QuikChange (or other suitable means). 3) Screen/select for desired properties. 4) With improved clone(s), start over at another site and continue repeating. (Reetz et al., *Nat. Protoc.* 2:891-903 (2007); and Reetz et al., *Angew. Chem. Int. Ed Engl.* 45:7745-7751 (2006).) This is a proven methodology assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

To generate better producers, metabolic modeling can be utilized to optimize growth conditions. Modeling can also be used to design gene disruptions that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of fumarate, malate, or acrylate.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

It is understood that modifications which do not substantially affect the activity of the various embodiments of this invention are also included within the definition of the invention provided herein. Accordingly, the following examples are intended to illustrate but not limit the present invention.

Example I

Microorganisms Having Growth-Coupled Production of Fumarate

This Example describes the construction in silico designed strains for the increased production of fumarate in E. Coll.

*Escherichia coli* K-12 MG1655 serves as the wild-type strain into which the deletions are introduced. The strains are constructed by incorporating in-frame deletions using homologous recombination via the λ Red recombinase system of Datsenko and Wanner. (Datsenko and Wanner, *Proc Natl Acad Sci US.A.,* 97(12):6640-5 (2000).) The approach involves replacing a chromosomal sequence (i.e., the gene targeted for removal) with a selectable antibiotic resistance gene, which itself is later removed. Knockouts are integrated one by one into the recipient strain. No antibiotic resistance markers will remain after each deletion allowing accumulation of multiple mutations in each target strain. The deletion technology completely removes the gene targeted for removal so as to substantially reduce the possibility of the constructed mutants reverting back to the wild-type.

As described further below, one exemplary growth condition for achieving biosynthesis of fumarate/malate includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, fumarate, malate, and other organic acid byproducts in the culture supernatant are determined by HPLC using an HPX-87H column (BioRad), and are used to calculate uptake and secretion rates. All experiments are performed with triplicate cultures.

The knockout strains can exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model. (Fong and Palsson, *Nat Genet*, 36(10):1056-8 (2004).)

Should the OptKnock predictions prove successful; the growth improvements brought about by adaptive evolution will be accompanied by enhanced rates of fumarate and/or malate production. The OptKnock-generated strains are adaptively evolved in triplicate (running in parallel) due to differences in the evolutionary patterns witnessed previously in *E. coli* (Fong and Palsson, *Nat Genet*, 36(10):1056-8 (2004); Fong et al., *J Bacteriol*, 185(21):6400-6408 (2003); Ibarra et al., *Nature* 420:186-189 (2002)) that could potentially result in one strain having superior production qualities over the others. Evolutions are run for a period of 2-6 weeks, depending upon the rate of growth improvement attained. In general, evolutions are stopped once a stable phenotype is obtained.

The adaptive evolution procedure involves maintaining the cells in prolonged exponential growth by the serial passage of batch cultures into fresh medium before the stationary phase is attained. Briefly, one procedure allows cells to reach mid-exponential growth ($A_{600}$=0.5) before being diluted and passed to fresh medium (i.e., M9 minimal media with 2 g/L carbon source). This process is repeated, allowing for about 500 generations for each culture. Culture samples are taken, frozen with liquid nitrogen, and the optical culture density recorded for each day throughout the course of the evolutions. The conditions required for each evolution are summarized on table 7. The evolutions are performed in triplicate (i.e., 18 evolutions total) due to differences in the evolutionary patterns witnessed previously Donnelly et al., *Appl Biochem Biotechnol* 70-72: 187-98 (1998); Vemuri et al., *Appl Environ Microbiol* 68:1715-27 (2002), that could potentially result in one strain having superior production qualities over the others. The adaptive evolution step can take up to about two months or more. The adaptive evolution step also can be less than two months depending on the strain design, for example.

Another process can evolve cells using automation technology and is commercially available by Evolugate, LLC (Gainesville, Fla.) under a service contract. The procedure employs the Evolugator™ evolution machine which results in significant time and effort savings over non-automated evolution techniques. Cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat for evolution of cell fitness[25]. In contrast to a chemostat, which maintains cells in a single vessel, the machine operates by moving from one "reactor" to the next in subdivided regions of a spool of tubing, thus eliminating any selection for wall-growth. Culture samples are taken, frozen with liquid nitrogen, and the optical culture density recorded each day throughout the course of the evolutions. The Evolugator is used for each strain until a stable growth rate is achieved. Growth rate improvements of nearly 50% have been observed in two weeks using this device. The above-described strains are adaptively evolved in triplicate (running in parallel). At ten day intervals, culture samples are taken from the Evolugator, purified on agar plates, and cultured in triplicate as discussed above to assess strain physiology.

Following the adaptive evolution process, the new strains are again characterized by measuring the growth rate, the substrate uptake rate, and the product/byproduct secretion rate. These results are compared to the OptKnock predictions by plotting actual growth and production yields along side the production envelopes. The most successful OptKnock design/evolution combinations are chosen to pursue further, and is characterized in lab-scale batch and continuous fermentations. The growth-coupled biochemical production concept behind the OptKnock approach should also result in the generation of genetically stable overproducers. Thus, the cultures can be maintained in continuous mode for one month to evaluate long-term stability. Periodic samples will be taken to ensure that yield and productivity are maintained throughout the experiment.

Example II

Microorganisms Having Growth-Coupled Production of Fumarate

This Example describes the construction in silico designed strains for the increased production of fumarate in *S. cerevisiae*.

Gene deletions are introduced into wild-type, haploid *S. cerevisiae* by homologous recombination of the gene interrupted by the KanMX cassette, flanked by loxP sites enabling removal and recycling of the resistance marker (Wach, A., et al., *PCR-based gene targeting in Saccharomyces cerevisiae*, in *Yeast Gene Analysis*, M. F. Tuite, Editor. 1998, Academic Press: San Diego.). Starting with a loxP-kanMX-loxP sequence on a plasmid, an artificial construct with this sequence flanked by fragments of the gene of interest will be created by PCR using primers containing both 45-50 bp target sequence followed by a region homologous to the above cassette. This linear DNA will be transformed into wild-type *S. cerevisiae*, and recombinants will be selected by geneticin resistance. Colonies will be purified and tested for correct double crossover by PCR. To remove the KanMX marker, a plasmid containing the Cre recombinase and bleomycin resistance will be introduced, promoting recombination between the loxP sites (Gueldener et al., *Nucleic Acids Res.* 30:e23 (2002)). Finally, the resulting strain can be cured of the Cre plasmid by successive culturing on media without any antibiotic present. The final strain will have a markerless gene deletion, and thus the same method can be used to introduce multiple deletions in the same strain.

As described further below, one exemplary growth condition for achieving biosynthesis of fumarate includes anaerobic culture or fermentation conditions. In certain embodiments, the non-naturally occurring eukaryotic organism of the invention can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. One skilled in the art will recognize substantially anaerobic conditions include microaerobic conditions. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, fumarate, malate, and other organic acid byproducts in the culture supernatant are determined by HPLC using an HPX-87H column (BioRad), and are used to calculate uptake and secretion rates. All experiments are performed with triplicate cultures.

The knockout strains can exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model. (Fong and Palsson, *Nat Genet*, 36:1056-1058 (2004).) These teachings can be applied to *S. cerevisiae*.

Should the OptKnock predictions prove successful; the growth improvements brought about by adaptive evolution will be accompanied by enhanced rates of fumarate production, and further strains can be engineered in a similar matter to optimize malate or acrylate production. The OptKnock-generated strains are adaptively evolved in triplicate (running in parallel) due to differences in the evolutionary patterns witnessed previously in *E. coli* (Fong and Palsson, *Nat Genet*, 36:1056-1058 (2004); Fong et al., *J Bacteriol*, 185:6400-6408 (2003); Ibarra et al., *Nature* 420:186-189 (2002)) that could potentially result in one strain having superior production qualities over the others. Evolutions are run for a period of 2-6 weeks, depending upon the rate of growth improvement attained. In general, evolutions are stopped once a stable phenotype is obtained.

The adaptive evolution procedure involves maintaining the cells in prolonged exponential growth by the serial passage of batch cultures into fresh medium before the stationary phase is attained. Briefly, one procedure allows cells to reach mid-exponential growth ($A_{600}$=0.5) before being diluted and passed to fresh medium (i.e., M9 minimal media with 2 g/L carbon source). This process is repeated, allowing for about 500 generations for each culture. Culture samples are taken, frozen with liquid nitrogen, and the optical culture density recorded for each day throughout the course of the evolutions. The evolutions are performed in triplicate due to differences in the evolutionary patterns witnessed previously Donnelly et al., *Appl Biochem Biotechnol* 70-72: 187-98 (1998); Vemuri et al., *Appl Environ Microbiol* 68:1715-27 (2002), that could potentially result in one strain having superior production qualities over the others. The adaptive evolution step can take up to about two months or more. The adaptive evolution step also can be less than two months depending on the strain design, for example.

Another process can evolve cells using automation technology and is commercially available by Evolugate, LLC (Gainesville, Fla.) under a service contract. The procedure employs the Evolugator™ evolution machine which results in significant time and effort savings over non-automated evolution techniques. Cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat for evolution of cell fitness. In contrast to a chemostat, which maintains cells in a single vessel, the machine operates by moving from one "reactor" to the next in subdivided regions of a spool of tubing, thus eliminating any selection for wall-growth. Culture samples are taken, frozen with liquid nitrogen, and the optical culture density recorded each day throughout the course of the evolutions. The Evolugator is used for each strain until a stable growth rate is achieved. Growth rate improvements of nearly 50% have been observed in two weeks using this device. The above-described strains are adaptively evolved in triplicate (running in parallel). At ten day intervals, culture samples are taken from the Evolugator, purified on agar plates, and cultured in triplicate as discussed above to assess strain physiology.

Following the adaptive evolution process, the new strains are again characterized by measuring the growth rate, the substrate uptake rate, and the product/byproduct secretion rate. These results are compared to the OptKnock predictions by plotting actual growth and production yields along side the production envelopes. The most successful OptKnock design/evolution combinations are chosen to pursue further, and is characterized in lab-scale batch and continuous fermentations. The growth-coupled biochemical production concept behind the OptKnock approach should also result in the generation of genetically stable overproducers. Thus, the cultures can be maintained in continuous mode for one month to evaluate long-term stability. Periodic samples will be taken to ensure that yield and productivity are maintained throughout the experiment.

Example III

Acrylate Biosynthesis

This Example describes the generation of a microbial organism capable of producing acrylate using a decarboxylase metabolic pathway.

*Escherichia coli* is used as a target organism to engineer a decarboxylase pathway (FIG. 1), and testing growth and acrylate production from glucose. *E. coli* provides a good model for developing a non-naturally occurring microorganism capable of producing acrylate, from glucose since it is amenable to genetic manipulation and is known to be capable of producing various products, like ethanol, effectively under anaerobic conditions from glucose.

To generate an *E. coli* strain engineered to produce primary alcohol, nucleic acids encoding proteins and enzymes required for the acrylate production pathway via fumarate decarboxylation as described above, are expressed in *E. coli* using well known molecular biology techniques (see, for example, Sambrook, supra, 2001; Ausubel supra, 1999; Roberts et al., supra, 1989). The pad1 gene (AB368798), encoding a decarboxylase under anaerobic conditions, are cloned into the pZE13 vector under the PA1/lacO promoter. The of plasmid is transformed into *E. coli* strain MG1655 to express the enzyme aconitate decarboxylase required for decarboxylation of fumarate to acrylate.

The engineered production organism containing a decarboxylase enzyme is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until acrylate reaches a concentration of between 10-200 g/L, with the cell density being between 5 and 50 g/L. Upon completion of the cultivation period, the fermenter contents are passed through a cell separation unit (e.g., centrifuge) to remove cells and cell debris, and the fermentation broth and acrylate is separated from the broth and purified by standard methods for organic acid recovery.

Example IV

Acrylate from Biologically Produced Fumarate

*Escherichia coli* K-12 MG1655 is used as one reference wild-type strain into which the deletions are introduced. The knockouts are integrated, for example, one-by-one into the recipient strain allowing the accumulation of several deletions. The deletion methodology completely removes the gene targeted for removal so as to avoid the possibility of the constructed mutants reverting back to their wild-type.

The strains are constructed by incorporating in-frame deletions using homologous recombination by well known methods such as the λ Red recombinase system (Datsenko and Wanner, *Proc Natl Acad Sci U.S.A.*, 97:6640-6645 (2000)). The approach involves replacing a chromosomal sequence (i.e., the gene targeted for removal) with a selectable antibiotic resistance gene, which itself is later removed. The knockouts are integrated sequentially into the recipient strain. Antibiotic resistance markers are removed after each deletion, thus allowing accumulation of multiple mutations in each target strain.

An organism engineered for high level fumarate production is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until fumarate reaches a concentration of between 10-200 g/L, with the cell density being between 5 and 50 g/L. Upon completion of the cultivation period, a decarboxylase enzyme is added either directly to the fermenter or after initial removal of cells and cell debris. After agitating for the required length of time required for complete conversion of fumarate to acrylate, the acrylate is recovered as described above.

TABLE 1

The list of all strains identified by OptKnock that are most likely to provide increased fumarate yields in *E. Coli*.

| | |
|---|---|
| 1. | ACKr ADHEr AKGD ASNS2 ATPS4r LDH_D |
| 2. | ACKr ADHEr AKGD ATPS4r CBMK2 LDH_D |
| 3. | ACKr ADHEr AKGD ATPS4r GLUDy LDH_D |
| 4. | ACKr ADHEr AKGD ATPS4r LDH_D |
| 5. | ACKr ADHEr AKGD ATPS4r LDH_D RPE |
| 6. | ACKr ADHEr AKGD ATPS4r LDH_D TAL |
| 7. | ACKr ADHEr AKGD ATPS4r LDH_D TKT1 |
| 8. | ACKr ADHEr AKGD ATPS4r LDH_D TKT2 |
| 9. | ACKr ADHEr ASNS2 ATPS4r LDH_D SUCOAS |
| 10. | ACKr ADHEr ASNS2 LDH_D ME2 SUCD4 |
| 11. | ACKr ADHEr ATPS4r CBMK2 LDH_D SUCOAS |
| 12. | ACKr ADHEr ATPS4r GLUDy LDH_D SUCOAS |
| 13. | ACKr ADHEr ATPS4r LDH_D PDH PFLi |
| 14. | ACKr ADHEr ATPS4r LDH_D RPE SUCOAS |
| 15. | ACKr ADHEr ATPS4r LDH_D SUCOAS |
| 16. | ACKr ADHEr ATPS4r LDH_D SUCOAS TAL |
| 17. | ACKr ADHEr ATPS4r LDH_D SUCOAS TKT1 |
| 18. | ACKr ADHEr ATPS4r LDH_D SUCOAS TKT2 |
| 19. | ACKr ADHEr CBMK2 FRD2 LDH_D ME2 THD2 |
| 20. | ACKr ADHEr CBMK2 LDH_D ME2 SUCD4 |
| 21. | ACKr ADHEr FRD2 G5SD LDH_D ME2 THD2 |
| 22. | ACKr ADHEr FRD2 GLCpts GLUDy LDH_D ME2 |
| 23. | ACKr ADHEr FRD2 GLU5K LDH_D ME2 THD2 |
| 24. | ACKr ADHEr FRD2 LDH_D ME2 PFLi THD2 |
| 25. | ACKr ADHEr FRD2 LDH_D ME2 THD2 |
| 26. | ACKr ADHEr GLCpts GLUDy LDH_D ME2 SUCD4 |
| 27. | ACKr ADHEr GLCpts LDH_D ME2 SUCD4 |
| 28. | ACKr ADHEr GLUDy LDH_D ME2 SUCD4 |
| 29. | ACKr ADHEr LDH_D ME2 SUCD4 |
| 30. | ACKr AKGD ASNS2 ATPS4r |
| 31. | ACKr AKGD ASNS2 ATPS4r CBMK2 |
| 32. | ACKr AKGD ASNS2 ATPS4r GLUDy |
| 33. | ACKr AKGD ASNS2 ATPS4r RPE |
| 34. | ACKr AKGD ASNS2 ATPS4r TAL |
| 35. | ACKr AKGD ASNS2 ATPS4r TKT1 |
| 36. | ACKr AKGD ASNS2 ATPS4r TKT2 |
| 37. | ACKr AKGD ATPS4r |
| 38. | ACKr AKGD ATPS4r CBMK2 |
| 39. | ACKr AKGD ATPS4r CBMK2 GLUDy |
| 40. | ACKr AKGD ATPS4r CBMK2 RPE |
| 41. | ACKr AKGD ATPS4r CBMK2 TAL |
| 42. | ACKr AKGD ATPS4r CBMK2 TKT1 |
| 43. | ACKr AKGD ATPS4r CBMK2 TKT2 |
| 44. | ACKr AKGD ATPS4r GLUDy |
| 45. | ACKr AKGD ATPS4r GLUDy RPE |
| 46. | ACKr AKGD ATPS4r GLUDy TAL |
| 47. | ACKr AKGD ATPS4r GLUDy TKT1 |
| 48. | ACKr AKGD ATPS4r GLUDy TKT2 |
| 49. | ACKr AKGD ATPS4r PPCK PYK |
| 50. | ACKr AKGD ATPS4r RPE |
| 51. | ACKr AKGD ATPS4r TAL |
| 52. | ACKr AKGD ATPS4r TKT1 |
| 53. | ACKr AKGD ATPS4r TKT2 |
| 54. | ACKr ASNS2 ATPS4r CBMK2 SUCOAS |
| 55. | ACKr ASNS2 ATPS4r GLUDy SUCOAS |
| 56. | ACKr ASNS2 ATPS4r RPE SUCOAS |
| 57. | ACKr ASNS2 ATPS4r SUCOAS |
| 58. | ACKr ASNS2 ATPS4r SUCOAS TAL |
| 59. | ACKr ASNS2 ATPS4r SUCOAS TKT1 |
| 60. | ACKr ASNS2 ATPS4r SUCOAS TKT2 |
| 61. | ACKr ATPS4r CBMK2 GLUDy SUCOAS |
| 62. | ACKr ATPS4r CBMK2 RPE SUCOAS |
| 63. | ACKr ATPS4r CBMK2 SUCOAS |
| 64. | ACKr ATPS4r CBMK2 SUCOAS TAL |
| 65. | ACKr ATPS4r CBMK2 SUCOAS TKT1 |

TABLE 1-continued

The list of all strains identified by OptKnock that are most likely to provide increased fumarate yields in E. Coli.

| | |
|---|---|
| 66. | ACKr ATPS4r CBMK2 SUCOAS TKT2 |
| 67. | ACKr ATPS4r FUM PPCK |
| 68. | ACKr ATPS4r GLUDy RPE SUCOAS |
| 69. | ACKr ATPS4r GLUDy SUCOAS |
| 70. | ACKr ATPS4r GLUDy SUCOAS TAL |
| 71. | ACKr ATPS4r GLUDy SUCOAS TKT1 |
| 72. | ACKr ATPS4r GLUDy SUCOAS TKT2 |
| 73. | ACKr ATPS4r MDH PPCK |
| 74. | ACKr ATPS4r PDH PFLi |
| 75. | ACKr ATPS4r PPCK PYK SUCOAS |
| 76. | ACKr ATPS4r RPE SUCOAS |
| 77. | ACKr ATPS4r SUCOAS |
| 78. | ACKr ATPS4r SUCOAS TAL |
| 79. | ACKr ATPS4r SUCOAS TKT1 |
| 80. | ACKr ATPS4r SUCOAS TKT2 |
| 81. | ACKr FRD2 ME1x ME2 PYK |
| 82. | ACKr ME1x ME2 PYK SUCD4 |
| 83. | ADHEr AKGD ASNS2 ATPS4r LDH_D PTAr |
| 84. | ADHEr AKGD ATPS4r CBMK2 LDH_D PTAr |
| 85. | ADHEr AKGD ATPS4r GLUDy LDH_D PTAr |
| 86. | ADHEr AKGD ATPS4r LDH_D PTAr |
| 87. | ADHEr AKGD ATPS4r LDH_D PTAr RPE |
| 88. | ADHEr AKGD ATPS4r LDH_D PTAr TAL |
| 89. | ADHEr AKGD ATPS4r LDH_D PTAr TKT1 |
| 90. | ADHEr AKGD ATPS4r LDH_D PTAr TKT2 |
| 91. | ADHEr ALAR ASNS2 LDH_D ME2 PRO1z SUCD4 |
| 92. | ADHEr ALAR CBMK2 GLUDy LDH_D PRO1z SUCD4 |
| 93. | ADHEr ALAR CBMK2 LDH_D ME2 PRO1z SUCD4 |
| 94. | ADHEr ALAR FUM LDH_D PRO1z SUCD4 |
| 95. | ADHEr ALAR G5SD LDH_D ME2 PRO1z SUCD4 |
| 96. | ADHEr ALAR GLCpts LDH_D ME2 PRO1z SUCD4 |
| 97. | ADHEr ALAR GLU5K LDH_D ME2 PRO1z SUCD4 |
| 98. | ADHEr ALAR GLUDy LDH_D ME2 PRO1z SUCD4 |
| 99. | ADHEr ALAR GLUDy LDH_D PRO1z SUCD4 |
| 100. | ADHEr ALAR GLUDy LDH_D PRO1z SUCD4 THD2 |
| 101. | ADHEr ALAR LDH_D ME2 PRO1z SUCD4 |
| 102. | ADHEr ALAR LDH_D ME2 PRO1z SUCD4 THD2 |
| 103. | ADHEr ASNS2 ATPS4r LDH_D PDH PFLi |
| 104. | ADHEr ASNS2 ATPS4r LDH_D PTAr SUCOAS |
| 105. | ADHEr ASNS2 CBMK2 FRD2 G5SD GLUDy LDH_D |
| 106. | ADHEr ASNS2 CBMK2 FRD2 G5SD LDH_D ME2 |
| 107. | ADHEr ASNS2 CBMK2 FRD2 GLU5K GLUDy LDH_D |
| 108. | ADHEr ASNS2 CBMK2 FRD2 GLU5K LDH_D ME2 |
| 109. | ADHEr ASNS2 CBMK2 FRD2 LDH_D ME2 |
| 110. | ADHEr ASNS2 DAAD LDH_D ME2 PRO1z SUCD4 |
| 111. | ADHEr ASNS2 FRD2 G5SD GLUDy LDH_D |
| 112. | ADHEr ASNS2 FRD2 G5SD GLUDy LDH_D ME2 |
| 113. | ADHEr ASNS2 FRD2 G5SD GLUDy LDH_D THD2 |
| 114. | ADHEr ASNS2 FRD2 G5SD LDH_D ME2 |
| 115. | ADHEr ASNS2 FRD2 G5SD LDH_D ME2 THD2 |
| 116. | ADHEr ASNS2 FRD2 GLU5K GLUDy LDH_D |
| 117. | ADHEr ASNS2 FRD2 GLU5K GLUDy LDH_D ME2 |
| 118. | ADHEr ASNS2 FRD2 GLU5K GLUDy LDH_D THD2 |
| 119. | ADHEr ASNS2 FRD2 GLU5K LDH_D ME2 |
| 120. | ADHEr ASNS2 FRD2 GLU5K LDH_D ME2 THD2 |
| 121. | ADHEr ASNS2 FRD2 LDH_D ME2 |
| 122. | ADHEr ASNS2 FRD2 LDH_D ME2 |
| 123. | ADHEr ASNS2 G5SD GLUDy LDH_D PRO1z SUCD4 |
| 124. | ADHEr ASNS2 G5SD LDH_D ME2 SUCD4 THD2 |
| 125. | ADHEr ASNS2 GLU5K GLUDy LDH_D PRO1z SUCD4 |
| 126. | ADHEr ASNS2 GLU5K LDH_D ME2 SUCD4 THD2 |
| 127. | ADHEr ASNS2 LDH_D ME2 PTAr SUCD4 |
| 128. | ADHEr ATPS4r CBMK2 LDH_D PDH PFLi |
| 129. | ADHEr ATPS4r CBMK2 LDH_D PTAr SUCOAS |
| 130. | ADHEr ATPS4r G5SD LDH_D PDH PFLi |
| 131. | ADHEr ATPS4r GLU5K LDH_D PDH PFLi |
| 132. | ADHEr ATPS4r GLUDy LDH_D PDH PFLi |
| 133. | ADHEr ATPS4r GLUDy LDH_D PTAr SUCOAS |
| 134. | ADHEr ATPS4r LDH_D NADH12 PFLi THD2 |
| 135. | ADHEr ATPS4r LDH_D PDH PFLi |
| 136. | ADHEr ATPS4r LDH_D PDH PFLi PTAr |
| 137. | ADHEr ATPS4r LDH_D PDH PFLi RPE |
| 138. | ADHEr ATPS4r LDH_D PDH PFLi TAL |
| 139. | ADHEr ATPS4r LDH_D PDH PFLi TKT1 |
| 140. | ADHEr ATPS4r LDH_D PDH PFLi TKT2 |
| 141. | ADHEr ATPS4r LDH_D PTAr RPE SUCOAS |
| 142. | ADHEr ATPS4r LDH_D PTAr SUCOAS |
| 143. | ADHEr ATPS4r LDH_D PTAr SUCOAS TAL |
| 144. | ADHEr ATPS4r LDH_D PTAr SUCOAS TKT1 |
| 145. | ADHEr ATPS4r LDH_D PTAr SUCOAS TKT2 |
| 146. | ADHEr CBMK2 DAAD GLUDy LDH_D PRO1z SUCD4 |
| 147. | ADHEr CBMK2 DAAD LDH_D ME2 PRO1z SUCD4 |
| 148. | ADHEr CBMK2 FRD2 G5SD LDH_D ME2 |
| 149. | ADHEr CBMK2 FRD2 GLCpts GLUDy LDH_D ME2 |
| 150. | ADHEr CBMK2 FRD2 GLCpts LDH_D ME2 |
| 151. | ADHEr CBMK2 FRD2 GLU5K LDH_D ME2 |
| 152. | ADHEr CBMK2 FRD2 GLUDy LDH_D |
| 153. | ADHEr CBMK2 FRD2 GLUDy LDH_D ME2 |
| 154. | ADHEr CBMK2 FRD2 GLUDy LDH_D ME2 THD2 |
| 155. | ADHEr CBMK2 FRD2 GLUDy LDH_D THD2 |
| 156. | ADHEr CBMK2 FRD2 LDH_D ME2 |
| 157. | ADHEr CBMK2 FRD2 LDH_D ME2 PFLi THD2 |
| 158. | ADHEr CBMK2 FRD2 LDH_D ME2 PTAr THD2 |
| 159. | ADHEr CBMK2 FRD2 LDH_D ME2 THD2 |
| 160. | ADHEr CBMK2 GLUDy LDH_D ME2 PRO1z SUCD4 |
| 161. | ADHEr CBMK2 GLUDy LDH_D ME2 SUCD4 THD2 |
| 162. | ADHEr CBMK2 GLUDy LDH_D PRO1z SUCD4 |
| 163. | ADHEr CBMK2 GLUDy LDH_D PRO1z SUCD4 THD2 |
| 164. | ADHEr CBMK2 LDH_D ME2 PTAr SUCD4 |
| 165. | ADHEr CBMK2 LDH_D ME2 SUCD4 THD2 |
| 166. | ADHEr DAAD FUM LDH_D PRO1z SUCD4 |
| 167. | ADHEr DAAD G5SD LDH_D ME2 PRO1z SUCD4 |
| 168. | ADHEr DAAD GLCpts LDH_D ME2 PRO1z SUCD4 |
| 169. | ADHEr DAAD GLU5K LDH_D ME2 PRO1z SUCD4 |
| 170. | ADHEr DAAD GLUDy LDH_D ME2 PRO1z SUCD4 |
| 171. | ADHEr DAAD GLUDy LDH_D PRO1z SUCD4 |
| 172. | ADHEr DAAD GLUDy LDH_D PRO1z SUCD4 THD2 |
| 173. | ADHEr DAAD LDH_D ME2 PRO1z SUCD4 |
| 174. | ADHEr DAAD LDH_D ME2 PRO1z SUCD4 THD2 |
| 175. | ADHEr FDH2 GLUDy LDH_D NADH12 NADH6 PRO1z |
| 176. | ADHEr FDH2 LDH_D ME2 NADH12 NADH6 THD2 |
| 177. | ADHEr FRD2 FUM LDH_D |
| 178. | ADHEr FRD2 FUM LDH_D MDH PYK |
| 179. | ADHEr FRD2 G5SD GLCpts LDH_D ME2 |
| 180. | ADHEr FRD2 G5SD LDH_D ME2 |
| 181. | ADHEr FRD2 G5SD LDH_D ME2 PTAr THD2 |
| 182. | ADHEr FRD2 GLCpts GLU5K LDH_D ME2 |
| 183. | ADHEr FRD2 GLCpts GLUDy LDH_D ME2 |
| 184. | ADHEr FRD2 GLCpts GLUDy LDH_D ME2 PTAr |
| 185. | ADHEr FRD2 GLCpts LDH_D ME1x ME2 PYK |
| 186. | ADHEr FRD2 GLCpts LDH_D ME2 |
| 187. | ADHEr FRD2 GLU5K LDH_D ME2 |
| 188. | ADHEr FRD2 GLU5K LDH_D ME2 PTAr THD2 |
| 189. | ADHEr FRD2 GLUDy HEX1 LDH_D ME2 THD2 |
| 190. | ADHEr FRD2 GLUDy HEX1 LDH_D THD2 |
| 191. | ADHEr FRD2 GLUDy LDH_D |
| 192. | ADHEr FRD2 GLUDy LDH_D ME2 |
| 193. | ADHEr FRD2 GLUDy LDH_D ME2 PFLi THD2 |
| 194. | ADHEr FRD2 GLUDy LDH_D ME2 THD2 |
| 195. | ADHEr FRD2 GLUDy LDH_D THD2 |
| 196. | ADHEr FRD2 HEX1 LDH_D ME2 THD2 |
| 197. | ADHEr FRD2 LDH_D ME2 |
| 198. | ADHEr FRD2 LDH_D ME2 PFLi PTAr THD2 |
| 199. | ADHEr FRD2 LDH_D ME2 PFLi THD2 |
| 200. | ADHEr FRD2 LDH_D ME2 PTAr THD2 |
| 201. | ADHEr FRD2 LDH_D ME2 THD2 |
| 202. | ADHEr FRD2 ME1x ME2 PYK |
| 203. | ADHEr GLCpts GLUDy LDH_D ME2 PRO1z SUCD4 |
| 204. | ADHEr GLCpts GLUDy LDH_D ME2 PTAr SUCD4 |
| 205. | ADHEr GLCpts LDH_D ME1x ME2 PYK SUCD4 |
| 206. | ADHEr GLCpts LDH_D ME2 PTAr SUCD4 |
| 207. | ADHEr GLU5K LDH_D |
| 208. | ADHEr GLUDy HEX1 LDH_D ME2 SUCD4 THD2 |
| 209. | ADHEr GLUDy HEX1 LDH_D PRO1z SUCD4 THD2 |
| 210. | ADHEr GLUDy LDH_D ME2 PRO1z SUCD4 |
| 211. | ADHEr GLUDy LDH_D ME2 PRO1z SUCD4 THD2 |
| 212. | ADHEr GLUDy LDH_D ME2 PTAr SUCD4 |
| 213. | ADHEr GLUDy LDH_D ME2 SUCD4 THD2 |
| 214. | ADHEr GLUDy LDH_D PRO1z SUCD4 |
| 215. | ADHEr GLUDy LDH_D PRO1z SUCD4 THD2 |
| 216. | ADHEr GLUDy LDH_D SUCOAS TKT2 |
| 217. | ADHEr HEX1 LDH_D ME2 SUCD4 THD2 |
| 218. | ADHEr LDH_D ME2 PTAr SUCD4 |
| 219. | ADHEr LDH_D ME2 SUCD4 THD2 |

TABLE 1-continued

The list of all strains identified by OptKnock that are most likely to provide increased fumarate yields in E. Coli.

| | |
|---|---|
| 220. | ADHEr THD2 |
| 221. | AKGD ASNS2 ATPS4r CBMK2 PTAr |
| 222. | AKGD ASNS2 ATPS4r GLUDy PTAr |
| 223. | AKGD ASNS2 ATPS4r PTAr |
| 224. | AKGD ASNS2 ATPS4r PTAr RPE |
| 225. | AKGD ASNS2 ATPS4r PTAr TAL |
| 226. | AKGD ASNS2 ATPS4r PTAr TKT1 |
| 227. | AKGD ASNS2 ATPS4r PTAr TKT2 |
| 228. | AKGD ATPS4r CBMK2 GLUDy PTAr |
| 229. | AKGD ATPS4r CBMK2 PTAr |
| 230. | AKGD ATPS4r CBMK2 PTAr RPE |
| 231. | AKGD ATPS4r CBMK2 PTAr TAL |
| 232. | AKGD ATPS4r CBMK2 PTAr TKT1 |
| 233. | AKGD ATPS4r CBMK2 PTAr TKT2 |
| 234. | AKGD ATPS4r GLUDy PTAr |
| 235. | AKGD ATPS4r GLUDy PTAr RPE |
| 236. | AKGD ATPS4r GLUDy PTAr TAL |
| 237. | AKGD ATPS4r GLUDy PTAr TKT1 |
| 238. | AKGD ATPS4r GLUDy PTAr TKT2 |
| 239. | AKGD ATPS4r PPCK PTAr PYK |
| 240. | AKGD ATPS4r PTAr |
| 241. | AKGD ATPS4r PTAr RPE |
| 242. | AKGD ATPS4r PTAr TAL |
| 243. | AKGD ATPS4r PTAr TKT1 |
| 244. | AKGD ATPS4r PTAr TKT2 |
| 245. | ALAR FUM PRO1z SUCD4 |
| 246. | ASNS2 ATPS4r CBMK2 PTAr SUCOAS |
| 247. | ASNS2 ATPS4r FRD2 PFLi |
| 248. | ASNS2 ATPS4r GLUDy PTAr SUCOAS |
| 249. | ASNS2 ATPS4r PDH PFLi |
| 250. | ASNS2 ATPS4r PTAr RPE SUCOAS |
| 251. | ASNS2 ATPS4r PTAr SUCOAS |
| 252. | ASNS2 ATPS4r PTAr SUCOAS TAL |
| 253. | ASNS2 ATPS4r PTAr SUCOAS TKT1 |
| 254. | ASNS2 ATPS4r PTAr SUCOAS TKT2 |
| 255. | ATPS4r CBMK2 FRD2 PFLi |
| 256. | ATPS4r CBMK2 GLUDy PTAr SUCOAS |
| 257. | ATPS4r CBMK2 PDH PFLi |
| 258. | ATPS4r CBMK2 PTAr RPE SUCOAS |
| 259. | ATPS4r CBMK2 PTAr SUCOAS |
| 260. | ATPS4r CBMK2 PTAr SUCOAS TAL |
| 261. | ATPS4r CBMK2 PTAr SUCOAS TKT1 |
| 262. | ATPS4r CBMK2 PTAr SUCOAS TKT2 |
| 263. | ATPS4r FBA FRD2 GLUDy PFLi |
| 264. | ATPS4r FBA FRD2 PFLi |
| 265. | ATPS4r FDH2 PTAr THD5 |
| 266. | ATPS4r FRD2 G5SD PFLi |
| 267. | ATPS4r FRD2 GLU5K PFLi |
| 268. | ATPS4r FRD2 GLUDy PFK PFLi |
| 269. | ATPS4r FRD2 GLUDy PFLi |
| 270. | ATPS4r FRD2 GLUDy PFLi PGI |
| 271. | ATPS4r FRD2 GLUDy PFLi TPI |
| 272. | ATPS4r FRD2 ME1x ME2 PYK |
| 273. | ATPS4r FRD2 ME2 PFLi THD2 |
| 274. | ATPS4r FRD2 PFK PFLi |
| 275. | ATPS4r FRD2 PFLi |
| 276. | ATPS4r FRD2 PFLi PGI |
| 277. | ATPS4r FRD2 PFLi PPCK PYK |
| 278. | ATPS4r FRD2 PFLi TPI |
| 279. | ATPS4r FUM PPCK PTAr |
| 280. | ATPS4r G5SD PDH PFLi |
| 281. | ATPS4r GLCpts ME1x ME2 PYK |
| 282. | ATPS4r GLU5K PDH PFLi |
| 283. | ATPS4r GLUDy PDH PFLi |
| 284. | ATPS4r GLUDy PTAr RPE SUCOAS |
| 285. | ATPS4r GLUDy PTAr SUCOAS |
| 286. | ATPS4r GLUDy PTAr SUCOAS TAL |
| 287. | ATPS4r GLUDy PTAr SUCOAS TKT1 |
| 288. | ATPS4r GLUDy PTAr SUCOAS TKT2 |
| 289. | ATPS4r MDH PPCK PTAr |
| 290. | ATPS4r ME1x ME2 PYK SUCD4 |
| 291. | ATPS4r ME2 NADH12 PFLi THD2 |
| 292. | ATPS4r PDH PFLi |
| 293. | ATPS4r PDH PFLi PPCK PYK |
| 294. | ATPS4r PDH PFLi PTAr |
| 295. | ATPS4r PDH PFLi RPE |
| 296. | ATPS4r PDH PFLi TAL |
| 297. | ATPS4r PDH PFLi TKT1 |
| 298. | ATPS4r PDH PFLi TKT2 |
| 299. | ATPS4r PPCK PTAr PYK SUCOAS |
| 300. | ATPS4r PTAr RPE SUCOAS |
| 301. | ATPS4r PTAr SUCOAS |
| 302. | ATPS4r PTAr SUCOAS TAL |
| 303. | ATPS4r PTAr SUCOAS TKT1 |
| 304. | ATPS4r PTAr SUCOAS TKT2 |
| 305. | CBMK2 PGDH TKT1 |
| 306. | DAAD FUM PRO1z SUCD4 |
| 307. | EDA FRD2 FUM MDH PYK |
| 308. | EDA FRD2 ME1x ME2 PYK |
| 309. | EDA FUM MDH PYK SUCD4 |
| 310. | EDA ME1x ME2 PYK SUCD4 |
| 311. | ENO FUM SUCD4 |
| 312. | FRD2 FUM |
| 313. | FRD2 FUM G6PDHy MDH PYK |
| 314. | FRD2 FUM GLCpts MDH PYK |
| 315. | FRD2 FUM MDH PGDHY PYK |
| 316. | FRD2 FUM MDH PGL PYK |
| 317. | FRD2 FUM MDH PYK |
| 318. | FRD2 G6PDHy ME1x ME2 PYK |
| 319. | FRD2 GLCpts ME1x ME2 PYK |
| 320. | FRD2 GLUDy ME1x ME2 PYK |
| 321. | FRD2 MDH ME1x ME2 |
| 322. | FRD2 ME1x ME2 PFLi PYK |
| 323. | FRD2 ME1x ME2 PGDHY PYK |
| 324. | FRD2 ME1x ME2 PGL PYK |
| 325. | FRD2 ME1x ME2 PTAr PYK |
| 326. | FRD2 ME1x ME2 PYK |
| 327. | FRD2 ME1x ME2 PYK RPE |
| 328. | FRD2 ME1x ME2 PYK TKT2 |
| 329. | FUM G6PDHy MDH PYK SUCD4 |
| 330. | FUM GLCpts MDH PYK SUCD4 |
| 331. | FUM GLUDy PRO1z SUCD4 |
| 332. | FUM MDH PGDHY PYK SUCD4 |
| 333. | FUM MDH PGL PYK SUCD4 |
| 334. | FUM MDH SUCD4 |
| 335. | FUM ME2 SUCD4 |
| 336. | FUM PGM SUCD4 |
| 337. | FUM PPCK SUCD4 |
| 338. | G6PDHy ME1x ME2 PYK SUCD4 |
| 339. | GLCpts ME1x ME2 PYK SUCD4 |
| 340. | GLUDy ME1x ME2 PYK SUCD4 |
| 341. | MDH ME1x ME2 SUCD4 |
| 342. | ME1x ME2 PFLi PYK SUCD4 |
| 343. | ME1x ME2 PGDHY PYK SUCD4 |
| 344. | ME1x ME2 PGL PYK SUCD4 |
| 345. | ME1x ME2 PTAr PYK SUCD4 |
| 346. | ME1x ME2 PYK RPE SUCD4 |
| 347. | ME1x ME2 PYK SUCD4 |
| 348. | ME1x ME2 PYK SUCD4 TKT2 |

TABLE 2

The list of all strains identified by OptKnock that are most likely to provide increased malate yields in E. Coli. Note that some of the malate production strategies overlap with the fumarate production strains.

| | |
|---|---|
| 1. | AKGD ATPS4r PTAr |
| 2. | ACKr AKGD ATPS4r |
| 3. | ACKr ATPS4r SUCOAS |
| 4. | ATPS4r PTAr SUCOAS |
| 5. | ATPS4r PDH PFLi |
| 6. | ATPS4r FRD2 PFLi |
| 7. | LDH_D PFK SUCOAS |
| 8. | ADHEr FRD2 GLUDy LDH_D |
| 9. | ADHEr FRD2 LDH_D ME2 |
| 10. | ACKr AKGD ATPS4r GLUDy |
| 11. | AKGD ATPS4r GLUDy PTAr |
| 12. | ATPS4r GLUDy PTAr SUCOAS |
| 13. | ACKr ATPS4r GLUDy SUCOAS |
| 14. | AKGD ATPS4r PTAr TKT2 |

TABLE 2-continued

The list of all strains identified by OptKnock that are most likely to provide increased malate yields in *E. Coli*. Note that some of the malate production strategies overlap with the fumarate production strains.

| | |
|---|---|
| 15. | ACKr AKGD ATPS4r TKT2 |
| 16. | ATPS4r PTAr SUCOAS TKT2 |
| 17. | ACKr ATPS4r SUCOAS TKT2 |
| 18. | ATPS4r FUM GLUDy PFLi |
| 19. | ACKr AKGD ATPS4r RPE |
| 20. | AKGD ATPS4r PTAr RPE |
| 21. | ACKr ATPS4r RPE SUCOAS |
| 22. | ATPS4r PTAr RPE SUCOAS |
| 23. | ACKr AKGD ATPS4r TKT1 |
| 24. | AKGD ATPS4r PTAr TAL |
| 25. | AKGD ATPS4r PTAr TKT1 |
| 26. | ACKr AKGD ATPS4r TAL |
| 27. | AKGD ATPS4r CBMK2 PTAr |
| 28. | ACKr AKGD ATPS4r CBMK2 |
| 29. | ACKr ATPS4r SUCOAS TAL |
| 30. | ATPS4r PTAr SUCOAS TAL |
| 31. | ACKr ATPS4r SUCOAS TKT1 |
| 32. | ATPS4r PTAr SUCOAS TKT1 |
| 33. | ACKr AKGD ASNS2 ATPS4r |
| 34. | AKGD ASNS2 ATPS4r PTAr |
| 35. | ATPS4r CBMK2 PTAr SUCOAS |
| 36. | ACKr ATPS4r CBMK2 SUCOAS |
| 37. | ACKr ASNS2 ATPS4r SUCOAS |
| 38. | ASNS2 ATPS4r PTAr SUCOAS |
| 39. | ATPS4r FRD2 PFLi PGI |
| 40. | ATPS4r FRD2 PFK PFLi |
| 41. | ATPS4r FRD2 PFLi TPI |
| 42. | ATPS4r FBA FRD2 PFLi |
| 43. | FRD2 ME1x ME2 PYK |
| 44. | ME1x ME2 PYK SUCD4 |
| 45. | ATPS4r FRD2 GLUDy PFLi |
| 46. | ATPS4r GLUDy PDH PFLi |
| 47. | ACKr ATPS4r PDH PFLi |
| 48. | ATPS4r PDH PFLi PTAr |
| 49. | ATPS4r PDH PFLi TKT2 |
| 50. | ATPS4r PDH PFLi RPE |
| 51. | ATPS4r PDH PFLi TAL |
| 52. | ATPS4r PDH PFLi TKT1 |
| 53. | ATPS4r CBMK2 PDH PFLi |
| 54. | ATPS4r GLU5K PDH PFLi |
| 55. | ATPS4r G5SD PDH PFLi |
| 56. | ASNS2 ATPS4r PDH PFLi |
| 57. | ASPT ATPS4r FUM PFLi |
| 58. | ATPS4r CBMK2 FRD2 PFLi |
| 59. | ATPS4r FRD2 GLU5K PFLi |
| 60. | ATPS4r FRD2 G5SD PFLi |
| 61. | ASNS2 ATPS4r FRD2 PFLi |
| 62. | ADHEr ATPS4r FUM GLUDy |
| 63. | MDH ME1x ME2 SUCD4 |
| 64. | FRD2 MDH ME1x ME2 |
| 65. | ATPS4r MDH PPCK PTAr |
| 66. | ACKr ATPS4r MDH PPCK |
| 67. | ADHEr FRD2 LDH_D ME2 THD2 |
| 68. | ADHEr FRD2 GLUDy LDH_D THD2 |
| 69. | ADHEr FRD2 GLUDy LDH_D ME2 |
| 70. | ADHEr CBMK2 FRD2 GLUDy LDH_D |
| 71. | ADHEr LDH_D ME2 SUCD4 THD2 |
| 72. | ADHEr FUM GLUDy LDH_D SUCD4 |
| 73. | ADHEr ASPT FUM GLUDy LDH_D |
| 74. | ADHEr FRD2 GLCpts LDH_D ME2 |
| 75. | ADHEr GLUDy LDH_D PRO1z SUCD4 |
| 76. | ADHEr CBMK2 FRD2 LDH_D ME2 |
| 77. | ADHEr FRD2 GLU5K LDH_D ME2 |
| 78. | ADHEr FRD2 G5SD LDH_D ME2 |
| 79. | ADHEr ASNS2 FRD2 LDH_D ME2 |
| 80. | ADHEr FUM GLUDy LDH_D NADH6 |
| 81. | ADHEr ASPT FUM LDH_D ME2 |
| 82. | FRD2 GLCpts ME1x ME2 PYK |
| 83. | GLCpts ME1x ME2 PYK SUCD4 |
| 84. | ACKr ADHEr LDH_D ME2 SUCD4 |
| 85. | ADHEr LDH_D ME2 PTAr SUCD4 |
| 86. | ADHEr FRD2 ME1x ME2 PYK |
| 87. | FRD2 ME1x ME2 PGL PYK |
| 88. | FRD2 G6PDHy ME1x ME2 PYK |
| 89. | FRD2 ME1x ME2 PGDHY PYK |
| 90. | EDA ME1x ME2 PYK SUCD4 |
| 91. | EDA FRD2 ME1x ME2 PYK |
| 92. | ME1x ME2 PGDHY PYK SUCD4 |
| 93. | ME1x ME2 PGL PYK SUCD4 |
| 94. | G6PDHy ME1x ME2 PYK SUCD4 |
| 95. | ACKr AKGD ATPS4r PPCK PYK |
| 96. | AKGD ATPS4r PPCK PTAr PYK |
| 97. | FRD2 ME1x ME2 PFLi PYK |
| 98. | ACKr ATPS4r PPCK PYK SUCOAS |
| 99. | ATPS4r PPCK PTAr PYK SUCOAS |
| 100. | FRD2 ME1x ME2 PTAr PYK |
| 101. | ACKr ME1x ME2 PYK SUCD4 |
| 102. | ME1x ME2 PTAr PYK SUCD4 |
| 103. | ACKr FRD2 ME1x ME2 PYK |
| 104. | ACKr AKGD ATPS4r GLUDy TKT2 |
| 105. | AKGD ATPS4r GLUDy PTAr TKT2 |
| 106. | ATPS4r GLUDy PTAr SUCOAS TKT2 |
| 107. | ACKr ATPS4r GLUDy SUCOAS TKT2 |
| 108. | AKGD ATPS4r GLUDy PTAr RPE |
| 109. | ACKr AKGD ATPS4r GLUDy RPE |
| 110. | ATPS4r GLUDy PTAr RPE SUCOAS |
| 111. | ACKr ATPS4r GLUDy RPE SUCOAS |
| 112. | AKGD ATPS4r GLUDy PTAr TAL |
| 113. | ACKr AKGD ATPS4r GLUDy TAL |
| 114. | AKGD ATPS4r GLUDy PTAr TKT1 |
| 115. | ACKr AKGD ATPS4r GLUDy TKT1 |
| 116. | ATPS4r FRD2 PFLi PPCK PYK |
| 117. | ATPS4r GLUDy PTAr SUCOAS TKT1 |
| 118. | ACKr ATPS4r GLUDy SUCOAS TKT1 |
| 119. | ACKr ATPS4r GLUDy SUCOAS TAL |
| 120. | ATPS4r GLUDy PTAr SUCOAS TAL |
| 121. | ACKr AKGD ATPS4r CBMK2 GLUDy |
| 122. | AKGD ATPS4r CBMK2 GLUDy PTAr |
| 123. | ACKr AKGD ASNS2 ATPS4r GLUDy |
| 124. | AKGD ASNS2 ATPS4r GLUDy PTAr |
| 125. | ATPS4r CBMK2 GLUDy PTAr SUCOAS |
| 126. | ACKr ATPS4r CBMK2 GLUDy SUCOAS |
| 127. | ASNS2 ATPS4r GLUDy PTAr SUCOAS |
| 128. | ACKr ASNS2 ATPS4r GLUDy SUCOAS |
| 129. | ATPS4r FUM GLUDy PFLi TKT2 |
| 130. | ATPS4r FUM ME2 PFLi THD2 |
| 131. | ACKr AKGD ATPS4r CBMK2 TKT2 |
| 132. | AKGD ATPS4r CBMK2 PTAr TKT2 |
| 133. | ATPS4r ME2 NADH12 PFLi THD2 |
| 134. | ATPS4r FUM GLUDy PFLi RPE |
| 135. | AKGD ASNS2 ATPS4r PTAr TKT2 |
| 136. | ACKr AKGD ASNS2 ATPS4r TKT2 |
| 137. | ACKr ATPS4r CBMK2 SUCOAS TKT2 |
| 138. | ATPS4r CBMK2 PTAr SUCOAS TKT2 |
| 139. | ATPS4r FUM GLUDy PFLi TKT1 |
| 140. | ATPS4r FUM GLUDy PFLi TAL |
| 141. | ACKr ASNS2 ATPS4r SUCOAS TKT2 |
| 142. | ASNS2 ATPS4r PTAr SUCOAS TKT2 |
| 143. | ATPS4r CBMK2 FUM GLUDy PFLi |
| 144. | ACKr ATPS4r FUM GLUDy PFLi |
| 145. | ATPS4r FUM GLUDy PFLi PTAr |
| 146. | ACKr AKGD ATPS4r CBMK2 RPE |
| 147. | AKGD ATPS4r CBMK2 PTAr RPE |
| 148. | ATPS4r FUM GLU5K GLUDy PFLi |
| 149. | ATPS4r FUM G5SD GLUDy PFLi |
| 150. | ASNS2 ATPS4r FUM GLUDy PFLi |
| 151. | AKGD ASNS2 ATPS4r PTAr RPE |
| 152. | ACKr AKGD ASNS2 ATPS4r RPE |
| 153. | ACKr ATPS4r CBMK2 RPE SUCOAS |
| 154. | ATPS4r CBMK2 PTAr RPE SUCOAS |
| 155. | ASNS2 ATPS4r PTAr RPE SUCOAS |
| 156. | ACKr ASNS2 ATPS4r RPE SUCOAS |
| 157. | AKGD ATPS4r CBMK2 PTAr TAL |
| 158. | AKGD ATPS4r CBMK2 PTAr TKT1 |
| 159. | ACKr AKGD ATPS4r CBMK2 TAL |
| 160. | ACKr AKGD ATPS4r CBMK2 TKT1 |
| 161. | ACKr AKGD ASNS2 ATPS4r TAL |
| 162. | AKGD ASNS2 ATPS4r PTAr TKT1 |
| 163. | AKGD ASNS2 ATPS4r PTAr TAL |
| 164. | ACKr AKGD ASNS2 ATPS4r TKT1 |

TABLE 2-continued

The list of all strains identified by OptKnock that are most likely to provide increased malate yields in *E. Coli*. Note that some of the malate production strategies overlap with the fumarate production strains.

| | |
|---|---|
| 165. | ACKr ATPS4r CBMK2 SUCOAS TKT1 |
| 166. | ACKr ATPS4r CBMK2 SUCOAS TAL |
| 167. | ATPS4r CBMK2 PTAr SUCOAS TKT1 |
| 168. | ATPS4r CBMK2 PTAr SUCOAS TAL |
| 169. | AKGD ASNS2 ATPS4r CBMK2 PTAr |
| 170. | ACKr AKGD ASNS2 ATPS4r CBMK2 |
| 171. | ACKr ASNS2 ATPS4r CBMK2 SUCOAS TAL |
| 172. | ASNS2 ATPS4r PTAr SUCOAS TKT1 |
| 173. | ASNS2 ATPS4r PTAr SUCOAS TAL |
| 174. | ACKr ASNS2 ATPS4r SUCOAS TKT1 |
| 175. | ACKr ASNS2 ATPS4r CBMK2 SUCOAS |
| 176. | ASNS2 ATPS4r CBMK2 PTAr SUCOAS |
| 177. | ATPS4r GLCpts ME1x ME2 PYK |
| 178. | ATPS4r FRD2 ME2 PFLi THD2 |
| 179. | ME1x ME2 PFLi PYK SUCD4 |
| 180. | FRD2 GLUDy ME1x ME2 PYK |
| 181. | GLUDy ME1x ME2 PYK SUCD4 |
| 182. | FRD2 ME1x ME2 PYK TKT2 |
| 183. | ME1x ME2 PYK SUCD4 TKT2 |
| 184. | ATPS4r FRD2 GLUDy PFLi PGI |
| 185. | ATPS4r FRD2 GLUDy PFLi TPI |
| 186. | ATPS4r FBA FRD2 GLUDy PFLi |
| 187. | ATPS4r FRD2 GLUDy PFK PFLi |
| 188. | ATPS4r PDH PFLi PPCK PYK |
| 189. | ME1x ME2 PYK RPE SUCD4 |
| 190. | FRD2 ME1x ME2 PYK RPE |
| 191. | ATPS4r FRD2 ME1x ME2 PYK |
| 192. | ATPS4r ME1x ME2 PYK SUCD4 |
| 193. | FUM GLUDy ME1x ME2 PYK |
| 194. | ASPT ATPS4r FUM PFLi PGI |
| 195. | FRD2 ME1x ME2 PYK TKT1 |
| 196. | ME1x ME2 PYK SUCD4 TAL |
| 197. | ME1x ME2 PYK SUCD4 TKT1 |
| 198. | FRD2 ME1x ME2 PYK TAL |
| 199. | ASPT ATPS4r FUM PFLi TPI |
| 200. | ASPT ATPS4r FUM PFK PFLi |

TABLE 3

A list of all the reaction stoichiometries and the associated genes known to be associated with the reactions identified for deletion in the strains listed in Tables 1 and 2.

| Reaction Abbreviation | Reaction Name | Reaction Stoichiometry | Associated genes |
|---|---|---|---|
| ACKr | Acetate kinase | [c]: ac + atp <==> actp + adp | (b3115 or b2296 or b1849) |
| ADHEr | Alcohol dehydrogenase | [c]: accoa + (2) h + (2) nadh <==> coa + etoh + (2) nad | (b0356 or b1478 or b1241) |
| AKGD | Alpha-ketoglutarate dehydrogenase | [c]: akg + coa + nad --> co2 + nadh + succoa | (b0116 and b0726 and b0727) |
| ALAR | Alanine racemase | [c]: ala-L <==> ala-D | b4053 |
| ASNS2 | Asparagine synthetase | [c]: asp-L + atp + nh4 --> amp + asn-L + h + ppi | b3744 |
| ASPT | L-aspartase | [c]: asp-L --> fum + nh4 | b4139 |
| ATPS4r | ATP synthase | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | Carbamate kinase | [c]: atp + co2 + nh4 --> adp + cbp + (2) h | (b0521 or b0323 or b2874) |
| DAAD | D-amino acid dehydrogenase | [c]: ala-D + fad + h2o --> fadh2 + nh4 + pyr | b1189 |
| EDA | 2-dehydro-3-deoxy-phosphogluconate aldolase | [c]: 2ddg6p --> g3p + pyr | b1850 |
| ENO | Enolase | [c]: 2pg <==> h2o + pep | b2779 |
| FBA | Fructose-bis-phosphate aldolase | [c]: fdp <==> dhap + g3p | (b2097 or b2925 or b1773) |
| FRD | Fumarate reductase | [c]: fum + mql8 --> mqn8 + succ | (b4151 and b4152 and b4153 and b4154) |
| FUM | Fumarase | [c]: fum + h2o <==> mal-L | (b1612 or b4122 or b1611) |
| G5SD | Glutamate-5-semialdehyde dehydrogenase | [c]: glu5p + h + nadph --> glu5sa + nadp + pi | b0243 |
| G6PDHy | Glucose-6-phosphate dehydrogenase | [c]: g6p + nadp <==> 6pgl + h + nadph | b1852 |
| GLCpts | D-glucose transport via PTS mechanism | glc-D[e] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | Gluatmate-5-kinase | [c]: atp + glu-L --> adp + glu5p | b0242 |
| GLUDy | Glutamate dehydrogenase | [c]: glu-L + h2o + nadp <==> akg + h + nadph + nh4 | b1761 |
| HEX1 | Hexokinase | [c]: atp + glc-D --> adp + g6p + h | b2388 |
| LDH_D | Lactate dehydrogenase | [c]: lac-D + nad <==> h + nadh + pyr | b1380 or b2133 |

TABLE 3-continued

A list of all the reaction stoichiometries and the associated genes known to be associated with the reactions identified for deletion in the strains listed in Tables 1 and 2.

| Reaction Abbreviation | Reaction Name | Reaction Stoichiometry | Associated genes |
|---|---|---|---|
| MDH | Malate dehydrogenase | [c]: mal-L + nad <==> h + nadh + oaa | b3236 |
| ME1x | Malic enzyme (NAD) | [c]: mal-L + nad --> co2 + nadh + pyr | b1479 |
| ME2 | Malic enzyme (NADP) | [c]: mal-L + nadp --> co2 + nadph + pyr | b2463 |
| NADH12 | NADH dehydrogenase (ubiquinone-8) | [c]: h + nadh + ubq8 --> nad + ubq8h2 | b1109 |
| NADH6 | NADH dehydrogenase (ubiquinone-8 and 3.5 protons) | (4.5) h[c] + nadh[c] + ubq8[c] --> (3.5) h[e] + nad[c] + ubq8h2[c] | (b2276 and b2277 and b2278 and b2279 and b2280 and b2281 and b2282 and b2283 and b2284 and b2285 and b2286 and b2287 and b2288) |
| PDH | Pyruvate dehydrogenase | [c]: coa + nad + pyr --> accoa + co2 + nadh | ((b0114 and b0115 and b0116) or (b0116 and b0726 and b0727) or (b0116 and b2903 and b2904 and b2905)) |
| PFK | Phosphofructokinase | [c]: atp + f6p --> adp + fdp + h | (b3916 or b1723) |
| PFLi | Pyruvate formate lyase | [c]: coa + pyr --> accoa + for | (((b0902 and b0903) and b2579) or (b0902 and b0903) or (b0902 and b3114) or (b3951 and b3952)) |
| PGDH | Phosphogluconate dehyrogenase | [c]: 6pgc + nadp --> co2 + nadph + ru5p-D | b2029 |
| PGDHY | Phosphogluconate dehydratase | [c]: 6pgc --> 2ddg6p + h2o | b1851 |
| PGI | Glucose-6-phosphate isomerase | [c]: g6p <==> f6p | b4025 |
| PGL | 6-Phosphogluconolactonase | [c]: 6pgl + h2o --> 6pgc + h | b0767 |
| PGM | Phosphoglycerate mutase | [c]: 3pg <==> 2pg | b3612 |
| PPC | Phosphoenolpyruvate carboxylase | [c]: co2 + h2o + pep --> h + oaa + pi | b3956 |
| PPCK | Phosphoenolpyruvate carboxykinase | [c]: atp + oaa --> adp + co2 + pep | b3403 |
| PRO1z | Proline oxidase | [c]: fad + pro-L --> 1pyr5c + fadh2 + h | b1014 |
| PTAr | Phosphotransacetylase | [c]: accoa + pi <==> actp + coa | b2297 |
| PYK | Pyruvate kinase | [c]: adp + h + pep --> atp + pyr | (b1854 or b1676) |
| RPE | Ribulose-5-phosphate-5-epimerase | [c]: ru5p-D <==> xu5p-D | (b4301 or b3386) |
| SUCD4 | Succinate dehydrogenase | [c]: fadh2 + ubq8 <==> fad + ubq8h2 | (b0721 and b0722 and b0723 and b0724) |
| SUCOAS | Succinyl-CoA synthetase | [c]: atp + coa + succ <==> adp + pi + succoa | (b0728 and b0729) |
| TAL | Transaldoalse | [c]: g3p + s7p <==> e4p + f6p | (b2464 or b0008) |
| THD2 | NADP transhydrogenase | (2) h[e] + nadh[c] + nadp[c] --> (2) h[c] + nad[c] + nadph[c] | (b1602 and b1603) |
| THD5 | NAD transhydrogenase | [c]: nad + nadph --> nadh + nadp | (b3962 or (b1602 and b1603)) |
| TKT1 | Transketolase | [c]: r5p + xu5p-D <==> g3p + s7p | (b2935 or b2465) |
| TKT2 | Transketolase | [c]: e4p + xu5p-D <==> f6p + g3p | (b2935 or b2465) |
| TPI | Triosephosphate isomerase | [c]: dhap <==> g3p | b3919 |
| VALTA | Valine transaminase | [c]: akg + val-L <==> 3mob + glu-L | b3770 |

TABLE 4

List of the metabolite abbreviations, the corresponding names and locations of all the metabolites that participate in the reactions listed in Table 3.

| Metabolite Abbreviation | Compartment | Metabolite Name |
|---|---|---|
| 13dpg | Cytosol | 3-Phospho-D-glyceroyl phosphate |
| 1pyr5c | Cytosol | 1-Pyrroline-5-carboxylate |
| 2ddg6p | Cytosol | 2-Dehydro-3-deoxy-D-gluconate 6-phosphate |
| 2pg | Cytosol | D-Glycerate 2-phosphate |
| 3mob | Cytosol | 3-Methyl-2-oxobutanoate |
| 3pg | Cytosol | 3-Phospho-D-glycerate |
| 6pgc | Cytosol | 6-Phospho-D-gluconate |
| 6pgl | Cytosol | 6-phospho-D-glucono-1,5-lactone |
| ac | Cytosol | Acetate |

TABLE 4-continued

List of the metabolite abbreviations, the corresponding names and locations of all the metabolites that participate in the reactions listed in Table 3.

| Metabolite Abbreviation | Compartment | Metabolite Name |
|---|---|---|
| accoa | Cytosol | Acetyl-CoA |
| actp | Cytosol | Acetyl phosphate |
| adp | Cytosol | Adenosine diphosphate |
| akg | Cytosol | 2-Oxoglutarate |
| ala-D | Cytosol | D-alanine |
| ala-L | Cytosol | L-alanine |
| amp | Cytosol | Adenosine monophosphate |
| asn-L | Cytosol | L-asparagine |
| asp-L | Cytosol | L-aspartate |
| atp | Cytosol | Adenosine triphosphate |
| cbp | Cytosol | Carbamoyl phosphate |
| co2 | Cytosol | Carbon dioxide |
| coa | Cytosol | Coenzyme A |
| dha | Cytosol | Dihydroxyacetone |
| dhap | Cytosol | Dihydroxyacetone phosphate |
| e4p | Cytosol | D-Erythrose 4-phosphate |
| etoh | Cytosol | Ethanol |
| f6p | Cytosol | D-Fructose 6-phosphate |
| fad | Cytosol | Flavin adenine dinucleotide |
| fadh2 | Cytosol | Flavin adenine dinucleotide-reduced |
| fdp | Cytosol | D-Fructose 1,6-bisphosphate |
| for | Cytosol | Formate |
| fum | Cytosol | Fumarate |
| g3p | Cytosol | Glyceraldehyde 3-phosphate |
| g6p | Cytosol | D-Glucose 6-phosphate |
| glc-D[e] | Extra-organism | D-Glucose |
| glu5p | Cytosol | L-glutamate 5-phosphate |
| glu5sa | Cytosol | L-glutamate 5-semialdehyde |
| glu-L | Cytosol | L-Glutamate |
| h | Cytosol | H$^+$ |
| h[e] | Extra-organism | H$^+$ |
| h2o | Cytosol | Water |
| lac-D | Cytosol | D-Lactate |
| mal-L | Cytosol | L-Malate |
| mql-8 | Cytosol | Menaquinol-8 |
| mqn-8 | Cytosol | Menaquinone-8 |
| nad | Cytosol | Nicotinamide adenine dinucleotide |
| nadh | Cytosol | Nicotinamide adenine dinucleotide - reduced |
| nadp | Cytosol | Nicotinamide adenine dinucleotide phosphate |
| nadph | Cytosol | Nicotinamide adenine dinucleotide phosphate - reduced |
| nh4 | Cytosol | Ammonium |
| o2 | Cytosol | Oxygen |
| oaa | Cytosol | Oxaloacetate |
| pep | Cytosol | Phosphoenolpyruvate |
| pi | Cytosol | Phosphate |
| ppi | Cytosol | Diphosphate |
| pyr | Cytosol | Pyruvate |
| r5p | Cytosol | alpha-D-Ribose 5-phosphate |
| ru5p-D | Cytosol | D-Ribulose 5-phosphate |
| s7p | Cytosol | Sedoheptulose 7-phosphate |
| succ | Cytosol | Succinate |
| succoa | Cytosol | Succinyl-CoA |
| ubq8 | Cytosol | Ubiquinone-8 |
| ubq8h2 | Cytosol | Ubiquinol-8 |
| val-L | Cytosol | L-valine |
| xu5p-D | Cytosol | D-Xylulose 5-phosphate |

TABLE 5

The list of all strains identified by OptKnock that are most likely to provide increased fumarate yields in S. Cerevisiae under microaerobic culture conditions. These same designs can be used for malate production if the cytosolic fumarase (FUM) is deleted additionally.

| | |
|---|---|
| 1 | FRDm FUM |
| 2 | ME1m PYK FRDm FUMm |
| 3 | ME1m G3PDm PYK SUCD3-u6m |
| 4 | G3PDm GLY3PP SUCD3-u6m ALCD2x |
| 5 | GLY3PP FRDm FUMm ALCD2x |
| 6 | G3PD FRDm FUMm ALCD2x |
| 7 | G3PD G3PD1irm SUCD3-u6m ALCD2x |
| 8 | G3PD G3PDm SUCD3-u6m ALCD2x |
| 9 | G3PDm PYK MDHm SUCD3-u6m |
| 10 | PYK FRDm FUMm MDHm |
| 11 | G3PD G3PDm SUCD3-u6m PYRDC |
| 12 | G3PDm GLY3PP SUCD3-u6m PYRDC |
| 13 | GLY3PP FRDm FUMm PYRDC |
| 14 | G3PD FRDm FUMm PYRDC |
| 15 | G3PD G3PD1irm SUCD3-u6m PYRDC |
| 16 | G3PDm SUCD3-u6m PYRDC ATPtm-3H |
| 17 | FRDm FUMm PYRDC ATPtm-3H |
| 18 | ATPSm FRDm FUMm PYRDC |
| 19 | G3PDm ATPSm SUCD3-u6m PYRDC |
| 20 | FRDm FUMm ALCD2x ATPtm-3H |
| 21 | G3PDm SUCD3-u6m ALCD2x ATPtm-3H |
| 22 | ATPSm FRDm FUMm ALCD2x |
| 23 | G3PDm ATPSm SUCD3-u6m ALCD2x |
| 24 | ME1m FRDm FUMm PYRDC |
| 25 | ME1m G3PDm SUCD3-u6m PYRDC |
| 26 | G3PDm MDHm SUCD3-u6m PYRDC |
| 27 | FRDm FUMm MDHm PYRDC |
| 28 | ME1m G3PDm SUCD3-u6m ALCD2x |
| 29 | ME1m FRDm FUMm ALCD2x |
| 30 | G3PDm MDHm SUCD3-u6m ALCD2x |
| 31 | FRDm FUMm MDHm ALCD2x |
| 32 | ASPTA1 G3PDm GLY3PP SUCD3-u6m |
| 33 | ASPTA1 G3PD FRDm FUMm |
| 34 | ASPTA1 GLY3PP FRDm FUMm |
| 35 | ASPTA1 G3PD G3PDm SUCD3-u6m |
| 36 | ASPTA1 G3PD G3PD1irm SUCD3-u6m |
| 37 | G3PDm GLY3PP HSK SUCD3-u6m |
| 38 | G3PDm GLY3PP SUCD3-u6m THRS |
| 39 | G3PD FRDm FUMm THRS |
| 40 | GLY3PP HSK FRDm FUMm |
| 41 | G3PD G3PDm HSK SUCD3-u6m |
| 42 | G3PD G3PD1irm HSK SUCD3-u6m |
| 43 | G3PD G3PD1irm SUCD3-u6m THRS |
| 44 | GLY3PP FRDm FUMm THRS |
| 45 | G3PD HSK FRDm FUMm |
| 46 | G3PD G3PDm SUCD3-u6m THRS |
| 47 | G3PD FRDm FUMm PGL |
| 48 | G3PD FRDm FUMm PGDH |
| 49 | G3PD G3PD1irm SUCD3-u6m PGDH |
| 50 | G3PD G3PDm SUCD3-u6m PGDH |
| 51 | G3PDm GLY3PP SUCD3-u6m G6PDH |
| 52 | G3PD G3PDm SUCD3-u6m G6PDH |
| 53 | G3PDm GLY3PP SUCD3-u6m PGL |
| 54 | G3PDm GLY3PP SUCD3-u6m PGDH |
| 55 | GLY3PP FRDm FUMm G6PDH |
| 56 | G3PD G3PDm SUCD3-u6m PGL |
| 57 | G3PD G3PD1irm SUCD3-u6m PGL |
| 58 | GLY3PP FRDm FUMm PGL |
| 59 | GLY3PP FRDm FUMm PGDH |
| 60 | G3PD G3PD1irm SUCD3-u6m G6PDH |
| 61 | G3PD FRDm FUMm G6PDH |
| 62 | G3PD G3PDm SUCD3-u6m TKT1 |
| 63 | G3PDm GLY3PP SUCD3-u6m TKT1 |
| 64 | G3PD FRDm FUMm TKT1 |
| 65 | G3PD G3PD1irm SUCD3-u6m TKT1 |
| 66 | GLY3PP FRDm FUMm TKT1 |
| 67 | G3PDm GLY3PP SUCD3-u6m RPE |
| 68 | G3PD G3PDm SUCD3-u6m RPE |
| 69 | GLY3PP FRDm FUMm RPE |
| 70 | G3PD G3PD1irm SUCD3-u6m RPE |
| 71 | G3PD FRDm FUMm RPE |
| 72 | G3PDm SERD_L PGI SUCD3-u6m |
| 73 | SERD_L PGI FRDm FUMm |
| 74 | GLY3PP FRDm FUMm THRA |
| 75 | G3PD FRDm FUMm THRA |
| 76 | G3PDm GLY3PP SUCD3-u6m THRA |
| 77 | G3PD G3PDm SUCD3-u6m THRA |
| 78 | G3PD G3PD1irm SUCD3-u6m THRA |

TABLE 5-continued

The list of all strains identified by OptKnock that are most likely to provide increased fumarate yields in *S. Cerevisiae* under microaerobic culture conditions. These same designs can be used for malate production if the cytosolic fumarase (FUM) is deleted additionally.

| | |
|---|---|
| 79 | ALATA_L ASPTA1 SUCOASAm PSP_L |
| 80 | ALATA_L ASPTA1 PSERT PDHcm |
| 81 | ALATA_L ASPTA1 AKGDbm PGCD |
| 82 | ALATA_L ASPTA1 SUCOASAm PSERT |
| 83 | ALATA_L ASPTA1 SUCOASAm PGCD |
| 84 | ALATA_L ASPTA1 AKGDam PSERT |
| 85 | ALATA_L ASPTA1 AKGDbm PSERT |
| 86 | ALATA_L ASPTA1 PSP_L PDHcm |
| 87 | ALATA_L ASPTA1 AKGDbm PSP_L |
| 88 | ALATA_L ASPTA1 PGCD PDHcm |
| 89 | ALATA_L ASPTA1 AKGDam PSP_L |
| 90 | ALATA_L ASPTA1 AKGDam PGCD |
| 91 | ASPTA1 ICL SUCOASAm PSP_L |
| 92 | ASPTA1 SUCOASAm AGT PSP_L |
| 93 | ASPTA1 SUCOASAm AGT PSERT |
| 94 | ASPTA1 SUCOASAm AGT PGCD |
| 95 | ASPTA1 ICL SUCOASAm PSERT |
| 96 | ASPTA1 ICL SUCOASAm PGCD |
| 97 | ASPTA1 AGT PSP_L PDHcm |
| 98 | ASPTA1 ICL AKGDbm PSP_L |
| 99 | ASPTA1 AKGDam AGT PSP_L |
| 100 | ASPTA1 AGT PGCD PDHcm |
| 101 | ASPTA1 AKGDbm AGT PGCD |
| 102 | ASPTA1 AKGDbm AGT PSERT |
| 103 | ASPTA1 ICL PGCD PDHcm |
| 104 | ASPTA1 ICL AKGDbm PGCD |
| 105 | ASPTA1 AGT PSERT PDHcm |
| 106 | ASPTA1 ICL PSP_L PDHcm |
| 107 | ASPTA1 ICL AKGDam PSERT |
| 108 | ASPTA1 ICL AKGDam PSP_L |
| 109 | ASPTA1 ICL PSERT PDHcm |
| 110 | ASPTA1 AKGDbm AGT PSP_L |
| 111 | ASPTA1 ICL AKGDam PGCD |
| 112 | ASPTA1 AKGDam AGT PSERT |
| 113 | ASPTA1 AKGDam AGT PGCD |
| 114 | ASPTA1 ICL AKGDbm PSERT |
| 115 | GLY3PP HSDxi FRDm FUMm |
| 116 | G3PD HSDxi FRDm FUMm |
| 117 | G3PD G3PDm HSDxi SUCD3-u6m |
| 118 | G3PD G3PD1irm HSDxi SUCD3-u6m |
| 119 | G3PDm GLY3PP HSDxi SUCD3-u6m |
| 120 | G3PDm FUM SUCD1rm SUCD3-u6m |
| 121 | G3PDm FUM FUMm SUCD3-u6m |
| 122 | G3PDm MDH NADH2-u6cm NADH2-u6m |
| 123 | ASPTA1 ME1m PSERT PDHm PYK |
| 124 | ASPTA1 ME1m PSP_L PDHm PYK |
| 125 | ASPTA1 ME1m PGCD PDHm PYK |
| 126 | ASPTA1 ME1m ME2m PSP_L PYK |
| 127 | ASPTA1 ME1m ME2m PGCD PYK |
| 128 | ASPTA1 ME1m ME2m PSERT PYK |
| 129 | ASPTA1 ORNTA ME1m PSP_L PYK |
| 130 | ASPTA1 ORNTA ME1m PGCD PYK |
| 131 | ASPTA1 ORNTA ME1m PSERT PYK |
| 132 | ASPTA1 ME1m PRO1xm PSP_L PYK |
| 133 | ASPTA1 ME1m P5CDm PSERT PYK |
| 134 | ASPTA1 ME1m P5CDm PSP_L PYK |
| 135 | ASPTA1 ME1m PRO1xm PGCD PYK |
| 136 | ASPTA1 ME1m PRO1xm PGCD PYK |
| 137 | ASPTA1 ME1m PRO1xm PSERT PYK |
| 138 | ASPTA1m ME1m PSP_L PDHm PYK |
| 139 | ASPTA1m ME1m PSERT PDHm PYK |
| 140 | ASPTA1m ME1m PGCD PDHm PYK |
| 141 | ASPTA1m ME1m PRO1xm PSP_L PYK |
| 142 | ASPTA1m ME1m P5CDm PGCD PYK |
| 143 | ASPTA1m ME1m PRO1xm PGCD PYK |
| 144 | ASPTA1m ME1m PRO1xm PGCD PYK |
| 145 | ASPTA1m ME1m P5CDm PSERT PYK |
| 146 | ASPTA1m ME1m P5CDm PSP_L PYK |
| 147 | ASPTA1m ME1m PSERT PDHcm PYK |
| 148 | ASPTA1m ME1m SUCOASAm PSERT PYK |
| 149 | ASPTA1m ME1m AKGDam PSP_L PYK |
| 150 | ASPTA1m ME1m AKGDbm PSERT PYK |
| 151 | ASPTA1m ME1m SUCOASAm PGCD PYK |
| 152 | ASPTA1m ME1m AKGDam PGCD PYK |
| 153 | ASPTA1m ME1m SUCOASAm PSP_L PYK |
| 154 | ASPTA1m ME1m AKGDam PSERT PYK |
| 155 | ASPTA1m ME1m PSP_L PDHcm PYK |
| 156 | ASPTA1m ME1m PGCD PDHcm PYK |
| 157 | ASPTA1m ME1m AKGDbm PGCD PYK |
| 158 | ASPTA1m ME1m AKGDbm PSP_L PYK |
| 159 | ASPTA1m ORNTA ME1m PSP_L PYK |
| 160 | ASPTA1m ORNTA ME1m PGCD PYK |
| 161 | ASPTA1m ORNTA ME1m PSERT PYK |
| 162 | ME1m ME2m ACONTm PSP_L PYK |
| 163 | ME1m ME2m ACONTm PGCD PYK |
| 164 | ME1m ME2m ACONTm PSERT PYK |
| 165 | ASPTA1m ME1m ME2m PSP_L PYK |
| 166 | ASPTA1m ME1m ME2m PGCD PYK |
| 167 | ASPTA1m ME1m ME2m PSERT PYK |
| 168 | ME1m ME2m ICDHy PSERT PYK |
| 169 | ME1m ME2m ACONT PSERT PYK |
| 170 | ME1m ME2m ACONT PSP_L PYK |
| 171 | ME1m ME2m ICDHy PSP_L PYK |
| 172 | ME1m ME2m ICDHy PGCD PYK |
| 173 | ME1m ME2m ACONT PGCD PYK |
| 174 | ME1m ME2m ICDHxm PSP_L PYK |
| 175 | ME1m ME2m ICDHxm PGCD PYK |
| 176 | ME1m ME2m ICDHxm PSERT PYK |
| 177 | ME1m ME2m G3PDm PYK SUCD3-u6m |
| 178 | ME1m ME2m PYK FRDm FUMm |
| 179 | ME1m PYK FRDm FUMm PGDH |
| 180 | ME1m G3PDm PYK SUCD3-u6m PGDH |
| 181 | ME1m PYK FRDm FUMm PGL |
| 182 | ME1m PYK FRDm FUMm G6PDH |
| 183 | ME1m G3PDm PYK SUCD3-u6m PGL |
| 184 | ME1m G3PDm PYK SUCD3-u6m G6PDH |
| 185 | ME1m G3PDm PYK SUCD3-u6m TKT1 |
| 186 | ME1m PYK FRDm FUMm TKT1 |
| 187 | ME1m G3PDm PYK SUCD3-u6m RPE |
| 188 | ME1m PYK FRDm FUMm RPE |
| 189 | ME1m PYK FRDm FUMm TKT2 |
| 190 | ME1m G3PDm PYK SUCD3-u6m TKT2 |
| 191 | ME1m ME2m PSP_L PYK PGDH |
| 192 | ME1m ME2m PSERT PYK PGDH |
| 193 | ME1m ME2m PGCD PYK PGDH |
| 194 | ME1m ME2m PSERT PYK PGL |
| 195 | ME1m ME2m PSERT PYK G6PDH |
| 196 | ME1m ME2m PGCD PYK PGL |
| 197 | ME1m ME2m PSP_L PYK PGL |
| 198 | ME1m ME2m PSP_L PYK G6PDH |
| 199 | ME1m ME2m PGCD PYK G6PDH |
| 200 | ME1m ME2m PSERT PYK TKT1 |
| 201 | ME1m ME2m PGCD PYK TKT1 |
| 202 | ME1m ME2m PSP_L PYK TKT1 |
| 203 | ME1m ME2m PSERT PYK RPE |
| 204 | ME1m ME2m PSP_L PYK RPE |
| 205 | ME1m ME2m PGCD PYK RPE |
| 206 | ME1m ME2m PSP_L PYK TKT2 |
| 207 | ME1m ME2m PSERT PYK TKT2 |
| 208 | ME1m ME2m PGCD PYK TKT2 |
| 209 | ATPSm FRDm FUMm PGDH PYRDC |
| 210 | G3PDm ATPSm SUCD3-u6m PGDH PYRDC |
| 211 | ATPSm FRDm FUMm G6PDH PYRDC |
| 212 | G3PDm ATPSm SUCD3-u6m PGL PYRDC |
| 213 | ATPSm FRDm FUMm PGL PYRDC |
| 214 | G3PDm ATPSm SUCD3-u6m G6PDH PYRDC |
| 215 | G3PDm ATPSm SUCD3-u6m TKT1 PYRDC |
| 216 | ATPSm FRDm FUMm TKT1 PYRDC |
| 217 | G3PDm SUCD3-u6m PGL PYRDC ATPtm-3H |
| 218 | FRDm FUMm PGDH PYRDC ATPtm-3H |
| 219 | G3PDm SUCD3-u6m PGDH PYRDC ATPtm-3H |
| 220 | G3PDm SUCD3-u6m G6PDH PYRDC ATPtm-3H |
| 221 | FRDm FUMm PGL PYRDC ATPtm-3H |
| 222 | FRDm FUMm G6PDH PYRDC ATPtm-3H |
| 223 | G3PDm SUCD3-u6m TKT1 PYRDC ATPtm-3H |
| 224 | FRDm FUMm TKT1 PYRDC ATPtm-3H |
| 225 | G3PDm ATPSm SUCD3-u6m RPE PYRDC |
| 226 | ATPSm FRDm FUMm RPE PYRDC |
| 227 | G3PDm SUCD3-u6m RPE PYRDC ATPtm-3H |
| 228 | FRDm FUMm RPE PYRDC ATPtm-3H |

TABLE 5-continued

The list of all strains identified by OptKnock that are most likely to provide increased fumarate yields in *S. Cerevisiae* under microaerobic culture conditions. These same designs can be used for malate production if the cytosolic fumarase (FUM) is deleted additionally.

| | |
|---|---|
| 229 | G3PDm ATPSm SUCD3-u6m TKT2 PYRDC |
| 230 | ATPSm FRDm FUMm TKT2 PYRDC |
| 231 | FRDm FUMm TKT2 PYRDC ATPtm-3H |
| 232 | G3PDm SUCD3-u6m TKT2 PYRDC ATPtm-3H |
| 233 | ME2m FRDm FUMm ALCD2x ATPtm-3H |
| 234 | ME2m G3PDm SUCD3-u6m ALCD2x ATPtm-3H |
| 235 | ME1m ME2m MTHFD SERD_L PYK G6PDH |
| 236 | ME1m ME2m MTHFD SERD_L PYK PGL |
| 237 | ME1m ME2m MTHFD SERD_L PYK PGDH |
| 238 | ASPTA1 GHMT2 ME1m SERD_L PDHm PYK |
| 239 | ORNTA ME1m MTHFD SERD_L PYK G6PDH |
| 240 | G3PD FRDm FUM PYRDC |
| 241 | G3PD FRDm FUMmPGDH PYRDC |
| 242 | G3PD FRDm FUMmPGL PYRDC |
| 243 | G3PD G3PD1irm SUCD3-u6m G6PDH PYRDC |
| 244 | G3PD G3PDm SUCD3-u6m PGL PYRDC |
| 245 | G3PD G3PD1irm SUCD3-u6m PGDH PYRDC |
| 246 | G3PD FRDm FUMmG6PDH PYRDC |
| 247 | G3PD G3PDm SUCD3-u6m G6PDH PYRDC |
| 248 | G3PD G3PD1irm SUCD3-u6m PGL PYRDC |
| 249 | G3PD G3PDm SUCD3-u6m PGDH PYRDC |
| 250 | G3PD G3PDm SUCD3-u6m TKT1 PYRDC |
| 251 | G3PD G3PD1irm SUCD3-u6m TKT1 PYRDC |
| 252 | G3PD FRDm FUMmTKT1 PYRDC |
| 253 | G3PD G3PD1irm SUCD3-u6m RPE PYRDC |
| 254 | G3PD G3PDm SUCD3-u6m RPE PYRDC |
| 255 | G3PD FRDm FUMmRPE PYRDC |
| 256 | G3PD G3PD1irm SUCD3-u6m TKT2 PYRDC |
| 257 | G3PD G3PDm SUCD3-u6m TKT2 PYRDC |
| 258 | G3PD FRDm FUMmTKT2 PYRDC |
| 259 | ASPTA1 G3PD G3PD1irm SUCD3-u6m PYRDC |
| 260 | ASPTA1 G3PD G3PDm SUCD3-u6m PYRDC |
| 261 | ASPTA1 G3PD FRDm FUMmPYRDC |
| 262 | G3PD G3PD1irm HSDxi SUCD3-u6m PYRDC |
| 263 | G3PD G3PDm HSDxi SUCD3-u6m PYRDC |
| 264 | G3PD HSDxi FRDm FUMmPYRDC |
| 265 | G3PD G3PD1irm SUCD3-u6m ALCD2x PYRDC |
| 266 | G3PD G3PDm SUCD3-u6m ALCD2x PYRDC |
| 267 | G3PD FRDm FUMmALCD2x PYRDC |
| 268 | ACONT GLUDC G3PD PYRDC ALDD2y |
| 269 | ICDHyG3PD G3PD1irm SUCD3-u6m PGL PYRDC |
| 270 | ICDHyG3PD FRDm FUMmG6PDH PYRDC |
| 271 | ACONT G3PD G3PD1irm SUCD3-u6m PGL PYRDC |
| 272 | ACONT G3PD FRDm FUMmPGDH PYRDC |
| 273 | ACONT G3PD G3PD1irm SUCD3-u6m G6PDH PYRDC |
| 274 | ICDHyG3PD G3PDm SUCD3-u6m G6PDH PYRDC |
| 275 | ACONT G3PD FRDm FUMmG6PDH PYRDC |
| 276 | ACONT G3PD G3PDm SUCD3-u6m G6PDH PYRDC |
| 277 | ACONT G3PD G3PDm SUCD3-u6m PGDH PYRDC |
| 278 | ICDHyG3PD G3PDm SUCD3-u6m PGL PYRDC |

TABLE 6

The list of all strains identified by OptKnock that are most likely to provide increased acrylate yields in *S. cerevisiae* under anaerobic conditions.

| | |
|---|---|
| 1 | PYRDC |
| 2 | ALCD2x |
| 3 | ATPtm-3H |
| 4 | ATPSm |
| 5 | ME1m |
| 6 | PDHm PYRDC |
| 7 | ME1m PYK |
| 8 | ATPSm ATPS |
| 9 | ME1m ATPS |
| 10 | ATPS ATPtm-3H |
| 11 | PDHm ATPtm-3H |
| 12 | PDHm ALCD2x |
| 13 | PDHm ATPSm |
| 14 | PSERT ALCD2x |
| 15 | PSP_L ALCD2x |
| 16 | PGCD ALCD2x |
| 17 | ALCD2x ATPS |
| 18 | PYRDC IPPSm |
| 19 | PGCD PYRDC |
| 20 | PSP_L PYRDC |
| 21 | PSERT PYRDC |
| 22 | PYRDC ATPS |
| 23 | PGCD ATPSm |
| 24 | PSP_L ATPSm |
| 25 | PSERT ATPSm |
| 26 | PSERT ATPtm-3H |
| 27 | PGCD ATPtm-3H |
| 28 | PSP_L ATPtm-3H |
| 29 | ME1m PDHm |
| 30 | ME1m PGCD |
| 31 | ME1m PSP_L |
| 32 | ME1m PSERT |
| 33 | GLU5K PYRDC |
| 34 | GHMT2m ATPSm |
| 35 | ATPtm-3H IPPSm |
| 36 | ALCD2x IPPSm |
| 37 | ATPSm IPPSm |
| 38 | PYK ATPSm |
| 39 | ORNTA ATPtm-3H |
| 40 | MDHm DHORD4u |
| 41 | G3PDm SUCD3-u6m ALCD2x |
| 42 | G3PDm ATPSm SUCD3-u6m |
| 43 | GLU5K PDHm PYRDC |
| 44 | PDHm PYRDC IPPS |
| 45 | G3PDm SUCD3-u6m ATPtm-3H |
| 46 | ME1m G3PDm SUCD3-u6m |
| 47 | PGCD PDHm ATPSm |
| 48 | PSP_L PDHm ATPSm |
| 49 | PSERT PDHm ATPSm |
| 50 | PSERT PDHm ALCD2x |
| 51 | PGCD PDHm ALCD2x |
| 52 | PSP_L PDHm ALCD2x |
| 53 | PDHm PYK ATPSm |
| 54 | ME1m PSP_L PYK |
| 55 | ME1m PSERT PYK |
| 56 | ME1m PGCD PYK |
| 57 | G3PDm SUCD3-u6m PYRDC |
| 58 | PSERT PDHm ATPtm-3H |
| 59 | PSP_L PDHm ATPtm-3H |
| 60 | PGCD PDHm ATPtm-3H |
| 61 | PGCD ATPSm ALCD2x |
| 62 | PSP_L ATPSm ALCD2x |
| 63 | PSERT ATPSm ALCD2x |
| 64 | ME2m ATPSm ATPS |
| 65 | ME1m PGCD PDHm |
| 66 | ME1m PSERT PDHm |
| 67 | ME1m PSP_L PDHm |
| 68 | ME2m ATPS ATPtm-3H |
| 69 | ME2m PYRDC ATPS |
| 70 | ORNTA ATPS ATPtm-3H |
| 71 | GHMT2m PDHm ATPSm |
| 72 | ACONT ATPS ATPtm-3H |
| 73 | ICDHyATPS ATPtm-3H |
| 74 | GHMT2 ATPS ATPtm-3H |
| 75 | ME1m PSP_L ALCD2x |
| 76 | ME1m PGCD ALCD2x |
| 77 | ME1m PSERT ALCD2x |
| 78 | ASPTA1m ATPS ATPtm-3H |
| 79 | FTHFLm PYK ATPSm |
| 80 | MTHFDm PYK ATPSm |
| 81 | MTHFCm PYK ATPSm |
| 82 | MTHFC ATPS ATPtm-3H |
| 83 | GHMT2 ALCD2x ATPS |
| 84 | PSP_L PYRDC IPPSm |
| 85 | PSERT PYRDC IPPSm |
| 86 | PGCD PYRDC IPPSm |
| 87 | ICDHyPYRDC ATPS |
| 88 | ACONT PYRDC ATPS |
| 89 | PGCD ATPSm IPPSm |
| 90 | PSP_L ATPSm IPPSm |
| 91 | PSERT ATPSm IPPSm |

TABLE 6-continued

The list of all strains identified by OptKnock that are most likely to provide increased acrylate yields in *S. cerevisiae* under anaerobic conditions.

| | |
|---|---|
| 92 | ORNTA PYRDC ATPS |
| 93 | PGCD ATPtm-3H IPPSm |
| 94 | PSERT ATPtm-3H IPPSm |
| 95 | PSP_L ATPtm-3H IPPSm |
| 96 | GLU5K ALCD2x ATPS |
| 97 | ALCD2x ATPS IPPS |
| 98 | GLU5K PYRDC IPPSm |
| 99 | GLU5K PGCD PYRDC |
| 100 | GLU5K PSP_L PYRDC |
| 101 | GLU5K PSERT PYRDC |
| 102 | GLU5K PYRDC ATPS |
| 103 | ORNTA PGCD ATPtm-3H |
| 104 | ORNTA PSERT ATPtm-3H |
| 105 | ORNTA PSP_L ATPtm-3H |
| 106 | PYK ATPSm ATPtm-3H |
| 107 | ASPTA1m PSERT ATPtm-3H |
| 108 | ASPTA1m PSP_L ATPtm-3H |
| 109 | ASPTA1m PGCD ATPtm-3H |
| 110 | PYK ATPSm IPPSm |
| 111 | GHMT2 GHMT2m ALCD2x |
| 112 | MTHFC PSP_L ATPtm-3H |
| 113 | MTHFC PGCD ATPtm-3H |
| 114 | MTHFC PSERT ATPtm-3H |
| 115 | GHMT2m ATPSm IPPSm |
| 116 | GHMT2 GHMT2m ATPtm-3H |
| 117 | GHMT2 GHMT2m PYRDC |
| 118 | GHMT2m PYK ATPSm |
| 119 | GLU5K GHMT2m ATPSm |
| 120 | G5SD G5SD2 PYRDC |
| 121 | GHMT2m ATPSm ALCD2x |
| 122 | ORNTA ATPtm-3H IPPSm |
| 123 | MTHFC GHMT2m ALCD2x |
| 124 | MTHFC GHMT2m ATPtm-3H |
| 125 | ME2m ICDHym ATPtm-3H |
| 126 | ME2m ACONTm ATPtm-3H |
| 127 | GLU5K ALCD2x THRA |
| 128 | ASPTA1m THRA ATPtm-3H |
| 129 | GHMT2 ME1m GHMT2m |
| 130 | PSERT MDHm DHORD4u |
| 131 | PSP_L MDHm DHORD4u |
| 132 | PGCD MDHm DHORD4u |
| 133 | ME1m MTHFC GHMT2m |
| 134 | MDHm DHORD4u ATPS |
| 135 | PDHm MDHm DHORD4u |
| 136 | MDHm DHORD4u IPPSm |
| 137 | ORNTA MDHm DHORD4u |
| 138 | MDHm DHORD4u ALDD2y |
| 139 | ASPTA1m MDHm DHORD4u |
| 140 | MDHm NADH2-u6m SUCD3-u6m |
| 141 | TPI MDH DHORD4u |
| 142 | MDH DHORD4u ATPS |
| 143 | FUM SUCD1rm ATPS |
| 144 | FUM FUMmATPS |
| 145 | TPI FUM SUCD1rm |
| 146 | TPI FUM FUMm |
| 147 | G3PDm PDHm SUCD3-u6m PYRDC |
| 148 | GLU5K G3PDm SUCD3-u6m ALCD2x |
| 149 | G3PDm SUCD3-u6m ALCD2x IPPS |
| 150 | GLU5K PDHm PYRDC IPPS |
| 151 | G5SD G5SD2 PDHm PYRDC |
| 152 | ASPTA1m ACONTm PDHm PYRDC |
| 153 | ME1m G3PDm PYK SUCD3-u6m |
| 154 | ORNTA G3PDm SUCD3-u6m ATPtm-3H |
| 155 | ME2m G3PDm SUCD3-u6m ATPtm-3H |
| 156 | ICDHyG3PDm SUCD3-u6m ATPtm-3H |
| 157 | ACONT G3PDm SUCD3-u6m ATPtm-3H |
| 158 | GHMT2 G3PDm SUCD3-u6m ATPtm-3H |
| 159 | ASPTA1m G3PDm SUCD3-u6m ATPtm-3H |
| 160 | MTHFC G3PDm SUCD3-u6m ATPtm-3H |
| 161 | ME2m G3PDm SUCD3-u6m PYRDC |
| 162 | ME1m ME2m PGCD PYK |
| 163 | ME1m ME2m PSP_L PYK |
| 164 | ME1m ME2m PSERT PYK |
| 165 | PDHm PYK ATPSm IPPSm |
| 166 | ORNTA ME1m PSP_L PYK |
| 167 | ORNTA ME1m PSERT PYK |
| 168 | ORNTA ME1m PGCD PYK |
| 169 | ICDHyG3PDm SUCD3-u6m PYRDC |
| 170 | ACONT G3PDm SUCD3-u6m PYRDC |
| 171 | ORNTA G3PDm SUCD3-u6m PYRDC |
| 172 | ORNTA PGCD PDHm ATPtm-3H |
| 173 | ORNTA PSERT PDHm ATPtm-3H |
| 174 | ORNTA PSP_L PDHm ATPtm-3H |
| 175 | ME1m PGCD PYK ATPSm |
| 176 | ME1m PSERT PYK ATPSm |
| 177 | ME1m PSP_L PYK ATPSm |
| 178 | G3PD G3PD1irm ATPSm SUCD3-u6m |
| 179 | MTHFD PSP_L PDHm ALCD2x |
| 180 | MTHFD PGCD PDHm ALCD2x |
| 181 | MTHFD PSERT PDHm ALCD2x |
| 182 | ME1m G3PD G3PD1irm SUCD3-u6m |
| 183 | MTHFC PSP_L PDHm ALCD2x |
| 184 | MTHFC PSERT PDHm ALCD2x |
| 185 | MTHFC PGCD PDHm ALCD2x |
| 186 | ASPTA1m PSP_L PDHm ALCD2x |
| 187 | ASPTA1m PGCD PDHm ALCD2x |
| 188 | ASPTA1m PSERT PDHm ALCD2x |
| 189 | ME2m PGCD PDHm ATPtm-3H |
| 190 | ME2m PSERT PDHm ATPtm-3H |
| 191 | ME2m PSP_L PDHm ATPtm-3H |
| 192 | ME1m MTHFC PSP_L PYK |
| 193 | ME1m MTHFC PSERT PYK |
| 194 | ME1m MTHFC PGCD PYK |
| 195 | ASPTA1m PGCD ATPSm ALCD2x |
| 196 | ASPTA1m PSERT ATPSm ALCD2x |
| 197 | ASPTA1m PSP_L ATPSm ALCD2x |
| 198 | GHMT2 PSP_L PDHm ATPtm-3H |
| 199 | GHMT2 PGCD PDHm ATPtm-3H |
| 200 | GHMT2 PSERT PDHm ATPtm-3H |
| 201 | ASPTA1m PGCD PDHm ATPtm-3H |
| 202 | ASPTA1m PSERT PDHm ATPtm-3H |
| 203 | ASPTA1m PSP_L PDHm ATPtm-3H |
| 204 | ACONT PSP_L PDHm ATPtm-3H |
| 205 | ACONT PSERT PDHm ATPtm-3H |
| 206 | ACONT PGCD PDHm ATPtm-3H |
| 207 | ICDHyPSP_L PDHm ATPtm-3H |
| 208 | ICDHyPGCD PDHm ATPtm-3H |
| 209 | ICDHyPSERT PDHm ATPtm-3H |
| 210 | MTHFC PSP_L PDHm ATPtm-3H |
| 211 | MTHFC PGCD PDHm ATPtm-3H |
| 212 | MTHFC PSERT PDHm ATPtm-3H |
| 213 | GLU5K G3PDm SUCD3-u6m PYRDC |
| 214 | G3PD G3PD1irm SUCD3-u6m ATPtm-3H |
| 215 | GHMT2 GHMT2m PDHm ATPtm-3H |
| 216 | MTHFDm PYK ATPSm IPPSm |
| 217 | MTHFCm PYK ATPSm IPPSm |
| 218 | FTHFLm PYK ATPSm IPPSm |
| 219 | ME2m PSP_L ALCD2x ATPtm-3H |
| 220 | ME2m PSERT ALCD2x ATPtm-3H |
| 221 | ME2m PGCD ALCD2x ATPtm-3H |
| 222 | GHMT2 GHMT2m PDHm ALCD2x |
| 223 | ME2m MTHFC ATPS ATPtm-3H |
| 224 | ME2m MTHFC PYRDC ATPS |
| 225 | GLU5K GHMT2m PDHm ATPSm |
| 226 | ORNTA ACONT ATPS ATPtm-3H |
| 227 | ORNTA ICDHyATPS ATPtm-3H |
| 228 | ORNTA ICDHyPYRDC ATPS |
| 229 | ORNTA ACONT PYRDC ATPS |
| 230 | ASPTA1m FTHFLm PYK ATPSm |
| 231 | ASPTA1m MTHFDm PYK ATPSm |
| 232 | ASPTA1m MTHFCm PYK ATPSm |
| 233 | ORNTA MTHFC ATPS ATPtm-3H |
| 234 | GHMT2 GHMT2m PDHm ATPSm |
| 235 | MTHFC PSERT PYK ATPSm |
| 236 | MTHFC PGCD PYK ATPSm |
| 237 | MTHFC PSP_L PYK ATPSm |
| 238 | GHMT2 ICDHyATPS ATPtm-3H |
| 239 | GHMT2 ACONT ATPS ATPtm-3H |
| 240 | G3PD G3PD1irm SUCD3-u6m PYRDC |
| 241 | FTHFLr PSERT PYK ATPSm |
| 242 | FTHFLr PSP_L PYK ATPSm |
| 243 | FTHFLr PGCD PYK ATPSm |

TABLE 6-continued

The list of all strains identified by OptKnock that are most likely to provide increased acrylate yields in *S. cerevisiae* under anaerobic conditions.

| # | Strain |
|---|---|
| 244 | ACONT PSERT ALCD2x ATPtm-3H |
| 245 | ICDHyPSP_L ALCD2x ATPtm-3H |
| 246 | ACONT PGCD ALCD2x ATPtm-3H |
| 247 | ICDHyPGCD ALCD2x ATPtm-3H |
| 248 | ICDHyPSERT ALCD2x ATPtm-3H |
| 249 | ACONT PSP_L ALCD2x ATPtm-3H |
| 250 | ICDHyPYK ATPSm ATPtm-3H |
| 251 | ACONT PYK ATPSm ATPtm-3H |
| 252 | ICDHyMTHFC ATPS ATPtm-3H |
| 253 | ACONT MTHFC ATPS ATPtm-3H |
| 254 | ORNTA PGCD ALCD2x ATPtm-3H |
| 255 | ORNTA PSERT ALCD2x ATPtm-3H |
| 256 | ORNTA PSP_L ALCD2x ATPtm-3H |
| 257 | MTHFDm PSP_L PYK ATPSm |
| 258 | FTHFLm PGCD PYK ATPSm |
| 259 | MTHFCm PSP_L PYK ATPSm |
| 260 | MTHFDm PSERT PYK ATPSm |
| 261 | MTHFDm PGCD PYK ATPSm |
| 262 | MTHFCm PGCD PYK ATPSm |
| 263 | MTHFCm PSERT PYK ATPSm |
| 264 | FTHFLm PSERT PYK ATPSm |
| 265 | FTHFLm PSP_L PYK ATPSm |
| 266 | MTHFD MTHFD2 ATPS ATPtm-3H |
| 267 | ORNTA PYK ATPSm ATPtm-3H |
| 268 | ASPTA1m MTHFC ATPS ATPtm-3H |
| 269 | MTHFC PYK ATPSm ATPtm-3H |
| 270 | ICDHyGLY3PP PYRDC ATPS |
| 271 | ACONT GLY3PP PYRDC ATPS |
| 272 | ICDHyG3PD PYRDC ATPS |
| 273 | ACONT G3PD PYRDC ATPS |
| 274 | MTHFC GHMT2m PDHm ATPtm-3H |
| 275 | MTHFC GHMT2m PDHm ALCD2x |
| 276 | GHMT2 PSERT ALCD2x ATPS |
| 277 | GHMT2 PGCD ALCD2x ATPS |
| 278 | GHMT2 PSP_L ALCD2x ATPS |
| 279 | FTHFLr PYK ATPSm ATPtm-3H |
| 280 | PYK ATPSm ATPtm-3H IPPSm |
| 281 | ACONT MTHFC PYRDC ATPS |
| 282 | ICDHyMTHFC PYRDC ATPS |
| 283 | ORNTA MTHFC PYRDC ATPS |
| 284 | GHMT2 FTHFCLm ALCD2x ATPS |
| 285 | GHMT2 THFATm ALCD2x ATPS |
| 286 | GHMT2 ALCD2x ATPS IPPS |
| 287 | ORNTA PDHm THRA ATPtm-3H |
| 288 | GLU5K PSERT PYRDC IPPSm |
| 289 | GLU5K PGCD PYRDC IPPSm |
| 290 | GLU5K PSP_L PYRDC IPPSm |
| 291 | ASPTA1m ORNTA PYRDC ATPS |
| 292 | ORNTA PGCD ATPtm-3H IPPSm |
| 293 | ORNTA PSERT ATPtm-3H IPPSm |
| 294 | ORNTA PSP_L ATPtm-3H IPPSm |
| 295 | PGCD PYK ATPSm ATPtm-3H |
| 296 | PSP_L PYK ATPSm ATPtm-3H |
| 297 | PSERT PYK ATPSm ATPtm-3H |
| 298 | ASPTA1m PSERT ATPtm-3H IPPSm |
| 299 | ASPTA1m PGCD ATPtm-3H IPPSm |
| 300 | ASPTA1m PSP_L ATPtm-3H IPPSm |
| 301 | ME1m G3PD MDHm SUCD3-u6m |
| 302 | MTHFC PGCD ATPtm-3H IPPSm |
| 303 | MTHFC PSP_L ATPtm-3H IPPSm |
| 304 | MTHFC PSERT ATPtm-3H IPPSm |
| 305 | GHMT2 PSERT ALCD2x ATPtm-3H |
| 306 | GHMT2 PSP_L ALCD2x ATPtm-3H |
| 307 | GHMT2 PGCD ALCD2x ATPtm-3H |
| 308 | G3PD MDHm SUCD3-u6m PYRDC |
| 309 | GHMT2 GHMT2m ALCD2x ATPtm-3H |
| 310 | GLU5K PSP_L ALCD2x ATPS |
| 311 | GLU5K PSERT ALCD2x ATPS |
| 312 | GLU5K PGCD ALCD2x ATPS |
| 313 | PSERT PDHm MDHm DHORD4u |
| 314 | PSP_L PDHm MDHm DHORD4u |
| 315 | PGCD PDHm MDHm DHORD4u |
| 316 | GLU5K PSP_L ALCD2x PYRDC |
| 317 | GLU5K PGCD ALCD2x PYRDC |
| 318 | GLU5K PSERT ALCD2x PYRDC |
| 319 | GLU5K ALCD2x ATPS IPPS |
| 320 | PSP_L ALCD2x ATPS IPPS |
| 321 | PGCD ALCD2x ATPS IPPS |
| 322 | PSERT ALCD2x ATPS IPPS |
| 323 | ASPTA1m PYK ATPSm ATPtm-3H |
| 324 | GHMT2 ME1m GHMT2m PDHm |
| 325 | MTHFD G3PD PYRDC ATPS |
| 326 | MTHFD GLY3PP PYRDC ATPS |
| 327 | G5SD G5SD2 ALCD2x ATPS |
| 328 | ACONT ICDHxm PYK ATPSm |
| 329 | ICDHxm ICDHyPYK ATPSm |
| 330 | ASPTA1m ACONTm ALCD2x ATPS |
| 331 | ASPTA1m G5SD2 ALCD2x ATPS |
| 332 | G5SD G5SD2 PYRDC IPPSm |
| 333 | G5SD G5SD2 PSP_L PYRDC |
| 334 | G5SD G5SD2 PSERT PYRDC |
| 335 | G5SD G5SD2 PGCD PYRDC |
| 336 | MTHFC G3PD PYRDC ATPS |
| 337 | MTHFC GLY3PP PYRDC ATPS |
| 338 | G5SD G5SD2 PYRDC ATPS |
| 339 | GLU5K GHMT2m ATPSm ALCD2x |
| 340 | GHMT2 GHMT2m ATPtm-3H IPPSm |
| 341 | GHMT2m PYK ATPSm ATPtm-3H |
| 342 | G3PD MDHm SUCD3-u6m ALCD2x |
| 343 | ASPTA1m MTHFC PGCD ATPtm-3H |
| 344 | ASPTA1m MTHFC PSERT ATPtm-3H |
| 345 | ASPTA1m MTHFC PSP_L ATPtm-3H |
| 346 | ASPTA1m ME2m PSP_L ATPtm-3H |
| 347 | ASPTA1m ME2m PSERT ATPtm-3H |
| 348 | ASPTA1m ME2m PGCD ATPtm-3H |
| 349 | GHMT2m PYK ATPSm IPPSm |
| 350 | GLU5K GHMT2m ATPSm IPPSm |
| 351 | ME2m ICDHym PGCD ATPtm-3H |
| 352 | ME2m ACONTm PSP_L ATPtm-3H |
| 353 | ME2m ICDHym PSP_L ATPtm-3H |
| 354 | ME2m ACONTm PSERT ATPtm-3H |
| 355 | ME2m ACONTm PGCD ATPtm-3H |
| 356 | ME2m ICDHym PSERT ATPtm-3H |
| 357 | MTHFD MTHFD2 GHMT2m ALCD2x |
| 358 | MTHFD MTHFD2 PSP_L ATPtm-3H |
| 359 | MTHFD MTHFD2 PSERT ATPtm-3H |
| 360 | MTHFD MTHFD2 PGCD ATPtm-3H |
| 361 | GHMT2 GHMT2m ATPSm IPPSm |
| 362 | GHMT2m PYK ATPSm ALCD2x |
| 363 | ME1m MTHFC GHMT2m PDHm |
| 364 | THFATm PYK ATPtm-3H IPPSm |
| 365 | FTHFCLm PYK ATPtm-3H IPPSm |
| 366 | ACONT GHMT2m PYK ATPSm |
| 367 | ICDHyGHMT2m PYK ATPSm |
| 368 | GHMT2 ORNTA GHMT2m ATPtm-3H |
| 369 | GHMT2 THFATm GHMT2m PYRDC |
| 370 | GHMT2 FTHFCLm GHMT2m PYRDC |
| 371 | ME2m GLU5K ACONTm PYRDC |
| 372 | ME2m GLU5K ICDHym PYRDC |
| 373 | MTHFD MTHFD2 GHMT2m ATPtm-3H |
| 374 | MTHFD MTHFD2 GHMT2m PYRDC |
| 375 | G5SD2 GHMT2m PYK ATPSm |
| 376 | GLU5K GHMT2m PYK ATPSm |
| 377 | ASPTA1m GHMT2m PYK ATPSm |
| 378 | MTHFD MTHFD2 GHMT2m ATPSm |
| 379 | G5SD G5SD2 GHMT2m ATPSm |
| 380 | MTHFC GHMT2m ATPtm-3H IPPSm |
| 381 | ASPTA1m ACONTm GHMT2m ATPSm |
| 382 | MTHFC GHMT2m ALCD2x IPPSm |
| 383 | ME2m MTHFC PYK ATPSm |
| 384 | ASPTA1m G5SD2 GHMT2m ATPSm |
| 385 | G5SD2 MTHFD GHMT2m ATPSm |
| 386 | ME2m FTHFLr PYK ATPSm |
| 387 | THFATm PYK TKT2 ATPtm-3H |
| 388 | FTHFCLm PYK TKT2 ATPtm-3H |
| 389 | ORNTA THFATm PYK ATPtm-3H |
| 390 | ORNTA FTHFCLm PYK ATPtm-3H |
| 391 | ASPTA1m FTHFCLm PYK ATPtm-3H |
| 392 | ASPTA1m THFATm PYK ATPtm-3H |
| 393 | ORNTA MTHFC GHMT2m ATPtm-3H |
| 394 | PDHm ATPSm MDHm PPND |
| 395 | MTHFC THFATm PYK ATPtm-3H |

TABLE 6-continued

The list of all strains identified by OptKnock that are most likely to provide increased acrylate yields in S. cerevisiae under anaerobic conditions.

| | |
|---|---|
| 396 | FTHFCLm MTHFC PYK ATPtm-3H |
| 397 | GHMT2 THFATm PYK ATPtm-3H |
| 398 | GHMT2 FTHFCLm PYK ATPtm-3H |
| 399 | GHMT2 ORNTA FTHFCLm ALCD2x |
| 400 | GHMT2 ORNTA THFATm ALCD2x |
| 401 | G5SD G5SD2 ALCD2x THRA |
| 402 | PSP_L MDHm DHORD4u IPPSm |
| 403 | PSERT MDHm DHORD4u IPPSm |
| 404 | PGCD MDHm DHORD4u IPPSm |
| 405 | ORNTA PSERT MDHm DHORD4u |
| 406 | ORNTA PSP_L MDHm DHORD4u |
| 407 | ORNTA PGCD MDHm DHORD4u |
| 408 | GHMT2 ORNTA ME1m GHMT2m |
| 409 | ME1m MTHFD MTHFD2 GHMT2m |
| 410 | PSERT MDHm DHORD4u ALDD2y |
| 411 | PGCD MDHm DHORD4u ALDD2y |
| 412 | PSP_L MDHm DHORD4u ALDD2y |
| 413 | ASPTA1m PGCD MDHm DHORD4u |
| 414 | ASPTA1m PSP_L MDHm DHORD4u |
| 415 | ASPTA1m PSERT MDHm DHORD4u |
| 416 | PGCD MDHm NADH2-u6m SUCD3-u6m |
| 417 | PSERT MDHm NADH2-u6m SUCD3-u6m |
| 418 | PSP_L MDHm NADH2-u6m SUCD3-u6m |
| 419 | PYK MDHm DHORD4u ATPS |
| 420 | MDHm NADH2-u6m SUCD3-u6m ATPS |
| 421 | PDHm MDHm DHORD4u ALDD2y |
| 422 | GHMT2 GHMT2m MDHm DHORD4u |
| 423 | ORNTA PDHm MDHm DHORD4u |
| 424 | ASPTA1m PDHm MDHm DHORD4u |
| 425 | PDHm MDHm NADH2-u6m SUCD3-u6m |
| 426 | ORNTA MDHm DHORD4u IPPSm |
| 427 | MDHm DHORD4u ALDD2y IPPSm |
| 428 | ASPTA1m MDHm DHORD4u IPPSm |
| 429 | MDHm NADH2-u6m SUCD3-u6m IPPSm |
| 430 | MTHFC GHMT2m MDHm DHORD4u |
| 431 | ORNTA MDHm DHORD4u ALDD2y |
| 432 | ME2m ICDHym MDHm DHORD4u |
| 433 | ME2m ACONTm MDHm DHORD4u |
| 434 | ORNTA MDHm NADH2-u6m SUCD3-u6m |
| 435 | ASPTA1m MDHm DHORD4u ALDD2y |
| 436 | MDHm NADH2-u6m SUCD3-u6m ALDD2y |
| 437 | ASPTA1m MDHm NADH2-u6m SUCD3-u6m |
| 438 | PSERT TPI MDH DHORD4u |
| 439 | PSP_L TPI MDH DHORD4u |
| 440 | PGCD TPI MDH DHORD4u |
| 441 | TPI MDH DHORD4u THRA |
| 442 | PDHm TPI MDH DHORD4u |
| 443 | TPI FDH MDH DHORD4u |
| 444 | TPI MDH NADH2-u6m SUCD3-u6m |
| 445 | G3PDm TPI MDH NADH2-u6m |
| 446 | G3PD1irm TPI MDH NADH2-u6m |
| 447 | GLYCLm PGI MDH DHORD4u |
| 448 | GHMT2 PGI MDH DHORD4u |
| 449 | GHMT2m PGI MDH DHORD4u |
| 450 | G3PD1irm PGI MDH NADH2-u6m |
| 451 | G3PDm PGI MDH NADH2-u6m |
| 452 | MDH DHORD4u ATPS ALDD2y |
| 453 | ME2m MDH DHORD4u ATPS |
| 454 | ICDHy MDH DHORD4u ATPS |
| 455 | ACONT MDH DHORD4u ATPS |
| 456 | GHMT2 MDH DHORD4u ATPS |
| 457 | ORNTA MDH DHORD4u ATPS |
| 458 | MTHFC MDH DHORD4u ATPS |
| 459 | MDH NADH2-u6m SUCD3-u6m ATPS |
| 460 | G3PD1irm MDH NADH2-u6m ATPS |
| 461 | G3PDm MDH NADH2-u6m ATPS |
| 462 | ASPTA1 FUM FUMmATPS |
| 463 | PSERT TPI FUM FUMm |
| 464 | PSP_L TPI FUM FUMm |
| 465 | PGCD TPI FUM FUMm |
| 466 | G3PDm FUM FUMm SUCD3-u6m |
| 467 | G3PDm FUM SUCD1rm SUCD3-u6m |
| 468 | G3PDm MDH SUCD3-u6m DHORD4u |
| 469 | G3PDm MDH NADH2-u6m SUCD3-u6m |
| 470 | ASPTA1 TPI FUM FUMm |
| 471 | FTHFLr TPI FUM FUMm |
| 472 | MTHFC TPI FUM FUMm |
| 473 | GHMT2 TPI FUM FUMm |
| 474 | GLU5K G3PDm PDHm SUCD3-u6m PYRDC |
| 475 | G3PDm PDHm SUCD3-u6m PYRDC IPPS |
| 476 | GLU5K G3PDm SUCD3-u6m ALCD2x IPPS |
| 477 | G5SD G5SD2 G3PDm SUCD3-u6m ALCD2x |
| 478 | ASPTA1m ACONTm G3PDm SUCD3-u6m ALCD2x |
| 479 | G3PDm NADH2-u6cmNADH2-u6m DHORD4u ALCD2x |
| 480 | G3PD PDHm MDHm SUCD3-u6m PYRDC |
| 481 | G5SD G5SD2 PDHm PYRDC IPPS |
| 482 | G3PDm ATPSm NADH2-u6cmNADH2-u6m DHORD4u |
| 483 | ASPTA1m ACONTm PDHm PYRDC IPPS |
| 484 | ASPTA1m ICDHxm ICDHym PDHm PYRDC |
| 485 | ORNTA MTHFC G3PDm SUCD3-u6m ATPtm-3H |
| 486 | G3PD PDHm MDHm SUCD3-u6m ALCD2x |
| 487 | ME2m MTHFD G3PDm SUCD3-u6m ATPtm-3H |
| 488 | GHMT2 ME2m G3PDm SUCD3-u6m ATPtm-3H |
| 489 | ACONT MTHFC G3PDm SUCD3-u6m ATPtm-3H |
| 490 | ICDHyMTHFC G3PDm SUCD3-u6m ATPtm-3H |
| 491 | MTHFD MTHFD2 G3PDm SUCD3-u6m ATPtm-3H |
| 492 | ASPTA1m GHMT2 G3PDm SUCD3-u6m ATPtm-3H |
| 493 | ASPTA1m MTHFC G3PDm SUCD3-u6m ATPtm-3H |
| 494 | MTHFD G3PDm GHMT2m SUCD3-u6m ATPtm-3H |
| 495 | G3PDm NADH2-u6cmNADH2-u6m DHORD4u ATPtm-3H |

TABLE 7

A list of all the reaction stoichiometries and the associated genes known to be associated with the reactions identified for disruption in the strains listed in Tables 5 and 6.

| Reaction Abbreviation | Reaction Name | Reaction Stoichiometry | Associated genes |
|---|---|---|---|
| ACONT | aconitase | [c]: cit <==> icit | YLR304C |
| ACONTm | aconitate hydratase | [m]: cit <==> icit | YJL200C, YLR304C |
| AGT | alanine-glyoxylate transaminase | [c]: ala-L + glx <==> gly + pyr | YFL030W |
| AKGDam | oxoglutarate dehydrogenase (lipoamide) | [m]: akg + h + lpam <==> co2 + sdhlam | YIL125W, YDR148C, YFL018C |
| AKGDbm | oxoglutarate dehydrogenase (dihydrolipoamide S-succinyltransferase) | [m]: coa + sdhlam --> dhlam + succoa | YIL125W, YDR148C, YFL018C |
| ALATA_L | L-alanine transaminase | [c]: akg + ala-L <==> glu-L + pyr | YDR111C |

TABLE 7-continued

A list of all the reaction stoichiometries and the associated genes known to be associated with the reactions identified for disruption in the strains listed in Tables 5 and 6.

| Reaction Abbreviation | Reaction Name | Reaction Stoichiometry | Associated genes |
|---|---|---|---|
| ALCD2x | alcohol dehydrogenase (ethanol: NAD) | [c]: etoh + nad <==> acald + h + nadh | YGL256W, YMR303C, YDL168W, YOL086C, YBR145W |
| ASPTA1 | aspartate transaminase | [c]: akg + asp-L <==> glu-L + oaa | YLR027C |
| ASPTA1m | aspartate transaminase, mitochondrial | [m]: akg + asp-L <==> glu-L + oaa | YKL106W |
| ATPSm | ATP synthase, mitochondrial | adp[m] + (3) h[c] + pi[m] --> atp[m] + (2) h[m] + h2o[m] | YBL099W+YPL078C+YDL004W+YDR377W+YOL077W-A+YJR121W+YDR322C-A+Q0080+YBR039W+YDL181W+Q0130+YKL016C+YDR298C+YML081C-A+YPL271W+Q0085+YPR020W+YLR295C, YBL099W+YDL004W+YPL078C+YDR377W+YJR121W+Q0080+YBR039W+YDL181W+YKL016C+Q0130+YDR298C+YML081C-A+YPL271W+Q0085+YLR295C |
| ATPtm-3H | ADP/ATP transporter, mitochondrial | adp[c] + atp[m] + (3) h[c] --> adp[m] + atp[c] + (3) h[m] | YBL030C, YBR085W, YMR056C |
| FRDcm | fumarate reductase, cytosolic/mitochondrial | fadh2[m] + fum[c] --> fad[m] + succ[c] | YEL047C |
| FRDm | fumarate reductase | [m]: fadh2 + fum --> fad + succ | YJR051W |
| FUMm | fumarase, mitochondrial | [m]: fum + h2o <==> mal-L | YPL262W |
| G3PD | Glycerol-3-phosphate dehydrogenase (NAD) | [c]: dhap + h + nadh --> glyc3p + nad | YDL022W |
| G3PD1irm | glycerol-3-phosphate dehydrogenase (NAD), mitochondrial | [m]: dhap + h + nadh --> glyc3p + nad | YOL059W |
| G3PDm | glycerol-3-phosphate dehydrogenase | [m]: fad + glyc3p --> dhap + fadh2 | YIL155C |
| G6PDH | glucose 6-phosphate dehydrogenase | [c]: g6p + nadp --> 6pgl + h + nadph | YNL241C |
| GHMT2 | glycine hydroxymethyltransferase | [c]: ser-L + thf --> gly + h2o + mlthf | YLR058C |
| GLY3PP | glycerol-3-phosphatase | [c]: glyc3p + h2o --> glyc + pi | YER062C, YIL053W |
| HSDxi | homoserine dehydrogenase (NADH), irreversible | [c]: aspsa + h + nadh --> hom-L + nad | YJR139C |
| HSK | homoserine kinase | [c]: atp + hom-L --> adp + h + phom | YHR025W |
| ICDHxm | Isocitrate dehydrogenase (NAD+) | [m]: icit + nad --> akg + co2 + nadh | YOR136W+YNL037C |
| ICDHy | isocitrate dehydrogenase (NADP) | [c]: icit + nadp <==> akg + co2 + nadph | YLR174W |
| ICL | Isocitrate lyase | [c]: icit --> glx + succ | YER065C |
| MDH | malate dehydrogenase | [c]: mal-L + nad <==> h + nadh + oaa | YOL126C |
| MDHm | malate dehydrogenase, mitochondrial | [m]: mal-L + nad <==> h + nadh + oaa | YKL085W |
| ME1m | malic enzyme (NAD), mitochondrial | [m]: mal-L + nad --> co2 + nadh + pyr | YKL029C |
| ME2m | malic enzyme (NADP), mitochondrial | [m]: mal-L + nadp --> co2 + nadph + pyr | YKL029C |
| MTHFD | methylenetetrahydrofolate dehydrogenase (NADP) | [c]: mlthf + nadp <==> methf + nadph | YGR204W |
| NADH2-u6cm | NADH dehydrogenase, cytosolic/mitochondrial | h[c] + nadh[c] + q6[m] --> nad[c] + q6h2[m] | YMR145C, YDL085W |
| ORNTA | ornithine transaminase | [c]: akg + orn-L --> glu-L + glu5sa | YLR438W |
| P5CDm | 1-pyrroline-5-carboxylate dehydrogenase, mitochondrial | [m]: 1pyr5c + (2) h2o + nad --> glu-L + h + nadh | |
| PDHcm | part of pyruvate dehydrogenase (dihydrolipoamide dehydrogenase) | [m]: dhlam + nad --> h + lpam + nadh | YIL125W, YDR148C, YFL018C |

TABLE 7-continued

A list of all the reaction stoichiometries and the associated genes known to be associated with the reactions identified for disruption in the strains listed in Tables 5 and 6.

| Reaction Abbreviation | Reaction Name | Reaction Stoichiometry | Associated genes |
|---|---|---|---|
| PDHm | pyruvate dehydrogenase, mitochondrial | [m]: coa + nad + pyr --> accoa + co2 + nadh | YER178W+YBR221C, YNL071W, YFL018C |
| PGCD | phosphoglycerate dehydrogenase | [c]: 3pg + nad --> 3php + h + nadh | YIL074C, YER081W |
| PGDH | phosphogluconate dehydrogenase | [c]: 6pgc + nadp --> co2 + nadph + ru5p-D | YHR183W, YGR256W |
| PGL | 6-phosphogluconolactonase | [c]: 6pgl + h2o --> 6pgc + h | YNR034W, YGR248W, YHR163W |
| PRO1xm | proline oxidase (NAD), mitochondrial | [m]: nad + pro-L --> 1pyr5c + (2) h + nadh | YLR142W |
| PSERT | phosphoserine transaminase | [c]: 3php + glu-L --> akg + pser-L | YOR184W |
| PSP_L | phosphoserine phosphatase (L-serine) | [c]: h2o + pser-L --> pi + ser-L | YGR208W |
| PYK | pyruvate kinase | [c]: adp + h + pep --> atp + pyr | YAL038W, YOR347C |
| PYRDC | pyruvate decarboxylase | [c]: h + pyr --> acald + co2 | YGR087C, YLR044C, YLR134W |
| RPE | ribulose 5-phosphate 3-epimerase | [c]: ru5p-D <==> xu5p-D | YJL121C |
| SERD_L | L-serine deaminase | [c]: ser-L --> nh4 + pyr | YIL168W, YCL064C |
| SUCD2_u6m | succinate dehydrogenase (ubiquinone-6), mitochondrial | [m]: q6 + succ <==> fum + q6h2 | YKL148C+YMR118C+YLL041C+YDR178W, YKL141W+YLL041C+YJL045W+YDR178W, YKL148C+YKL141W+YLL041C+YLR164W, YKL148C+YKL141W+YLL041C+YDR178W |
| SUCD3-u6m | succinate dehydrogenase (ubiquinone-6), mitochondrial | [m]: fadh2 + q6 <==> fad + q6h2 | YKL148C+YMR118C+YLL041C+YDR178W, YKL141W+YLL041C+YJL045W+YDR178W, YKL148C+YKL141W+YLL041C+YLR164W, YKL148C+YKL141W+YLL041C+YDR178W |
| SUCOASAm | Succinate--CoA ligase (ADP-forming) | [m]: atp + coa + succ <==> adp + pi + succoa | YOR142W+YGR244C |
| THRA | threonine aldolase | [c]: thr-L <==> acald + gly | YEL046C |
| THRS | threonine synthase | [c]: h2o + phom --> pi + thr-L | YCR053W |
| TKT2 | transketolase | [c]: e4p + xu5p-D <==> f6p + g3p | YBR117C, YPR074C |

[c] refers to cytosol and
[m] refers to mitochondrion, indicating the organelle where the reaction takes place

TABLE 8

List of the metabolite abbreviations, the corresponding names of all the metabolites that participate in the reactions listed in Table 7.

| Metabolite Abbreviation | Metabolite Name |
|---|---|
| 1pyr5c | 1-Pyrroline-5-carboxylate |
| 3pg | 3-Phospho-D-glycerate |
| 3php | 3-Phosphohydroxypyruvate |
| 6pgc | 6-Phospho-D-gluconate |
| 6pgl | 6-phospho-D-glucono-1,5-lactone |
| acald | Acetaldehyde |
| accoa | Acetyl-CoA |
| adp | ADP |
| akg | 2-Oxoglutarate |
| ala-L | L-Alanine |
| asp-L | L-Aspartate |
| aspsa | L-Aspartate 4-semialdehyde |
| atp | ATP |
| cit | Citrate |
| co2 | CO2 |
| coa | Coenzyme A |
| dhap | Dihydroxyacetone phosphate |
| dhlam | Dihydrolipoamide |
| e4p | D-Erythrose 4-phosphate |
| etoh | Ethanol |
| f6p | D-Fructose 6-phosphate |
| fad | FAD |
| fadh2 | FADH2 |
| fum | Fumarate |
| g3p | Glyceraldehyde 3-phosphate |
| g6p | D-Glucose 6-phosphate |
| glu-L | L-Glutamate |
| glu5sa | L-Glutamate 5-semialdehyde |
| glx | Glyoxylate |
| gly | Glycine |
| glyc | Glycerol |
| glyc3p | sn-Glycerol 3-phosphate |
| h | H+ |
| h2o | H2O |
| hom-L | L-Homoserine |
| icit | Isocitrate |
| lpam | Lipoamide |
| mal-L | L-Malate |
| methf | 5,10-Methenyltetrahydrofolate |
| mlthf | 5,10-Methylenetetrahydrofolate |
| nad | Nicotinamide adenine dinucleotide |
| nadh | Nicotinamide adenine dinucleotide - reduced |
| nh4 | Ammonium |
| oaa | Oxaloacetate |
| orn-L | L-Ornithine |
| pep | Phosphoenolpyruvate |

TABLE 8-continued

List of the metabolite abbreviations, the corresponding names of all the metabolites that participate in the reactions listed in Table 7.

| Metabolite Abbreviation | Metabolite Name |
| --- | --- |
| phom | O-Phospho-L-homoserine |
| pi | Phosphate |
| pro-L | L-Proline |
| pser-L | O-Phospho-L-serine |
| pyr | Pyruvate |
| q6 | Ubiquinone-6 |
| q6h2 | Ubiquinol-6 |
| ru5p-D | D-Ribulose 5-phosphate |
| sdhlam | S-Succinyldihydrolipoamide |
| ser-L | L-Serine |
| succ | Succinate |
| succoa | Succinyl-CoA |
| thf | 5,6,7,8-Tetrahydrofolate |
| thr-L | L-Threonine |
| xu5p-D | D-Xylulose 5-phosphate |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally occurring eukaryotic microbial organism, comprising one or more endogenous gene disruptions, said one or more gene disruptions occurring in genes encoding enzymes selected from the group consisting of
   (a) a glycerol-3-phosphate dehydrogenase, a pyruvate decarboxylase, a soluble fumarate reductase, a mitochondrial fumarase, and a cytosolic fumarase; or
   (b) a malic enzyme, a pyruvate kinase, a soluble fumarate reductase, a mitochondrial fumarase, and a cytosolic fumarase; and
   wherein said one or more gene disruptions confers enhanced production of malate onto said non-naturally occurring eukaryotic microbial organism compared to a wild-type strain.

2. The non-naturally occurring eukaryotic microbial organism of claim 1, wherein said organism is in culture medium comprising dissolved oxygen in an amount that is less than 10% of saturation, or wherein said microbial organism is in culture medium wherein the culture medium is in an atmosphere of less than 1% oxygen.

3. The non-naturally occurring eukaryotic microbial organism of claim 1, wherein said one or more gene disruptions comprises a deletion of said one or more genes.

4. The non-naturally occurring eukaryotic microbial organism of claim 1, further comprising an endogenous gene disruption of an encoded glucose-6-phosphate dehydrogenase.

5. The non-naturally occurring eukaryotic microbial organism of claim 4, further comprising an endogenous gene disruption of an encoded cytosolic NADP-dependent isocitrate dehydrogenase.

6. A method for producing malic acid, comprising culturing the non-naturally occurring eukaryotic microbial organism according to claim 1.

7. The method of claim 6, wherein said culturing is conducted in a culture medium comprising dissolved oxygen in an amount that is less than 10% of saturation, or wherein said microbial organism is in culture medium wherein the culture medium is in an atmosphere of less than 1% oxygen.

8. The method of claim 6, wherein said one or more gene disruptions comprises a deletion of said one or more genes.

9. The method of claim 6, wherein said one or more gene disruptions encode enzymes selected from the group consisting of a glycerol-3-phosphate dehydrogenase, a pyruvate decarboxylase, a soluble fumarate reductase, a mitochondrial fumarase, and a cytosolic fumarase.

10. The method of claim 9, wherein the non-naturally occurring eukaryotic microbial organism further comprises an endogenous gene disruption of an encoded glucose-6-phosphate dehydrogenase.

11. The method of claim 10, wherein the non-naturally occurring eukaryotic microbial organism further comprises an endogenous gene disruption of an encoded cytosolic NADP-dependent isocitrate dehydrogenase.

12. The method of claim 6, wherein said one or more gene disruptions encode enzymes selected from the group consisting of a malic enzyme, a pyruvate kinase, a soluble fumarate reductase, a mitochondrial fumarase, and a cytosolic fumarase.

* * * * *